US008865657B2

(12) United States Patent
Frevert et al.

(10) Patent No.: US 8,865,657 B2
(45) Date of Patent: Oct. 21, 2014

(54) COMPOSITIONS AND METHODS FOR INACTIVATING OR SUPPRESSING INFLAMMATORY CELLS

(75) Inventors: Ute Frevert, Warwick, NY (US); Ivan Usynin, Bronx, NY (US)

(73) Assignee: New York University, New York, NY (US)

( * ) Notice: Subject to any disclaimer, the term of this patent is extended or adjusted under 35 U.S.C. 154(b) by 1014 days.

(21) Appl. No.: 11/506,611

(22) Filed: Aug. 18, 2006

(65) Prior Publication Data
US 2007/0041992 A1 Feb. 22, 2007

Related U.S. Application Data

(60) Provisional application No. 60/709,522, filed on Aug. 19, 2005.

(51) Int. Cl.
*A61K 38/10* (2006.01)
*A61K 38/16* (2006.01)
*A61K 39/015* (2006.01)
*A61K 39/00* (2006.01)
*A61K 38/00* (2006.01)

(52) U.S. Cl.
CPC ... *A61K 39/0008* (2013.01); *A61K 2039/55516* (2013.01); *A61K 39/015* (2013.01); *A61K 38/00* (2013.01)
USPC ........................................................ 514/21.3

(58) Field of Classification Search
None
See application file for complete search history.

(56) References Cited

U.S. PATENT DOCUMENTS 5,766,899 A * 6/1998 Kuo et al. .................... 435/472

OTHER PUBLICATIONS

Shen et al (Medical Hypotheses, 70:760-764, 2008).*
Wynn, Journal of Pathology, 214:199-210, 2008.*
Von Baehr, Gut, 47(2):281 abstract only, 2000.*
Siegmund et al (Digestive disease, 23(3-4):264, abstract, 2006).*
Ikejima et al. Journal of Gastoenterology and Hepatology 22(suppl 1.) S87, abstract 2007.*
Marra et al, Journal of Clinical Investigation, 92(4):1674, abstract only, 1993.*
Warner et al, Clinical Science, 113(3-4):109 abstract only, 2007.*
Tilg et al (Nature Clinical Practice Gastroenterology and Hepatology, 4(1):24 abstract only, 2007).*
Mishra et al (Current Drug Discovery Technologies 4(2):133, abstract, 2007).*
Kun et al, Critical Reviews in Therapeutic Drug Carrier Systems, 24(2):93, abstract only, 2007.*
Vollmer et al, Journal of Pathology, 189(1):85, abstract only, 1999.*
Cubero, F.J. et al (2006) Rev Esp Enferm Dig (Madrid) vol. 98 N.° 6, pp. 460-472.
Kolios, George et al (2006) World Journal of Gastroenterology 12(46):7413-7420.
Roberts, Ruth A. et al (2007) Toxicological Sciences 96(1):2-15.
Schümann, Jens et al (2000) Amer Journal of Pathology vol. 157, No. 5.
Vrba, Jiff et al (2002) Biomed Papers 146(2):15-20.
Ancsin, JB et al (2004) Exp Parasitol 85:168-182 s.
Aronoff, DM et al (2005) J. Immunol 174:595-599.
Baer, K. et al (2006) Parasitology 86:231-242.
Baeuerle, PA et al (1986) Biochem Biophys Res Comm 141:870-877.
Bouwens, J. et al (1992) Hepatology 5:683-692.
Cerami, C. et al (1992) Cell 70:1021-1033.
Chini, EN et al (1997) Kidney Int 52:917-925.
Danforth, HD et al (1980) Hepatology 33:1154-1165.
Frevert, U. et al (1993) J Exp Med 177:1287-1298.
Frevert, U et al (2005) PLoS Biol 3:e192.
Frevert, U et al (2006) Cell Microbiol 8(10:1537-1546.
Hahn, PY et al (1998) Biochem Biophys Acta 1404:377-384 •.
Hollingdale, MR (1985) Hepatology 5:327-335.
Ishino, T. et al (2004) PLoS Biol 3:e192.
Ishino, T. et at (2004) PLoS Biol 2:E4.
Krawisz, JE et al (1985) Gastroenterology 47:1344-1350.
Mann, VH et al (1994) Mol Biochem Parasitol Nov; 68(1):45-52.
Mauël, J (1996) Adv Parasitol 38:1-51.
Marshall, P. et al (2000) Mol Biochem Parasitol 106:293-298.
Meis, JFGM et al (1983) Parasitology 86:231-242.
Meis, JFGM et al (1985) Z Parasitenkd 71:473-483.
Moestrup, SK et al (1992) Tissue Res 269:375-382.
Mota, MM et al (2001) Science 291:141-144.
Pinzon-Ortiz, C. et al. (2001) J Biol Chem 276:26784-26791.
Pradel, G. et al (2001) Hepatology 33:1154-1165.
Pradel, G et al (2002) Mol Microbiol 45:637-651.
Pradel, G. et al (2004) Comp Hepatol 3 Suppl 1:S47.
Rossi, AG et al (1998) J. Immunol 160:3562-3568.
Shakibaei, M. et at (1996) J Exp Med 184:1699-1711.
Shin, SCJ et al (1982) J. Protozool 29:448-454.
Sionov, RV et al (1990) Int. Immunol 2: 291-301.
Smith, JE et al (1986) Parasitology 93:33-38.
Steers, N. et al (2005) Eur J Immunol 35:2335-2346.
Vanderberg, JP et al (2004) Int. J. Parasitol 34:991-996.
Victorov, AV et al (1995) Biochem Biophys Res Commun 215:691-697.
Ying, P (1997) J Exp Med 184:1699-1711.
Zuckerman et al (1994) J Med Chem 37:2678.
Cerami et al (1992) The Basolateral Domain of the Hepatocyte Plasma Membrane Bears Receptors of the Circumsporozoite Protein of *Plasmodium falciparum* Sporozoites Cell 70:1021-1033.
Frevert, U. et al (1993) Malaria Circumsporozoite Protein Binds to Heparan Sulfate Proteoglycans Associated with the Surface Membrane of Hepatocytes, J. Exp Med 177:1287-1298.

(Continued)

*Primary Examiner* — Patricia A Duffy
(74) *Attorney, Agent, or Firm* — Klauber & Jackson LLC

(57) ABSTRACT

Methods are provided for reducing the activity or function of an inflammatory cell by contacting a cell with, or administering to a subject in need thereof, an effective amount of a circumsporozoite protein or homolog thereof, or a fragment thereof. Methods of treating an inflammatory disease, or an autoimmune disease or for inducing tolerance are also disclosed as are pharmaceutical compositions comprising a therapeutically effective amount of a circumsporozoite protein or homolog thereof, or a fragment thereof and a pharmaceutically acceptable carrier.

11 Claims, 18 Drawing Sheets

(56) References Cited

OTHER PUBLICATIONS

Shakibaei, M. et al (1996) Dual Interaction of the Malaria Circumsporozoite Protein with the Low Density Lipoprotein Receptor-Related Protein (LRP) and Heparan Sulfate Proteoglycans, J. Exp. Med. 184:1699-1711.

Frevert, U. et al (1998) Malaria Circumsporozoite Protein Inhibits Protein Synthesis in Mammalian Cells, EMBO J. 17:3816-3826.

Frevert, U. (1999) Heparan Sulfate and RNA-Binding Motifs in the Malaria Circumsporozoite Protein, Biochem Soc Trans 27:482-487.

Adachi, Y. et al (1994) Inactivation of Kupffer Cells Prevents Early Alcohol-Induced Liver Injury, Hepatology 20:453-460.

Wheeler M.D. et al (2001)The Role of Kupffer Cell Oxidant Production in Early Ethanol-Induced Liver Disease, Free Radical Biology and Medicine 31:1544-1549.

Wheeler, M.D. (2003) Endotoxin and Kupffer Cell Activation in Alcoholic Liver Disease, Alcohol Research and Health 27:300-306.

Cubero, F.J. et al (2006) Kupffer Cells and Alcoholic Liver Disease, Rev Esp Enferm Dig 98:460-472.

Roberts, R.A. et al (2007) Role of the Kupffer Cell in Mediating Hepatic Toxicity and Carcinogenesis, Toxicological Sciences 96:2-15.

Kishore, R. et al (2002) ERK1/2 and Egr-1 Contribute to Increased TNF-$\alpha$ Production in Rat Kupffer Cells After Chronic Ethanol Feeding, Am J. Physiol Gastrointest Liver Physiol 282:G6-G15.

Nagy, L. E. (2003) Recent Insights into the Role of the Innate Immune System in the Development of Alcoholic Liver Disease, Exp Biol Med (Maywood) 228:882-890.

Nanji, A.A. et al (2003) Curcumin Prevents Alcohol-Induced Liver Disease in Rats by Inhibiting the Expresssion of NF-$\kappa$B-Dependent Genes, Am J Physiol Gastrointest Liver Physiol 284:G321-G327.

Cao, Q. et al (2002) Dilinoleoylphosphatidylcholine Decreases LPS-induced TNF-$\alpha$ Generation in Kupffer Cells of Ethanol-Fed Rats; Respective Roles of MAPKs and NF-$\kappa$B, Biochem Biophys Res Commun 294:849-853.

\* cited by examiner

Figure 9

Structure of the *Plasmodium* Circumsporozoite Protein

| | R I | Repeats | | R II-plus | |
|---|---|---|---|---|---|
| | | | SEQ. ID. NO. | | SEQ. ID. NO. |
| P. falciparum | DKRDGNNEDNEKLRKPKHK | KLKQP | 21 | EWSPCSVTCGNGIQVRIKP | 31 |
| P. vivax | DAKKKDGKKAEPKNPREN | KLKQP | 22 | EWTPCSVTCGVGVRVRSRV | 32 |
| P. simium | DAKKKDGKKAEPKNPREN | KLKQP | 23 | EWTPCSVTCGVGVRVRRRV | 33 |
| P. knowlesi | KKKEKGKEKEEEPKKPNEN | KLKQP | 24 | QWTPCSVTCGNGVRIRRKA | 34 |
| P. cynomolgi | DKPKKKDEKQVEPKKPREN | KLKQP | 25 | EWSPCSVTCGKGVRMRRKV | 35 |
| P. brasilianum | KDGNVTNERKKKPTKAVEN | KLKQP | 26 | EWSPCSVTCGSGIRARRKV | 36 |
| P. malariae | KDGNVTNERKKKPTKAVEN | KLKQP | 27 | EWSPCSVTCGSGIRARRKV | 37 |
| P. berghei | DAPEGKKNEKIERNN | KLKQP | 28 | QWSQCNVTCGSGIRVRKRK | 38 |
| P. yoelii | NKDAPKEEKKADPPKEAQN | KLKQP | 29 | EWSQCSVTCGSGVRVRKRK | 39 |
| P. gallinaceum | GNVNRANDRNIPYFRENVV | NLNQP | 30 | EWTNCNVTCGKGIQAKIKS | 40 |
| TRAP | | | | EWSPCSVTCGKGTRSRKR | 41 |
| Thrombospondin | | | | EWTSCSVTCGNGIQQRGR | 42 |
| | | | | PWSSCGVTCGDGVITRIR | 43 |
| | | | | PWDICSVTCGDGVITRIR | 44 |
| Properdin | | | | PWSPCSVTCSEGSQRHRR | 45 |
| | | | | PWGPCSVTCSKGTQIRQR | 46 |
| | | | | PLSPCSVTCGLGQTLEQR | 47 |
| F-spondin | | | | SPWSCSVTCGKGMRTRQR | 48 |

US 8,865,657 B2

COMPOSITIONS AND METHODS FOR INACTIVATING OR SUPPRESSING INFLAMMATORY CELLS

CROSS-REFERENCE TO RELATED APPLICATIONS

The present application is a non-provisional application claiming the priority of copending provisional application Ser. No. 60/709,522, filed Aug. 19, 2005, the disclosure of which is incorporated by reference herein in its entirety. Applicants claim the benefits of this application under 35 U.S.C. §119 (e).

GOVERNMENT RIGHTS CLAUSE

The research leading to the present invention was supported by National Institutes of Health Grant No. AI51656. Accordingly, the Government has certain rights in the invention.

FIELD OF THE INVENTION

The present invention is directed to methods and pharmaceutical compositions for suppressing or inactivating inflammatory cells. More particularly, the invention provides for treating a mammal suffering from an inflammatory disease characterized in part by the presence of inflammatory cells, including macrophages, monocytes, neutrophils or Kupffer cells, by administering an isolated and/or purified circumsporozoite protein (CSP) from the malaria parasite, or fragments, homologs or mimics thereof. Methods are disclosed for inducing tolerance to an antigen, including an autoantigen, an alloantigen or a transplantation antigen by administering the antigen in conjunction with a circumsporozoite protein or homolog, mimic or fragment thereof. Methods of screening for novel compounds that inactivate or suppress inflammatory cell activity or function are also disclosed.

BACKGROUND OF THE INVENTION

Malaria is a disease that continues to have an impact in much of the developing world. This disease, which afflicts 200-300 million people, results in considerable morbidity (eg. fever and chills, malaise, anorexia, kidney disease and brain disease) and kills over one million children each year. The intracellular protozoa, *Plasmodium falciparum*, is the most virulent of human malarias and accounts for greater than 95% of malarial deaths. High levels of parasites in the bloodstream, seen especially in the *P. falciparum* infection, causes serious complications including severe hemolytic anemia, renal failure, and coma.

Minutes after entering a cutaneous blood capillary at the mosquito bite site (Vanderberg J P, Frevert U (2004) Intravital microscopy demonstrating antibody-mediated immobilization of *Plasmodium berghei* sporozoites injected into skin by mosquitoes. Int J Parasitol 34: 991-996), malaria sporozoites are arrested in the liver (Hollingdale M R (1985) Malaria and the liver. Hepatology 5: 327-335; Shin S C J, Vanderberg J P, Terzakis J A (1982) Direct infection of hepatocytes by sporozoites of *Plasmodium berghei*. J Protozool 29: 448-454). To infect a hepatocyte, their initial target cell in the mammalian host (FIG. 1), sporozoites must cross the layer of sinusoidal cells composed of specialized, highly fenestrated sinusoidal endothelia interspersed with Kupffer cells, the resident macrophages of the liver (Wisse E, Zanger R B, Charels K, Smissen P, McCuskey R S (1985) The liver sieve: considerations concerning the structure and function of endothelial fenestrae, the sinusoidal wall and the space of Disse. Hepatology 5: 683-692,4; Bouwens L, Wisse E (1992) The origin of Kupffer cells and their relationship to hepatocytes. In: Billiar T R, Curran R D, editors. Hepatocyte and Kupffer Cell Interactions. Boca Raton: CRC Press. pp. 3-21). Various in vivo, in vitro and, more recently, intravital studies have provided evidence that sporozoites cross the sinusoidal barrier by passing through Kupffer cells, which they selectively recognize and actively invade (Pradel G, Frevert U (2001) *Plasmodium* sporozoites actively enter and pass through Kupffer cells prior to hepatocyte invasion. Hepatology 33: 1154-1165; Pradel G, Garapaty S, Frevert U (2002) Proteoglycans mediate malaria sporozoite targeting to the liver. Mol Microbiol 45: 637-651; Frevert U, Engelmann S, Zougbédé S, Stange J, Ng B, et al. (2005) Intravital observation of *Plasmodium berghei* sporozoite infection of the liver. PLoS Biol 3: e192; Ishino T, Chinzei H, Yuda M (2004) A *Plasmodium* sporozoite protein with a membrane attack complex domain is required for breaching the liver sinusoidal cell layer prior to hepatocyte infection. Cell Microbiol 2: E4; Ishino T, Yano K, Chinzei Y, Yuda M (2004) Cell-passage activity is required for the malarial parasite to cross the liver sinusoidal cell layer. PLoS Biol 2: E4; Meis J F G M, Verhave J P, Brouwer A, Meuwissen J H E T (1985) Electron microscopic studies on the interaction of rat Kupffer cells and *Plasmodium berghei* sporozoites. Z Parasitenkd 71: 473-483; Meis J F G M, Verhave J P, Jap P H K, Meuwissen J H E T (1983) An ultrastructural study on the role of Kupffer cells in the process of infection by *Plasmodium berghei* sporozoites in rats. Parasitology 86: 231-242).

According to our current model (FIG. 1), the initial arrest of the parasites in the liver sinusoid is mediated by heparin-like heparan sulfate proteoglycans (HSPGs) of the liver (Cerami C, Frevert U, Sinnis P, Takacs B, Clavijo P, et al. (1992) The basolateral domain of the hepatocyte plasma membrane bears receptors for the circumsporozoite protein of *Plasmodium falciparum* sporozoites. Cell 70: 1021-1033; Frevert U, Sinnis P, Cerami C, Shreffler W, Takacs B, et al. (1993) Malaria circumsporozoite protein binds to heparan sulfate proteoglycans associated with the surface membrane of hepatocytes. (J Exp Med 177: 1287-1298). More particularly, sporozoites are initially arrested in the liver by binding with their two major surface proteins, the circumsporozoite protein (CSP) and the thrombospondin-related adhesive protein (TRAP), to unique extracellular matrix proteoglycans of the liver (Lyon M, Denkin J A, Gallagher J T (1994) Liver heparan sulfate structure. A novel molecular design. J Biol Chem 269: 11208-11215; Pradel G, Garapaty S, Frevert U (2002) Proteoglycans mediate malaria sporozoite targeting to the liver. Mol Microbiol 45: 637-651; Robson K J H, Frevert U, Reckmann I, Cowan G, Beier J, et al. (1995) Thrombospondin related adhesive protein (TRAP) of *Plasmodium falciparum*: expression during sporozoite ontogeny and binding to human hepatocytes. EMBO J 14: 3883-3894; Pradel G, Garapaty S, Frevert U (2004) Kupffer and stellate cell proteoglycans mediate malaria sporozoite targeting to the liver. Comp Hepatol 3 Suppl 1: S47; Gressner A M, Schäfer S (1989) Comparison of sulphated glycosaminoglycan and hyaluronate synthesis and secretion in cultured hepatocytes, fat storing cells, and Kupffer cells. J Clin Chem Clin Biochem 27: 141-149.) The parasites glide along the sinusoid and eventually recognize selected syndecans, small surface proteoglycans, on Kupffer cells, which they actively invade and traverse unharmed (Pradel G, Garapaty S, Frevert U (2002) Proteoglycans mediate malaria sporozoite targeting to the liver. Mol Microbiol 45: 637-651; Pradel G, Frevert U (2001)

Plasmodium sporozoites actively enter and pass through Kupffer cells prior to hepatocyte invasion. Hepatology 33: 1154-1165; Frevert U, Engelmann S, Zougbédé S, Stange J, Ng B, et al. (2005) Intravital observation of *Plasmodium berghei* sporozoite infection of the liver. PLoS Biol 3: e192; Ishino T, Yano K, Chinzei Y, Yuda M (2004) Cell-passage activity is required for the malarial parasite to cross the liver sinusoidal cell layer. PLoS Biol 2: E4; Meis J F G M, Verhave J P, Brouwer A, Meuwissen J H E T (1985) Electron microscopic studies on the interaction of rat Kupffer cells and *Plasmodium berghei* sporozoites. Z Parasitenkd 71: 473-483; Meis J F G M, Verhave J P, Jap P H K, Meuwissen J H E T (1983) An ultrastructural study on the role of Kupffer cells in the process of infection by *Plasmodium berghei* sporozoites in rats. Parasitology 86: 231-242; Baer K, Roosevelt M, Van Rooijen N, Clarkson Jr. A B, Frevert U (2006) Kupffer cells are obligatory for *Plasmodium* sporozoite infection of the liver. Cell Microbiol in press; Frevert, U. et al. (2006), Nomadic or sessile: can Kupffer cells function as portals for malaria sporozoites to the liver? Cell. Microbiol. In Press; Frevert, U. et al., (2006), Penetrating biological barriers. Liver: *Plasmodium* Sporozoite Passage across the Sinusoidal Cell layer. In: Soldati D, Burleigh, B A, editors. Molecular Mechanisms of Parasite Invasion: Landes, In Press.). After exiting Kupffer cells towards the space of Disse, sporozoites traverse several hepatocytes before eventually settling down for development to thousands of erythrocytes-infective merozoites (Frevert U, Engelmann S, Zougbédé S, Stange J, Ng B, et al. (2005) Intravital observation of *Plasmodium berghei* sporozoite infection of the liver. PLoS Biol 3: e192; Mota M M, Pradel G, Vanderberg J P, Hafalla J C R, Frevert U, et al. (2001) Migration of *Plasmodium* sporozoites through cells before infection. Science 291: 141-144).

Liver heparan sulfate is unique in that its degree of sulfation approaches that of heparin, i.e. markedly higher than that of heparan sulfate from any other tissue (Lyon M, Denkin J A, Gallagher J T (1994) Liver heparan sulfate structure. A novel molecular design. J Biol Chem 269: 11208-11215). More specifically, sporozoites express two major surface proteins, the circumsporozoite protein (CSP) and the thrombospondin-related adhesive protein (TRAP), and these are thought to recognize extracellular matrix (ECM) proteoglycans inside the space of Disse (Pradel G, Garapaty S, Frevert U (2002) Proteoglycans mediate malaria sporozoite targeting to the liver. Mol Microbiol 45: 637-651; Robson K J H, Frevert U, Reckmann I, Cowan G, Beier J, et al. (1995) Thrombospondin related adhesive protein (TRAP) of *Plasmodium falciparum*: expression during sporozoite ontogeny and binding to human hepatocytes. EMBO J 14: 3883-3894; Pradel G, Garapaty S, Frevert U (2004) Kupffer and stellate cell proteoglycans mediate malaria sporozoite targeting to the liver. Comp Hepatol 3 Suppl 1: S47; Gressner A M, Schäfer S (1989) Comparison of sulphated glycosaminoglycan and hyaluronate synthesis and secretion in cultured hepatocytes, fat storing cells, and Kupffer cells. J Clin Chem Clin Biochem 27: 141-149). The large ECM proteoglycans are thought to protrude from the space of Disse through the endothelial sieve plates into sinusoidal lumen (Pradel G, Garapaty S, Frevert U (2004) Kupffer and stellate cell proteoglycans mediate malaria sporozoite targeting to the liver. Comp Hepatol 3 Suppl 1: S47), where they provide a basis for sporozoites to glide along the sinusoidal endothelium. When the parasites encounter a Kupffer cell, CSP binds to selected chondroitin sulfate and heparan sulfate proteoglycans (syndecans) on the cell surface in a multivalent interaction that is thought to contribute to sporozoite adhesion to these macrophages (Pradel G, Garapaty S, Frevert U (2002) Proteoglycans mediate malaria sporozoite targeting to the liver. Mol Microbiol 45: 637-651). After exiting Kupffer cells towards the space of Disse (FIG. 1), sporozoites recognize small cell surface HSPGs on hepatocytes (Frevert U, Sinnis P, Cerami C, Shreffler W, Takacs B, et al. (1993) Malaria circumsporozoite protein binds to heparan sulfate proteoglycans associated with the surface membrane of hepatocytes. J Exp Med 177: 1287-1298; Pinzon-Ortiz C, Friedman J, Esko J, Sinnis P (2001) The binding of the circumsporozoite protein to cell surface heparan sulfate proteoglycans is required for *Plasmodium* sporozoite attachment to target cells. J Biol Chem 276: 26784-26791). This model is supported by direct observations of *P. berghei* sporozoite infection of the livers of live mice (Frevert U, Engelmann S, Zougbédé S, Stange J, Ng B, et al. (2005) Intravital observation of *Plasmodium berghei* sporozoite infection of the liver. PLoS Biol 3: e192).

CSP binding to the surface of mammalian cells (Shakibaei M, Frevert U (1996) Dual interaction of the malaria circumsporozoite protein with the low density lipoprotein receptor-related protein (LRP) and cell surface heparan sulfate. J Exp Med 184: 1699-1711; Ying P, Shakibaei M, Patankar M S, Clavijo P, Beavis R C, et al. (1997) The malaria circumsporozoite protein: interaction of the conserved regions I and II-plus with heparin-like oligosaccharides in heparan sulfate. Exp Parasitol 85: 168-182; Ancsin J B, Kisilevsky R (2004) A binding site for highly sulfated heparan sulfate is identified in the amino-terminus of the circumsporozoite protein: Significance for malarial sporozoite attachment to hepatocytes. J Biol Chem 279: 21824-21832; Rathore D, Kumar S, Lanar D E, McCutchan T F (2001) Disruption of disulfide linkages of the *Plasmodium falciparum* circumsporozoite protein: effects on cytotoxic and antibody responses in mice. Mol Biochem Parasitol 118: 75-82; Rathore D, McCutchan T F (2000) Heparin can regulate the binding of *Plasmodium falciparum* circumsporozoite protein. Mol Biochem Parasitol 108: 253-256; Rathore D, McCutchan T F, Garboczi D N, Toida T, Hernaiz M J, et al. (2001) Direct measurement of the interactions of glycosaminoglycans and a heparin decasaccharide with the malaria circumsporozoite protein. Biochemistry 40: 11518-11524) is mediated by a dual interaction with 1) syndecans, a family of small transmembrane proteoglycans that are expressed on almost all cell types (Bernfield M, Kokenyesi R, Kato M, Hinkes M T, Spring J, et al. (1992) Biology of the syndecans: a family of transmembrane heparan sulfate proteoglycans. AnnRevCell Biol 8: 365-393), and 2) the low density lipoprotein receptor-related protein (LRP-1), a multifunctional scavenger receptor that is predominantly expressed in the liver (Strickland D K, Kounnas M Z, Argraves W S (1995) LDL receptor-related protein: a multiligand receptor for lipoprotein and proteinase catabolism. FASEB J 9: 890-897; Strickland D K, Kounnas M Z, Williams S E, Argraves W S (1994) LDL receptor-related protein (LRP): a multiligand receptor. Fibrinolysis 8, Suppl.: 204-215; Herz J (1993) The LDL-receptor-related protein—portrait of a multifunctional receptor. Curr Opin Lipidol 4: 107-113). LRP-1, also known as the $\alpha_2$-macroglobulin receptor ($\alpha_2$MR) or CD91, is responsible for the clearance from the blood of a large number of molecules, including activated alpha-2-macroglobulin ($\alpha_2$M*), proteases and their complexes with inhibitors, matrix proteins, and growth factors, as well as small particles such as lipoprotein remnants (Strickland D K, Kounnas M Z, Argraves W S (1995) LDL receptor-related protein: a multiligand receptor for lipoprotein and proteinase catabolism. FASEB J 9: 890-897; Strickland D K, Kounnas M Z, Williams S E, Argraves W S (1994) LDL receptor-related protein (LRP): a multiligand receptor. Fibrinolysis 8, Suppl.: 204-215; Herz J (1993) The LDLreceptor-related protein—portrait of a multifunctional receptor. Curr Opin Lipidol 4: 107-113). Both syndecans and LRP-1 induce intracellular signaling cascades. Depending on the cytoplasmic domain of their various core proteins, syndecans are involved in distinct, but overlapping signal transduction cascades (Carey D J (1997) Syndecans: multifunctional cell-surface co-receptors. Biochem J 327: 1-16; Rapraeger A C (2000) Syndecan-regulated receptor signaling. JCell Biol 149: 995-997; Rapraeger A C (2001) Molecular interactions of syndecans during development. SemCell DevBiol 12: 107-116; Rapraeger A C, Ott V L (1998) Molecular interactions of the syndecan core proteins. Curr Op Cell Biol 10: 620-628; Woods A, Couchman J R (1998) Syndecans: synergistic activators of cell adhesion. Trends Cell Biol 8: 189-193; Woods A, Oh E-S, Couchman J R (1998) Syndecan proteoglycans and cell adhesion. Matrix Biology 17: 477-483; Zimmermann P, David G (1999) The syndecans, tuners of transmembrane signaling. FASEB J 13 (Suppl.): S91-S100). LRP-1 is directly or indirectly responsible for a large variety of signal transduction events. A direct role of LRP-1 in signal transduction is supported by the finding that receptor ligation leads to tyrosine and serine phosphorylation of its cytoplasmic domain (LiY, van Kerkhof P, Marzolo M P, Strous G J, Bu G (2001) Identification of a major cyclic AMP-dependent protein kinase A phosphorylation site within the cytoplasmic tail of the low-density lipoprotein receptor-related protein: implication for receptor-mediated endocytosis. Mol Cell Biol 21: 1185-1195; Barnes H, Larsen B, Tyers M, van Der Geer P (2001) Tyrosine-phosphorylated low density lipoprotein receptor-related protein 1 (Lrp1) associates with the adaptor protein SHC in SRC-transformed cells. J Biol Chem 276: 19119-19125; van der Geer P (2002) Phosphorylation of LRP1: regulation of transport and signal transduction. Trends Cardiovasc Med 12: 160-165; Bu G, Sun Y, Schwartz A L, Holtzman D M (1998) Nerve growth factor induces rapid increases in functional cell surface low density lipoprotein receptor-related protein. J Biol Chem 273: 13359-13365) and that signaling adapter proteins such as Shc, Disabled, and FE65 associate with the NPXY motifs in the cytoplasmic domain (Barnes H, Larsen B, Tyers M, van Der Geer P (2001) Tyrosine-phosphorylated low density lipoprotein receptor-related protein 1 (Lrp1) associates with the adaptor protein SHC in SRC-transformed cells. J Biol Chem 276: 19119-19125, Gotthardt M, Trommsdorff M, Nevitt M F, Shelton J, Richardson J A, et al. (2000) Interactions of the low density lipoprotein receptor gene family with cytosolic adaptor and scaffold proteins suggest diverse biological functions in cellular communication and signal transduction. J Biol Chem 275: 25616-25624; Boucher P, Liu P, Gotthardt M, Hiesberger T, Anderson R G, et al. (2002) Platelet-derived growth factor mediates tyrosine phosphorylation of the cytoplasmic domain of the low density lipoprotein receptor-related protein in caveolae. J Biol Chem 277: 15507-15513; Bacskai B J, Xia M Q, Strickland D K, Rebeck G W, Hyman B T (2000) The endocytic receptor protein LRP also mediates neuronal calcium signaling via N-methyl-D-aspartate receptors. ProcNatlAcadSciUSA 97: 11551-11556; Trommsdorff M, Borg J P, Margolis B, Herz J (1998) Interaction of cytosolic adaptor proteins with neuronal apolipoprotein E receptors and the amyloid precursor protein. J Biol Chem 273: 33556-33560). Direct LRP-1 signaling can be inhibited by the receptor-associated protein (RAP) and occurs via the MEKK/JNK/cJun pathway (Lutz C, Nimpf J, Jenny M, Boecklinger K, Enzinger C, et al. (2002) Evidence of functional modulation of the MEKK/JNK/cJun signaling cascade by the low density lipoprotein receptor-related protein (LRP). J Biol Chem 277: 43143-43151; Schneider W J, Nimpf J (2003) LDL receptor relatives at the crossroad of endocytosis and signaling. Cell Mol Life Sci 60: 892-903).

A well-documented example for an indirect role of LRP-1 in signal transduction is its cooperation with the alpha-2-macroglobulin ($\alpha_2$M) signaling receptor ($\alpha_2$MSR) on peritoneal macrophages (Misra U K, Chu C T, Rubenstein D S, Gawdi D S, Pizzo S V (1993) Receptor-recognized a2-macroglobulin-methylamine elevates intracellular calcium, inositol phosphates and cyclic AMP in murine peritoneal macrophages. BiochemJ 290: 885-891; Misra U K, Chu C T-C, Gawdi G, Pizzo S V (1994) The relationship between low density lipoprotein-related/a2-macroglobulin (a2M) receptors and the newly described a2M signaling receptor. JBiolChem 269: 18303-18306; Misra U K, Chu C T-C, Gawdi G, Pizzo S V (1994) Evidence for second a2-macroglobulin receptor. JBiolChem 269: 12541-12547; Misra U K, Gawdi G, Pizzo S V (1999) Ligation of low-density lipoprotein receptor-related protein with antibodies elevates intracellular calcium and inositol 1,4,5-trisphosphate in macrophages. ArchBiochemBiophys 372: 238-247). The $\alpha_2$MSR, which binds activated $\alpha_2$M ($\alpha_2$M*) exclusively and with a much higher affinity than LRP-1, was recently identified as the heat shock protein Grp78 (Misra U K, Akabani G, Pizzo S V (2002) The role of cAMP-dependent signaling in receptor-recognized forms of alpha 2-macroglobulin-induced cellular proliferation. J Biol Chem 277: 36509-36520). Signaling through Grp78 is not inhibited by high molar excess of RAP, but it requires the presence of LRP-1 on the cell surface (Bacskai B J, Xia M Q, Strickland D K, Rebeck G W, Hyman B T (2000) The endocytic receptor protein LRP also mediates neuronal calcium signaling via N-methyl-D-aspartate receptors. ProcNatlAcadSciUSA 97: 11551-11556). Upon ligation with $\alpha_2$M*, the $\alpha_2$MSR activates a pertussis toxin-insensitive phospholipase C (PLC), which hydrolyses membrane phospholipids and generates the two second messengers inositol 1,4,5-triphosphate ($IP_3$) and diacylglycerol (DAG). $IP_3$ causes the release of $Ca^{++}$ from the endoplasmic reticulum, which triggers several $Ca^{++}$-dependent signaling cascades. DAG activates protein kinase C (PKC), which causes phosphorylation-dependent signal transduction via $p21^{Ras}$-dependent MAPK and phosphoinositol 3-kinase (PI3-kinase), leading to DNA synthesis and mitogenesis (Misra U K, Pizzo S V (1998) Ligation of the a2M signaling receptor with receptor-recognized forms of a2-macroglobulin initiates protein and DNA synthesis in macrophages: The effect of intracellular calcium. BiochimBiophysActa 1401: 121-128; Misra U K, Pizzo S V (1998) Ligation of the $\alpha$2M signalling receptor elevates the levels of p21Ras-GTP in macrophages. CellSignal 10: 441-445). By signaling via phospholipase $A_2$ ($PLA_2$) activation, $\alpha_2$M* acts like known growth factors, thus explaining its mitogenic effect on macrophages (Misra U K, Gonzalez-Gronow M, Gawdi G, Hart J P, Johnson C E, et al. (2002) The role of Grp 78 in alpha 2-macroglobulin-induced signal transduction. Evidence from RNA interference that the low density lipoprotein receptor-related protein is associated with, but not necessary for, GRP 78-mediated signal transduction. J Biol Chem 277: 42082-42087). In addition, $\alpha_2$M* binding to $\alpha_2$MSR raises the intracellular concentration of cyclic adenosyl mono-phosphate (cAMP) followed by increased phosphorylation of MEK 1/2, ERK 1/2, p38MAPK, and JNK; these events culminate in cell proliferation by elevating the transcription factors nuclear factor κB (NFκB) and cAMP response element-binding protein (CREB) and expression of the proto-oncogenes c-fos and c-myc (Misra U K, Akabani G, Pizzo S V (2002) The role of cAMP-dependent signaling in receptor-recognized forms of alpha 2-macroglobulin-induced cellular proliferation. J Biol Chem 277: 36509-36520; Misra U K, Gonzalez-Gronow M, Gawdi G, Hart J P, Johnson C E, et al. (2002) The role of Grp 78 in alpha 2-macroglobulin-induced signal transduction. Evidence from RNA interference that the low density lipoprotein receptor-related protein is associated with, but not necessary for, GRP 78-mediated signal transduction. J Biol Chem 277: 42082-42087). The binding of other LRP-1 ligands such as lactoferrin, lipoprotein lipase, and *Pseudomonas* exotoxin A to macrophages also increases the intracellular concentration of $Ca^{++}$, cAMP, and IP3, and activates PKA [Misra U K, Chu C T-C, Gawdi G, Pizzo S V (1994) The relationship between low density lipoprotein-related/a2-macroglobulin (a2M) receptors and the newly described α2M signaling receptor. JBiolChem 269: 18303-18306; Misra U K, Chu C T-C, Gawdi G, Pizzo S V (1994) Evidence for second α2-macroglobulin receptor. JBiolChem 269: 12541-12547; Misra U K, Akabani G, Pizzo S V (2002) The role of cAMP-dependent signaling in receptor-recognized forms of alpha 2-macroglobulin-induced cellular proliferation. J Biol Chem 277: 36509-36520; Misra U K, Pizzo S V (1998) Ligation of the α2M signaling receptor with receptor-recognized forms of α2-macroglobulin initiates protein and DNA synthesis in macrophages: The effect of intracellular calcium. BiochimBiophysActa 1401: 121-128, Misra U K, Gonzalez-Gronow M, Gawdi G, Hart J P, Johnson C E, et al. (2002) The role of Grp 78 in alpha 2-macroglobulin-induced signal transduction. Evidence from RNA interference that the low density lipoprotein receptor-related protein is associated with, but not necessary for, GRP 78-mediated signal transduction. J Biol Chem 277: 42082-42087; Misra U K, Pizzo S V (2002) Regulation of cytosolic phospholipase A2 activity in macrophages stimulated with receptor-recognized forms of alpha 2-macroglobulin: role in mitogenesis and cell proliferation. J Biol Chem 277: 4069-4078; Misra U K, Gonzalez-Gronow M, Gawdi G, Pizzo S V (2005) The role of MTJ-1 in cell surface translocation of GRP78, a receptor for alpha 2-macroglobulin-dependent signaling. J Immunol 174: 2092-2097). These LRP-1 ligands, however, signal via a pertussis-sensitive G protein and the exact mechanism of signal induction is unknown.

Kupffer cells are strategically positioned in the sinusoidal lumen and play an important role in the removal of altered self or foreign substances from the blood (Kuiper J, Brouwer A, Knook D L, Berkel T J Cv (1994) Kupffer and sinusoidal endothelial cells. In: Arias I M, Boyer J L, Fausto N, Jakoby W B, Schachter D A et al., editors. The Liver: Biology and Pathobiology. 3 ed. New York: Raven Press, Ltd. pp. 791-818; Gumucio J J, Bilir B M, Moseley R H, Berkowitz C M (1994) The biology of the liver cell plate. In: Arias I M, Boyer J L, Fausto N, Jakoby W B, Schachter D A et al., editors. The Liver: Biology and Pathobiology. 3 ed. New York: Raven Press. pp. 1143-1163). Phagocytosis results in the generation of reactive oxygen species (ROS), which are lethal for many microorganisms (Mauël J (1996) Intracellular survival of protozoan parasites with special reference to *Leishmania* spp., *Toxoplasma gondii* and *Trypanosoma cruzi*. AdvParasitol 38: 1-5). The induction of the formation of reactive oxygen species (ROS) is a complex event that requires the assembly of the heterohexameric NADPH oxidase (Brandes R P, Kreuzer J (2005) Vascular NADPH oxidases: molecular mechanisms of activation. Cardiovasc Res 65: 16-27; Groemping Y, Rittinger K (2005) Activation and assembly of the NADPH oxidase: a structural perspective. Biochem J 386: 401-416; Vignais P V (2002) The superoxide-generating NADPH oxidase: structural aspects and activation mechanism. Cell Mol Life Sci 59: 1428-1459; Lambeth J D (2004) NOX enzymes and the biology of reactive oxygen. Nat Rev Immunol 4: 181-189; Quinn M T, Gauss K A (2004) Structure and regulation of the neutrophil respiratory burst oxidase: comparison with nonphagocyte oxidases. J Leukoc Biol 76: 760-781). Kupffer cells represent more than 80% of the total population of tissue macrophages of the body (Kuiper J, Brouwer A, Knook D L, Berkel T J Cv (1994) Kupffer and sinusoidal endothelial cells. In: Arias I M, Boyer J L, Fausto N, Jakoby W B, Schachter D A et al., editors. The Liver: Biology and Pathobiology. 3 ed. New York: Raven Press, Ltd. pp. 791-818). With their strategic position in the sinusoidal lumen, they play an important role in the removal of altered self or foreign substances as well as pathogenic microorganisms from the blood (Kuiper J, Brouwer A, Knook D L, Berkel T J Cv (1994) Kupffer and sinusoidal endothelial cells. In: Arias I M, Boyer J L, Fausto N, Jakoby W B, Schachter D A et al., editors. The Liver: Biology and Pathobiology. 3 ed. New York: Raven Press, Ltd. pp. 791-818; Gumucio J J, Bilir B M, Moseley R H, Berkowitz C M (1994) The biology of the liver cell plate. In: Arias I M, Boyer J L, Fausto N, Jakoby W B, Schachter D A et al., editors. The Liver: Biology and Pathobiology. 3 ed. New York: Raven Press. pp. 1143-1163). Phagocytosis results in the generation of ROS, which are lethal for many microorganisms (Mauël J (1996) Intracellular survival of protozoan parasites with special reference to *Leishmania* spp., *Toxoplasma gondii* and *Trypanosoma cruzi*. Adv Parasitol 38: 1-51). Surprisingly, however, Kupffer cells and other macrophages do not kill viable malaria sporozoites, even after prolonged co-incubation in vitro (Vanderberg J P, Chew S, Stewart M J (1990) *Plasmodium* sporozoite interactions with macrophages in vitro: a videomicroscopic analysis. J Protozool 37: 528-536; Pradel G, Frevert U (2001) *Plasmodium* sporozoites actively enter and pass through Kupffer cells prior to hepatocyte invasion. Hepatology 33: 1154-1165., Danforth H D, Aikawa M, Cochrane A H, Nussenzweig R S (1980) Sporozoites of mammalian malaria: attachment to, interiorization and fate within macrophages. J Protozool 27: 193-202; Smith J E, Alexander J (1986) Evasion of macrophage microbicidal mechanisms by mature sporozoites of *Plasmodium yoelii yoelii*. Parasitology 93: 33-38).

The present invention has addressed the observations noted above and has led the inventors of the present application to hypothesize that the parasites are able to prevent Kupffer cell activation by inducing intracellular signaling events that suppress macrophage activation. Moreover, the present invention demonstrates that by raising the intracellular cAMP concentration in a process that involves syndecan binding and LRP-1 ligation, malaria sporozoites suppress the respiratory burst in Kupffer cells. The present invention proposes the use of this finding for developing novel strategies and therapeutics for treating inflammatory conditions in which reactive oxygen species may play a role in the disease process or may play a role in developing the symptoms or sequelae associated with the disease.

SUMMARY OF THE INVENTION

In its broadest aspect the present invention relates to the discovery that the circumsporozoite protein (CSP) of *plasmodium* species, and fragments thereof, and homologs of the circumsporozoite protein from other apicomplexan parasites, suppress or deactivate inflammatory cells. More particularly, this protein and fragments thereof and homologs thereof, suppress the respiratory burst of an inflammatory cell, in particular, macrophages such as Kupffer cells of the liver. More particularly, the CSP protein and fragments thereof and homologs thereof, suppress the release of reactive oxygen species or reactive nitrogen species and the phagocytic activity of an inflammatory cell, in particular, macrophages such as Kupffer cells of the liver. Furthermore, the CSP or fragments or homologs thereof also raise the intracellular cAMP and IP3 concentration in inflammatory cells.

Accordingly, a first aspect of the invention provides a method of reducing the activity or function of an inflammatory cell comprising contacting the inflammatory cell with an isolated and substantially purified circumsporozoite protein (CSP) or a fragment thereof.

In one particular embodiment, the biologically active CSP may be obtained from a *plasmodium* species. In another particular embodiment, the biologically active CSP may be produced by recombinant means. In another particular embodiment, the biologically active CSP may be produced synthetically by methods known to those skilled in the art. In yet another particular embodiment, the biologically active molecule may be a variant of a CSP or a fragment thereof. In yet another particular embodiment, the variant has about 90% sequence identity to a naturally occurring CSP. In yet another particular embodiment the variant is isolated from an apicomplexan parasite other than a *plasmodium*. In yet another particular embodiment, the fragment comprises a region II-plus (see FIG. 9 for RII-plus region), or a portion thereof that retains the activity of the full-length CSP protein, in particular, the portion thereof of a CSP should retain the ability to either inhibit the expression, production or release of pro-inflammatory cytokines (such as, but not limited to, IL-6, IL-12, TNF alpha), or to enhance the expression, production or release of anti-inflammatory cytokines (such as, but not limited to IL-10 and TGF-beta), or to inhibit the release of reactive oxygen or nitrogen species from the macrophage or to inhibit the respiratory burst of the macrophage, or to inhibit the phagocytic activity of the macrophage. In yet another particular embodiment, contacting or exposing an inflammatory cell to a sporozoite, or a CSP protein, analogue, variant, derivative or fragment, or combination of any of the foregoing may result in a shift in the ratio of the cytokine profile, more particularly towards the anti-inflammatory cytokines rather than the pro-inflammatory cytokines.

The CSP or a biologically active, recombinant or synthetic circumsporozoite polypeptide or variant thereof, or a fragment of any of the foregoing, raises the intracellular cAMP concentration and the intracellular concentration of inositol-1,4,5-triphosphate ($IP_3$) concentration in the inflammatory cell. The CSP or a biologically active, recombinant or synthetic circumsporozoite polypeptide or variant thereof, or a fragment of any of the foregoing, also inhibits the respiratory burst in the inflammatory cell.

In yet another particular embodiment, the inflammatory cell is a Kupffer cell or an extrahepatic tissue or blood macrophage or a blood cell selected from the group consisting of monocytes, neutrophils, and eosinophils.

A second aspect of the invention provides a method of inducing antigen specific tolerance in vivo comprising administering to a mammal a tolerance inducing amount of CSP, or a biologically active, recombinant or synthetic circumsporozoite polypeptide or variant thereof, or a fragment of any of the foregoing with the antigen against which tolerance is desired. Non-limiting examples of antigens for which tolerance of the immune system is desirable include transplant antigens, allergens, and antigens toward which autoimmunity has or may develop (autoantigens).

In one particular embodiment, the mammal is a human or a non-human mammal. In another particular embodiment, the non-human mammal is selected from the group consisting of horses, goats, sheep, mice, rats, rabbits, dogs, cats, and guinea pigs.

In another particular embodiment, the administering of the CSP, or a biologically active, recombinant or synthetic circumsporozoite polypeptide or variant thereof, or a fragment of any of the foregoing and antigen is accomplished via intravenous injection. In a more particular embodiment, the administering of the CSP or a biologically active, recombinant or synthetic circumsporozoite polypeptide or variant thereof, or a fragment of any of the foregoing and antigen is accomplished directly via the portal vein. In a further particular embodiment, the administering of the CSP, or a biologically active, recombinant or synthetic circumsporozoite polypeptide or variant thereof, or a fragment of any of the foregoing and antigen is accomplished by intravenously injecting inert microspheres carrying covalently linked CSP, or a biologically active, recombinant or synthetic circumsporozoite polypeptide or variant thereof, or a fragment of any of the foregoing on their surface. Such administering results in preferential uptake by Kupffer cells, or by an extrahepatic tissue or blood macrophages or by a blood cell selected from the group consisting of monocytes, neutrophils, and eosinophils.

In another particular embodiment, the antigen is an autoantigen, an alloantigen or a transplantation antigen. In yet another particular embodiment, the autoantigen is selected from the group consisting of myelin basic protein, collagen or fragments thereof, DNA, nuclear and nucleolar proteins, mitochondrial proteins and pancreatic β-cell proteins.

In yet another particular embodiment, the administering may be done with a second agent for maintaining the tolerogenic state. This second agent may be selected from the group consisting of cyclosporin A, rapamycin (sirolimus), tacrolimus (FK-506), anti-lymphocyte globulin, anti-CD3 antibody, anti-CD4 antibody, anti-CD40L, and a corticosteroid.

A third aspect of the invention provides a method for treating, ameliorating or preventing an inflammatory liver disease or disorder in a subject in need thereof by administering a CSP or a fragment thereof. In one particular embodiment, the method provides for the steps of:

a) obtaining an isolated and substantially purified circumsporozoite protein (CSP), or a recombinant CSP or a fragment thereof, or a biologically active, synthetic circumsporozoite polypeptide or variant thereof, or a fragment thereof;
b) administering a CSP, or a fragment thereof in a therapeutically effective amount to a subject in need thereof; and
c) monitoring the subject for a positive therapeutic outcome by measuring blood levels of liver enzymes; wherein a patient suffering from a liver disease or disorder exhibits elevated liver enzymes and wherein treating the subject with a CSP or a fragment thereof results in normalizing liver enzyme levels.

In one particular embodiment, the liver disease is characterized by fibrosis or cirrhosis. In another particular embodiment the liver disease is induced by a viral, parasitic, or a bacterial infection. In another particular embodiment the liver disease is induced by alcohol consumption. In another particular embodiment the liver disease is a result of treatment with a hepatotoxic drug.

In another particular embodiment the liver disease or condition is selected from the group consisting of parasitic infections of the liver, bacterial infections of the liver, fulminant hepatitis, chronic hepatitis, viral hepatitis, alcoholic hepatitis, hepatic fibrosis, liver cirrhosis, hepatic cancer, autoimmune hepatitis, drug allergic hepatopathy and primary biliary cirrhosis. In another particular embodiment, a subject with chronic liver disease is a human with cirrhosis of the liver. In another particular embodiment, a subject with chronic liver disease is a human with fibrosis of the liver. In a specific embodiment, chronic HCV infection is manifested by raised liver enzymes (e.g., ALT, AST), persistent (e.g., greater than six months) HCV RNA levels, and/or histological evidence of liver damage, fibrosis, and/or cirrhosis.

In another particular embodiment the CSP comprises the amino acid sequence of any one of SEQ ID NOs: 2, 4, 6, 8, 10, 12, 14, 16, 18, or 20. In another particular embodiment, the fragment of the circumsporozoite protein has the amino acid sequence as set forth in SEQ ID NOs: 21-48, preferably 31-48. In another particular embodiment the nucleic acid encoding the CSP comprises the nucleic acid sequence of any one of SEQ ID NOs: 1, 3, 5, 7, 9, 11, 13, 15, 17 or 19.

A fourth aspect of the invention provides a method for preventing or treating inflammation-associated disorders, comprising contacting an inflammatory cell population with an inflammatory cell suppressing amount of an isolated and substantially purified, or a recombinant circumsporozoite protein (CSP) or a fragment thereof, or a biologically active, synthetic circumsporozoite polypeptide or variant, or fragment thereof, thereby preventing or treating the inflammation-associated disorder.

In one particular embodiment, the inflammation-associated disorder is due to an inflammatory disease. In another particular embodiment, the inflammation-associated disorder is selected from the group consisting of arthritis, pain, fever, asthma, bronchitis, vascular disease, nephrotic syndrome, and myocardial ischemia. In another particular embodiment the pain is headache pain or joint pain.

In another particular embodiment, the cell population is also contacted with a second active agent. In a further particular embodiment, the second active agent is selected from the group consisting of: anti-inflammatory agents, matrix metalloprotease inhibitors, lipoxygenase inhibitors, antagonists of cytokines, agents that modify differentiation, agents that modify proliferation, antibacterial agents, antiparasitic agents, antifungal agents, anaesthetics, and antiviral agents.

A fifth aspect of the invention provides for a pharmaceutical composition comprising a therapeutically effective amount of a CSP, or a fragment thereof, and a pharmaceutically acceptable carrier, for treating an inflammatory disease, condition or disorder, or for treating an inflammation-associated condition.

In one particular embodiment, the inflammatory disease or disorder is a liver disease or disorder. In another particular embodiment, the inflammation-associated condition may be selected from the group consisting of arthritis, pain, fever, asthma, bronchitis, vascular disease, nephrotic syndrome, and myocardial ischemia.

In another particular embodiment, the composition comprises a therapeutically effective amount of a CSP having the amino acid sequence of any one of SEQ ID NOs: 2, 4, 6, 8, 10, 12, 14, 16, 18 and 20 or a fragment thereof having the amino acid sequence of any one of SEQ ID NOs: 21-48, preferably 31-48, and a pharmaceutically acceptable carrier.

In another particular embodiment the composition comprises a nucleic acid encoding a CSP, as set forth in SEQ ID NOs: 1, 3, 5, 7, 9, 11, 13, 15, 17, or 19 or a nucleic acid encoding a fragment of a CSP, and a pharmaceutically acceptable carrier.

In another particular embodiment, the pharmaceutical composition is formulated for delivery by a route selected from the group consisting of intravenous delivery, intramuscular delivery, intraperitoneal delivery, subcutaneous delivery, rectal delivery, oral delivery, topical delivery, transdermal delivery, by inhalation, by portal venous delivery and by intravenous delivery of CSP-coated beads.

In certain embodiments, the subject can be receiving concurrently other therapies. In one embodiment, the subject can be a subject who had undergone a regimen of treatment and whose inflammatory disease or condition is regressing. In another embodiment, the subject can be a subject who had undergone a regimen of treatment for such diseases or conditions. The compositions of the invention can be administered adjunctively with any of the conventional treatment modalities, such as but not limited to, other anti-inflammatory therapies or other anti-rejection therapies or immunosuppressant therapies. In one embodiment, the compositions of the invention can be administered to a subject to reduce the probability of relapse after a successful course of treatment.

In certain other embodiments, the subject can be one who has not yet been diagnosed with an inflammatory disease or condition but is predisposed to or at high risk of developing such disease or condition as a result of genetic factors and/or environmental factors. The subject may also be one who displays characteristics that are associated with a high risk of chronic inflammatory diseases or conditions, such as suspect cells in biopsy and/or body fluids (e.g., tissue, blood, serum, cells, plasma).

Other objects and advantages will become apparent from a review of the ensuing detailed description and attendant claims taken in conjunction with the following illustrative drawings. All references cited in the present application are incorporated herein in their entirety.

BRIEF DESCRIPTION OF THE DRAWINGS

FIG. 9. Structure of the *Plasmodium* Circumsporozoite Protein showing the region I and Region II-plus motifs.

DETAILED DESCRIPTION OF THE INVENTION

Figure 1:
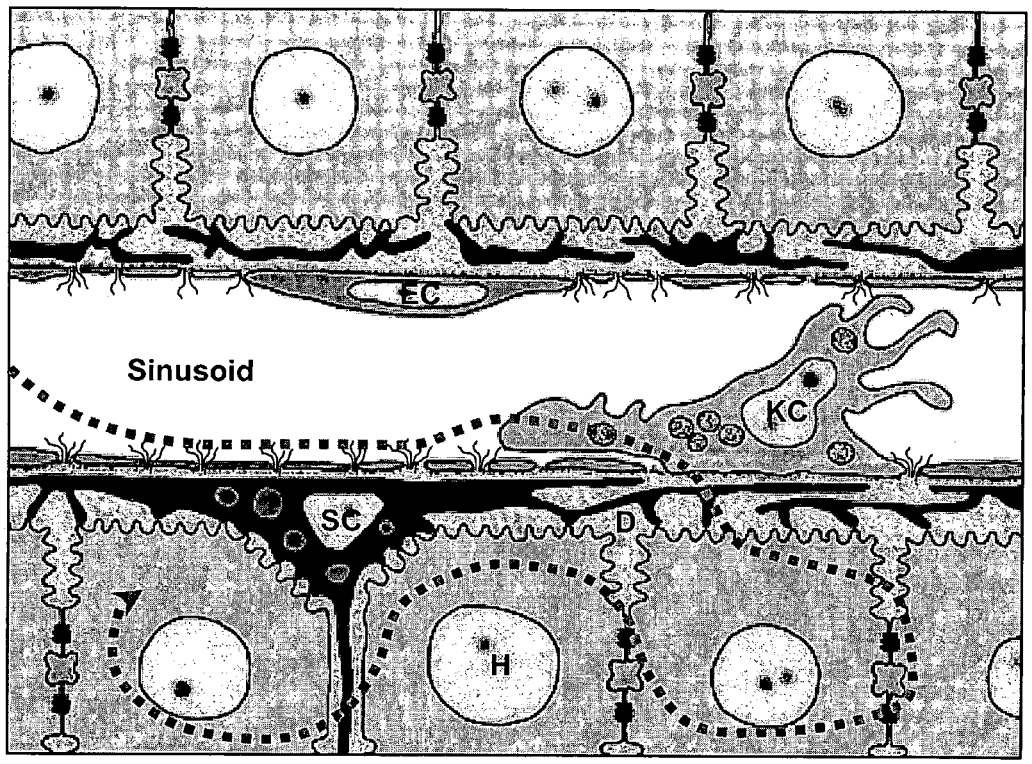
FIG. 1. Model of *Plasmodium* sporozoite infection of the liver. Liver sinusoids are lined with a continuous layer of fenestrated endothelia (EC) and Kupffer cells (KC). Hepatocytes are separated from this sinusoidal cell layer by the space of Disse (D), which contains the loose extracellular matrix of the liver and also harbors stellate cells (SC). Sporozoites traveling in a sinusoid are arrested by binding to stellate cell-derived ECM proteoglycans that are thought to protrude from the space of Disse through the endothelial fenestration into the sinusoid. The parasites glide along the sinusoidal cell layer until they encounter a Kupffer cell. They enter the Kupffer cell by membrane invagination and cross it slowly towards the space of Disse. Sporozoites then continue their journey by migrating through several hepatocytes, wounding them fatally in the process, until they eventually settle down in a final one for differentiation to thousands of merozoites.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, references to "a method" include one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entireties.

Definitions

The terms used herein have the meanings recognized and known to those of skill in the art, however, for convenience and completeness, particular terms and their meanings are set forth below.

"Agent" refers to all materials that may be used to prepare pharmaceutical and diagnostic compositions, or that may be compounds such as small synthetic or naturally derived organic compounds, nucleic acids, polypeptides, antibodies, fragments, isoforms, variants, or other materials that may be used independently for such purposes, all in accordance with the present invention.

As used herein, the term "therapeutically effective amount" refers to that amount of the therapeutic agent sufficient to result in prevention of or treatment of a disease, amelioration of one or more symptoms of a disease, or prevention of advancement of a disease. For example, with respect to the treatment of liver disease, a therapeutically effective amount preferably refers to the amount of a therapeutic agent that reduces the extent of liver disease by at least 10%, preferably at least 20%, at least 30%, at least 40%, at least 50%, at least 60%, at least 70%, at least 80%, at least 90%, or at least 100%. The extent of liver disease can be determined by any method known in the art. The term "therapeutically effective amount" also refers to that amount of the therapeutic, for example, a CSP , or fragment or mimic thereof, sufficient to treat, manage, or ameliorate liver disease, chronic HCV infection or the symptoms or histopathology associated with liver disease, or chronic HCV infection. A therapeutically effective amount may refer to the amount of CSP necessary to reduce the level or extent of cirrhosis, fibrosis, lobular hepatitis, and/or perioportal bridging necrosis, reduce the level of liver enzymes, reduce viral load, improve liver histology, and/or improve quality of life in a subject. A therapeutically effective amount may also refer to the amount of the composition that provides a therapeutic benefit in the treatment or management of the symptoms or histopathology associated with liver disease, or chronic HCV infection. Further, a therapeutically effective amount with respect to the CSP polypeptide, or nucleic acid encoding the CSP polypeptide or a fragment of the CSP polypeptide or a mimic thereof means that amount of the polypeptide or composition comprising the polypeptide alone, or in combination with other therapies, that provides a therapeutic benefit in the treatment, management, or amelioration of a disease, such as liver disease, or chronic HCV infection or the symptoms or histopathology associated with liver disease, or chronic HCV infection. A "therapeutically effective amount" may also refer to the amount of CSP protein or polypeptide, or nucleic acid encoding the polypeptide or fragment or mimic thereof necessary to inhibit the respiratory burst in an inflammatory cell, for example, in a Kupffer cell. A "therapeutically effective amount" may also refer to the amount of CSP protein or polypeptide, or nucleic acid encoding the polypeptide or fragment or mimic thereof necessary to raise the intracellular cAMP or IP3 concentration in an inflammatory cell, such as a liver macrophage (a Kupffer cell).

The terms "treatment", "treating", and the like are used herein to generally mean obtaining a desired pharmacologic and/or physiologic effect. The effect may be prophylactic in terms of completely or partially preventing a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; or (c) relieving the disease or condition, i.e., causing regression of the disease or condition. The population of subjects treated by the method of the disease includes subject suffering from the undesirable condition or disease, as well as subjects at risk for development of the condition or disease. With respect to liver disease or chronic infections of the liver, whether they are due to a bacterial, parasitic or viral infection, the terms "treat," "treating" and "treatment" refer to reducing or eliminating liver disease or chronic infection, respectively, or the symptoms or histopathology associated with liver disease, or chronic infection, respectively. In specific embodiments, the terms encompass the reduction of the extent of cirrhosis, fibrosis, lobular hepatitis, and/or perioportal bridging necrosis, reduction of liver enzymes, reduction of viral load, improvement of liver histology, and/or improvement of quality of life of a subject with liver disease, or chronic infection.

The terms "prevent, preventing, and prevention," as used herein, are intended to refer to a decrease in the occurrence of disease, for example, liver disease. The prevention may be complete, e.g., the total absence of the disease. The prevention may also be partial, such that the amount of disease is less than that which would have occurred without the present invention. For example, the extent of disease using the methods of the present invention may be at least 10%, preferably at least 20%, at least 30%, at least 40%, at least 50%, at least 60%, at least 70%, at least 80%, at least 90%, or at least 100% less than the amount of disease that would have occurred without the present invention.

The term "in conjunction with one or more therapeutic agents," as used herein, is intended to refer to the combined administration of an active CSP and one or more therapeutic agents, wherein the CSP can be administered prior to, concurrently with, or after the administration of the therapeutic agents. The active CSP can be administered up to three months prior to or after the therapeutic agents and still be considered to be treatment in conjunction with the therapeutic agents.

A "small molecule" or "small organic molecule" is an organic compound (or organic compound complexed with an inorganic compound (e.g., metal)) that has a molecular weight of less than 3 kilodaltons, and preferably less than 1.5 kilodaltons. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify compounds that modulate a bioactivity. A "small organic molecule" is an organic compound (or organic compound complexed with an inorganic compound (e.g., metal)) that has a molecular weight of less than 3 kilodaltons, and preferably less than 1.5 kilodaltons, and more preferably less than about 1 kilodalton.

"Subject" or "patient" refers to a mammal, preferably a human, in need of treatment for a condition, disorder or disease.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "inflammatory cell" refers to any cell associated with an inflammatory disease or condition, such as a macrophage, a Kupffer cell, an extrahepatic tissue macrophage, or a blood cell selected from a monocyte, a neutrophil or an eosinophil.

The term "reducing the activity or function an inflammatory cell" as used herein refers to the suppression of any activity or function associated with an inflammatory cell, including, but not limited to, the release of a cytokine, a growth factor, a reactive oxygen or nitrogen species, a free radical, or a respiratory burst. It may also refer to the deactivation of the inflammatory cell as it relates to the cell or tissue damage resulting from the presence of such cells at the site of disease or injury.

"Respiratory burst" refers to the release of reactive oxygen species (eg. superoxide radical and hydrogen peroxide) from different types of cells. Although all cell types can produce reactive oxygen species, usually it denotes the release of these chemicals from immune cells, e.g. macrophages, neutrophils, eosinophils and monocytes as they come into contact with different foreign antigens, such as bacteria, fungi or parasites. The term "free radicals" refers to a chemical species that possesses one or more unpaired electrons in the outer (valence) shell of the molecule. An unpaired electron is an electron that is alone in an orbital. For this reason they are highly reactive and thus have low chemical specificity i.e., they can react with most molecules in their vicinity. This includes proteins, lipids, carbohydrates and DNA. Free radicals attack the nearest stable molecule, thus "stealing" its electron. When the attacked molecule loses its electron, it becomes a free radical itself, thus beginning a chain reaction. It continues until the final result is the disruption of a living cell. Free radicals are produced continuously in cells either as by-products of metabolism or deliberately as in phagocytosis (Cheeseman, K. H. and Slater, T. F., Br Med Bull. July 1993; 49(3): 481-93). Free radicals are broken down into three broad groups: ROS (reactive oxygen species), RNS (reactive nitrogen species), and R (other reactive radicals). Not all reactive oxygen species are free radicals, eg. $H_2O_2$. However, the term "reactive oxygen species" or "ROS" has been introduced to describe collectively not only $O_2$ and OH radicals, but also $H_2O_2$ (a nonradical). "Reactive nitrogen species" or "RNS" refers to molecules such as, but not limited to NO and peroxynitrites. These reactive oxygen and reactive nitrogen species are also known to produce damage to cells and tissues. Oxidative stress occurs when the amount of free radicals in the body exceeds its pool of antioxidants.

The term "tolerance" refers to the specific immunological non-reactivity to an antigen resulting from a previous exposure to the same antigen. While the most important form of tolerance is thought to be non-reactivity to self antigens, it is also possible, and sometimes desirable, to induce tolerance to non-self antigens (alloantigens). Tolerance differs from non-specific immunosuppression and immunodeficiency since it is an active antigen dependent process.

The term "substantially pure" or "substantially purified" means that a compound or agent, such as the CSP or homolog thereof, or fragment thereof, or mimic thereof, has been separated from at least 50% to 70% or more of the components (e.g., non-CSP proteins) that may naturally accompany it. Preferably, a compound or agent of the invention is substantially pure or purified when it is separated from at least about 85 to 90% of the components that naturally accompany it, more preferably at least about 95%, and most preferably about 99%. Normally, purity is measured on a chromatography column, polyacrylamide gel, or by HPLC analysis.

"Microspheres" are particles having an outer membrane comprised of synthetic or natural polymers surrounding an aqueous chamber. They are generally discrete units that do not share membranes when in suspension. Methods of producing microspheres are described, for example, in U.S. Pat. Nos. 5,552,133, 5,310,540, 4,718,433 and 4,572,203; European Patent Publication No. EP 458,745; and PCT Publication No. WO 92/05806.

By "autoantigen" is meant an endogenous antigen that stimulates the production of autoantibodies, as in an autoimmune reaction.

By "alloantigen" is meant an antigen that occurs in some but not other members of the same species. Isoantigen is sometimes used in this sense.

By "transplantation antigen" is meant an antigen present on cells, tissues or organs from a donor that may differ from the antigens present in the cells, tissues or organs of a recipient. Such differences may result in the rejection of the transplant.

By "inflammatory disease, disorder or condition" or "inflammation-associated disease, disorder, or condition" is meant any disease, disorder or condition characterized in part by the presence of or influx of inflammatory cells, such as those described herein. This includes influx of activated lymphocytes such as monocytes, neutrophils, eosinophils, macrophages, T cells and B-cells, into a host tissue that results in damage to the host organism. Examples of inflammatory disease include but are not limited to conditions such as inflammatory bowel disease, sepsis, and rheumatoid arthritis. An "autoimmune disease" broadly refers to an immune disease wherein the immune response is developed against antigens normally present in the affected patient. It can be an organ specific autoimmune disease (the immune response is for example specifically directed against the endocrine system, the hematopoietic system, the skin, the cardiopulmonary system, the neuromuscular system, the central nervous system, etc) or a systemic autoimmune disease (for example, Systemic lupus erythematosous, Rheumatoid arthritis, polymyositis, etc). Multiple sclerosis is considered to be an autoimmune disease that affects the central nervous system.

A "tolerance inducing amount of CSP" refers to an amount of the circumsporozoite protein (CSP), or fragment, homolog or mimic thereof sufficient to induce a state of tolerance to a specific antigen for which immunologic non-responsiveness is desired. The amount of the CSP or fragment, or homolog, or mimic thereof may be determined by techniques known to those skilled in the art.

An "inflammatory cell suppressing amount" refers to an amount of a CSP or fragment, or homolog, or mimic thereof sufficient to suppress any activity or function associated with the presence of an inflammatory cell as defined herein. This may include suppression of migration of the cell, suppression of release or production of a cytokine or growth factor from the cell, suppression of the respiratory burst, or suppression of release of a free radical or reactive oxygen or nitrogen species from the inflammatory cell. It may also refer to the amount of the CSP or fragment or mimic thereof necessary to prevent the cellular or tissue damage resulting from the presence of an inflammatory cell. The amount necessary to suppress the activity or function of an inflammatory cell can be determined by procedures known to those skilled in the art, and more particularly, using the assays and methods described in the Examples. An effective in vitro amount may range from about 10 to 500 nM, more preferably about 20 to 250 nM, and most preferably from about 50 to 100 nM. An effective in vivo amount may range from about 1 mM to about 500 mM, more preferably about 10 mM to about 250 mM and most preferably about 20 mM to about 100 mM. It is to be recognized that the most effective dose can be established using procedures known to those skilled in the art and as described herein. Furthermore, the determination of the most effective doses would also depend on several factors including the cells to be targeted, as well as the route of injection and the disease to be treated.

A "positive therapeutic outcome" refers to either normalization of either a function or activity of a cell, tissue or organ, or normalization of a clinical diagnostic value that is used as a biomarker of disease progression. For example, in the case of a liver disease, a positive therapeutic outcome may be measured by looking for normalization of liver enzymes that are elevated as a result of a liver disease or damage.

The "apicomplexa" are a monophyletic group composed almost entirely of parasitic (ie, no free-living) species. Formerly the apicomplexa were part of a group called sporozoa and this name is still sometimes used. The apicomplexa are an extremely large and diverse group (>5000 named species). Seven species of "apicomplexan parasites" infect humans. These include *Plasmodium, Babesia, Crytosporidium, Isospora, Cyclospora, Sarcocystis*, and *Toxoplasma. Plasmodium*, as the causitive agent of malaria, has the greatest impact on human health. *Babesia* is a relatively rare zoonotic infection. The other five species are all classified as *coccidia*. The *coccidia* are generally considered opportunistic pathogens and are often associated with AIDS. Several apicomplexan parasites are also important in terms of veterinary medicine and agriculture. Most notable are *Babesia* and *Theileria* in cattle and *Eimeria* in poultry.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5N to 3N direction along the nontranscribed strand of DNA (i.e., the strand having a sequence homologous to the mRNA). A "recombinant DNA molecule" is a DNA molecule that has undergone a molecular biological manipulation.

Two DNA sequences are "substantially homologous" or "substantially similar" when at least about 50% (preferably at least about 75%, and most preferably at least about 90, or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al.; DNA Cloning, Vols. I & II; Nucleic Acid Hybridization.

Similarly, two amino acid sequences are "substantially homologous" or "substantially similar" when greater than 50% of the amino acids are identical, or functionally identical. Preferably, the similar or homologous sequences are identified by alignment using, for example, the GCG (Genetics Computer Group, Program Manual for the GCG Package, Version 7, Madison, Wis. pileup program.

Thus, "homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences. An "unrelated" or "non-homologous" sequence shares less than 40% identity, though preferably less than 25% identity, with one of the sequences of the present invention. Therefore, a "homolog" of the circumsporozoite protein (CSP) of a *plasmodium* species or a fragment thereof, should share at least about 50% homology with the CSP or fragment thereof (preferably about 75% homology, more preferably about 90-95% homology and most preferably about 99% homology) and in addition should have at least about 50% identity with the region II-plus motif of the circumsporozoite protein as shown in FIG. 9 (see R II-plus in FIG. 9).

Thus, the term "percent identical" or "percent sequence identity" refers to sequence identity between two amino acid sequences or between two nucleotide sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

The terms "protein", "polypeptide" and "peptide" are used interchangeably herein when referring to a gene product and indicates a molecular chain of amino acids linked through covalent and/or noncovalent bonds. The terms do not refer to a specific length of the product. Thus, peptides, oligopeptides and proteins are included within the definition of polypeptide. The terms include post-expression modifications of the polypeptide, for example, glycosylations, acetylations, phosphorylations and the like. In addition, protein fragments, analogs, mutated or variant proteins, fusion proteins and the like are included within the meaning of polypeptide.

The terms "synthetic peptide" or "synthetic polypeptide" or "synthetic protein" are used interchangeably and refer to polymeric forms of amino acids of any length, which may be chemically synthesized by methods well-known to the skilled artisan. These synthetic peptides are useful in various applications.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as, double- and single-stranded RNA. It also includes modifications, such as methylation or capping, and unmodified forms of the polynucleotide. The terms "polynucleotide," "oligomer," "oligonucleotide," and "oligo" are used interchangeably herein.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, which is separated from some or all of the coexisting materials in the natural system, is isolated. Such polynucleotide could be part of a vector and/or such polynucleotide or polypeptide could be part of a composition, and still be isolated in that the vector or composition is not part of its natural environment.

"Encoded by" refers to a nucleic acid sequence which codes for a polypeptide sequence, wherein the polypeptide sequence contains an amino acid sequence of at least 3 to 5 amino acids, more preferably at least 8 to 10 amino acids, and even more preferably at least 15 to 20 amino acids, a polypeptide encoded by the nucleic acid sequences. Also encompassed are polypeptide sequences which are immunologically identifiable with a polypeptide encoded by the sequence. Thus, an antigen "polypeptide," "protein," or "amino acid" sequence may have at least 60% similarity, preferably at least about 75% similarity, more preferably about 85% similarity, and most preferably about 95% similarity, to a polypeptide or amino acid sequence of an antigen.

The term "recombinant protein" refers to a polypeptide of the present invention which is produced by recombinant DNA techniques, wherein generally, DNA encoding a particular polypeptide is inserted into a suitable expression vector which is in turn used to transform a host cell to produce the heterologous protein. Moreover, the phrase "derived from", with respect to a particular recombinant gene, is meant to include within the meaning of "recombinant protein" those proteins having an amino acid sequence of a particular native polypeptide, or an amino acid sequence similar thereto which is generated by mutations including substitutions and deletions (including truncation) of a naturally occurring form of the polypeptide.

"Fragment" refers to either a protein or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a parent protein or polypeptide, or a nucleic acid comprising a nucleotide sequence of at least 10 base pairs (preferably at least 20 base pairs, at least 30 base pairs, at least 40 base pairs, at least 50 base pairs, at least 50 base pairs, at least 100 base pairs, at least 200 base pairs) of the nucleotide sequence of the parent nucleic acid. Any given fragment may or may not possess a functional activity of the parent nucleic acid or protein or polypeptide.

A "biologically active" protein, peptide, peptide mimic, or fragment of any of the foregoing, refers to a circumsporozoite protein (CSP), peptide, peptide mimic, or fragment of any of the foregoing, that can suppress or deactivate an inflammatory cell in a manner analogous to the parent CSP molecule from a species of *plasmodium*, as described herein. The biological activity measured may be suppression of any activity or function associated with an inflammatory cell, including, but not limited to release of an inflammatory cytokine, such as IL-1, IL-6 or TNF. Or the biological activity may be related to a respiratory burst or release of reactive oxygen or nitrogen species or free radicals. Or, the activity may be a change in level of intracellular cAMP or IP3.

A "variant" includes a substantially homologous polypeptide encoded by the same genetic locus in an organism, i.e., an allelic variant, as well as other variants. Variants also encompass polypeptides derived from other genetic loci in an organism, but having substantial homology to a polypeptide encoded by a CSP nucleic acid molecule, and complements and portions thereof, or having substantial homology to a polypeptide encoded by a nucleic acid molecule comprising the nucleotide sequence of a CSP nucleic acid molecule. Variants also include polypeptides substantially homologous or identical to these polypeptides but derived from another organism, i.e., an ortholog. Variants also include polypeptides that are substantially homologous or identical to these polypeptides that are produced by chemical synthesis. Variants also include polypeptides that are substantially homologous or identical to these polypeptides that are produced by recombinant methods. Preferably, a CSP variant has at least 60%, more preferably, at least 70%, 75%, 80%, 85%, or 90%, and most preferably at least 95%, sequence identity to a CSP polypeptide described herein, for example, the sequence of SEQ ID NO:2 or SEQ ID NO: 4, as determined using the BLAST program and parameters described herein and one or more of the biological activities of a circumsporozoite protein, as determined using methods described herein or other methods known in the art.

The "circumsporozooite protein", "circumsporozoite polypeptide" or "CSP" refers to the major coat protein of the malaria (*plasmodium*) sporozoites. It presents a central repeat domain flanked by non-repeated amino and carboxyl sequences containing highly conserved protein stretches (regions I and II). These flanking regions also display some degree of polymorphism (Mann, V. H. et al. Mol Biochem Parasitol. November 1994;68 (1):45-52.).

The terms "mimic" or "mimetic" are used interchangeably herein and the terms are used to describe a molecule, which may or may not be proteinaceous in nature and extends to analogues, derivatives or variants of a circumsporozoite protein (CSP) and fragments thereof. The "mimics" or "mimetics" mimic the functional activity of the parent full length CSP as related to inhibition of macrophage activity or suppression of macrophage function and these mimics or mimetics may be either naturally derived or synthetically prepared. A peptide which mimics CSP is preferably at least three amino acids, although peptides of any length are within the scope of the invention. Accordingly, peptides and non-peptide mimics displaying substantially equivalent or altered activity are likewise contemplated. These modifications may be deliberate, for example, such as modifications obtained through site-directed mutagenesis, or may be accidental, such as those obtained through screening for mimics or mimetics using the methods and assays provided and described herein. Also, the terms mimic or mimetic are intended to include within their scope those peptides specifically recited herein as well as all variants, analogs and active fragments thereof, including substantially homologous variants and analogs. The identity or location of one or more amino acid residues may be changed or modified to include, for example, active fragments such as deletions containing less than all of the residues specified for the peptide, variants wherein one or more residues are replaced or substituted by other residues or wherein one or more amino acid residues are added to a terminal or medial portion of the peptide, and analogs wherein one or more residues are replaced or substituted with unnatural amino acids, L-amino acids, various "designer" amino acids (for example β-methyl amino acids, Cα methyl amino acids, and Nα methyl amino acids), nonclassical amino acids or synthetic amino acids. Analogs further encompass cyclic peptides, which can be generated by any of recognized methods in the art.

A "conservative amino acid substitution" refers to the substitution of one or more of the amino acid residues of a protein with other amino acid residues having similar physical and/or chemical properties. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point. Particularly preferred substitutions are:

- Lys for Arg and vice versa such that a positive charge may be maintained;
- Glu for Asp and vice versa such that a negative charge may be maintained;
- Ser for Thr such that a free —OH can be maintained; and
- Gln for Asn such that a free $NH_2$ can be maintained.

It is noted that in this disclosure, terms such as "comprises", "comprised", "comprising", "contains", "containing" and the like can have the meaning attributed to them in U.S. patent law; e.g., they can mean "includes", "included", "including" and the like. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. patent law; namely, that these terms are closed ended.

The "non-human mammal" of the invention include mammals such as rodents, including rats, mice and guinea pigs and non-human primates, and sheep, goats, rabbits, dogs, cats, cows, chickens, amphibians, reptiles, etc.

General Description

After transmission into the skin by an infected mosquito, malaria sporozoites rapidly travel to the liver, their initial site of replication in the mammalian host. To infect hepatocytes, sporozoites must cross the sinusoidal cell layer by passing through Kupffer cells. Surprisingly, the parasites are not killed by these resident macrophages of the liver. The present invention demonstrates that *Plasmodium berghei* and *P. yoelii* sporozoites as well as recombinant *P. falciparum* circumsporozoite protein (CSP) suppress the zymosan- and phorbol-12-myristate-13-acetate (PMA)-induced production of reactive oxygen species (respiratory burst) in Kupffer cells. Sporozoites and recombinant CSP increased in a dose- and time-dependent fashion the intracellular concentration of cyclic adenosyl monophosphate (cAMP) and inositol 1,4,5-triphosphate ($IP_3$) in Kupffer cells, but not in other liver cell types, hepatocytes and sinusoidal endothelia. Blockage of the respiratory burst was also observed when the cells were pre-incubated with the membrane-permeable cAMP analogue dibutyryl-cAMP or when the cAMP level was raised with the phosphodiesterase inhibitor IBMX. By contrast, inhibition of adenylyl cyclase by SQ 22,536 abrogated the suppressive effect of sporozoites on the respiratory burst. The selective protein kinase A (PKA) inhibitors H-89, $PKI_{14-22}$, and Rp-cAMP failed to reverse the CSP-mediated blockage of the respiratory burst suggesting that CSP acts via a cAMP-dependent, but PKA-independent mechanism. Specific blockage of the low-density lipoprotein receptor-related protein (LRP-1) with receptor-associated protein (RAP) inhibited the cAMP increase in Kupffer cells. Cell surface proteoglycans (syndecans) contribute to the cAMP elevation, since glycosaminoglycan elimination by glycosaminoglycan lyase digestion in combination with chlorate treatment decreased the generation of cAMP. The present invention proposes that by binding of CSP to LRP-1 and syndecans, malaria sporozoites induce signal transduction pathways that suppress defense mechanisms in Kupffer cells. This allows the sporozoites to safely pass through these professional phagocytes and to develop inside neighboring hepatocytes.

Accordingly, in its broadest aspect, the present invention provides for a method of reducing the activity or function of an inflammatory cell by contacting or exposing the cell to an isolated or purified circumsporozoite protein (CSP), or fragment, homolog or mimic thereof. More particularly, the inventors have found that the exposure of liver macrophages to the CSP of *plasmodium* species results in elevation of cyclic adenosine monophosphate (cAMP) and inositol-1,4,5-triphosphate (IP3) in inflammatory cells. Further, the exposure of the inflammatory cell to the CSP or homolog or fragment thereof also results in inhibition of the respiratory burst in the inflammatory cell.

The invention further provides for treating a subject with the CSP, or homolog, mimic or fragment thereof for inducing tolerance to an antigen for which tolerance is desired. These antigens may be autoantigens or alloantigens, including transplantation antigens. In addition, the CSP or homologs or fragments thereof may also be used to suppress or deactivate inflammatory cells in subjects suffering from an inflammation-associated or inflammatory disease, disorder or condition characterized by an influx of inflammatory cells to the site of disease or injury. Such inflammatory diseases may include liver diseases (including those characterized by fibrosis or cirrhosis), arthritis, inflammatory bowel diseases (including Crohn's disease, or inflammatory bowel disease), cardiac diseases or conditions, neurological disorders or injuries, including multiple sclerosis, traumatic brain injury, spinal cord injury or other conditions associated with inflammation, such as burns or wounds. The CSP or homologs, or fragments thereof or mimics may be used to suppress the activity or function of an inflammatory cell in diseases such as autoimmune diseases, or for use in transplantation surgery, or for antigen specific tolerance induction, including autoantigens, alloantigens and allergens.

The CSP, or homolog or fragment thereof may be isolated from the native organism by methods known to those skilled in the art, or it may be produced by recombinant means, or it may be synthesized by standard procedures known to the skilled artisan.

Furthermore, the CSP or homologs or fragments thereof may be formulated into a pharmaceutical composition in a therapeutically effective amount with a pharmaceutically acceptable carrier for treating such inflammatory diseases or conditions or for induction of tolerance. Accordingly, in a particular embodiment, the pharmaceutical composition comprises a therapeutically effective amount of either one of the polypeptides of SEQ ID NOs: 2 and 4, or a combination thereof, or of either one of the nucleic acids encoding these polypeptides, as set forth in the nucleotide sequences of SEQ ID NOs: 1 and 3, or a combination thereof.

Another aspect of the invention provides for identification of small molecule mimics of the CSP or homolog or fragment thereof for use as an agent that suppresses or deactivates an inflammatory cell. Such a small molecule mimic may then be used for tolerance induction or for treating an inflammatory disease, disorder or condition. In one specific embodiment, a method for identifying and testing the effect of a mimic of CSP activity is provided herein and includes use of an assay such as the measurement of cAMP or IP3 levels or by measuring the respiratory burst in an inflammatory cell, such as a liver macrophage (a Kupffer cell) as described herein. For example, the macrophages, which may be obtained from tissues or whole blood, or obtained commercially as a macrophage or monocyte cell line, such as the P388 cell line, are exposed to zymosan with or without the CSP or a candidate compound or mimic. The candidate compound or mimic may be a small organic molecule or a peptide, antibody, nucleic acid (RNA, DNA or an antisense or siRNA molecule), carbohydrate or lipid. The reactive oxygen intermediates are then measured by a procedure such as by chemiluminescence, as described herein. A biologically active mimic would produce inhibition of the respiratory burst to an equivalent or better level than the purified CSP or homolog or fragment thereof. Further testing may then be done in relevant animal models for the specific disease or condition for which treatment is desired.

Therapeutic Applications

It is contemplated that a CSP or a biologically active fragment thereof may be useful for treating any disease or condition that has an inflammatory component associated with the disease or condition. The influx of inflammatory cells to a diseased cell or tissue results in the release of a number of cytokines and protein factors by the inflammatory cells, as well as other free radicals, all of which result in further tissue damage and cell death. A decrease in the release of any of the above-noted proteins or factors may result in amelioration of one or more symptoms associated with the disease or condition, including a reduction in the swelling or pain associated with the inflammatory disease or condition. Some of the following diseases or conditions may benefit from therapy with a CSP or biologically active fragment thereof.

Chronic Liver Disease

Chronic liver disease is marked by the gradual destruction of liver tissue over time. Several liver diseases fall under this category, including cirrhosis and fibrosis (often the forerunner of cirrhosis) of the liver.

Cirrhosis is the seventh leading cause of death in the United States, according to the National Institute of Diabetes and Digestive and Kidney Diseases (NIDDK). Cirrhosis is defined pathologically by the loss of normal microscopic lobular architecture with fibrosis (i.e., the growth of scar tissue due to infection, inflammation, injury, or even healing) and nodular regeneration. Because of chronic damage to the liver, scar tissue slowly replaces normal functioning liver tissue resulting in progressively diminishing blood flow through the liver. As the normal liver tissue is lost, nutrients, hormones, drugs and poisons are not processed effectively by the liver. In addition, protein production and other substances produced by the liver are inhibited.

Symptoms of cirrhosis vary, depending on severity and individuals. Symptoms may include abnormal nerve function, ascites (build-up of fluid in the abdominal cavity), breast enlargement in men, coughing up or vomiting blood, curling of fingers (Dupuytren contracture of the palms), gallstones, hair loss, itching, jaundice, kidney failure, liver encephalopathy, muscle loss, poor appetite, portal hypertension, redness of palms, salivary gland enlargement in cheeks, shrinking of testes, small spider-like veins in skin, weakness, weight loss, etc. The symptoms of cirrhosis may resemble other conditions or medical problems. Mild cirrhosis may not exhibit any symptoms at all.

The most common cause of cirrhosis is alcohol abuse. Other causes include hepatitis and other viruses (e.g., HCV), use of certain drugs, chemical exposure, hepatotoxic drugs, bile duct obstruction, autoimmune diseases, obstruction of outflow of blood from the liver (i.e., Budd-Chiari syndrome), heart and blood vessel disturbances, alpha1-antitrypsin deficiency, high blood galactose levels, high blood tyrosine levels, glycogen storage disease, diabetes, malnutrition, hereditary accumulation of too much copper (Wilson Disease) or iron (hemochromatosis).

Clinical signs of chronic liver disease include spider angiomas (a central arteriole from which numerous small branching vessels radiate), jaundice (yellowish discoloration of the skin), pruritus (itching), gynecomastia (enlargement of the male breast), ascites (an effusion and accumulation of serous fluid in the abdominal cavity), encephalopathy, asterixis (flapping tremor), etc. In addition to a complete medical history and medical examination, diagnostic procedures for cirrhosis may include specific laboratory tests, liver function tests, liver biopsy, and cholangiography x-rays of the bile ducts).

Hepatitis C Virus Infection

The hepatitis C virus (HCV) is a blood-borne virus. HCV infection continues to be a major health problem in the U.S. and worldwide. According to the National Health and Nutrition Examination Survey (NHANES) of 1988-1994, 3.9 million Americans have been infected with hepatitis C virus, and of this group, 2.7 million were estimated to have chronic HCV infection. An estimated 50,000 cases occur annually in the U.S., making HCV infection the most common blood-borne infection in the U.S. (Wesley A. et al. Epidemiology of hepatitis C: geographic differences and temporal trends. Semin Liver Dis. 2000; 20(1):1-16). The exact prevalence of the disease is unknown, however, in Western Europe it is estimated to be 1% of the general population, 5% in some parts of Eastern Europe, and 10% in Egypt (Alberti A. et al. Natural history of hepatitis C. J Hepatol. 1999; 31 Suppl 1: 17-24). The prevalence in IV drug users is as high as 58-84% (Schwimmer J. B. et al. Transmission, natural history, and treatment of hepatitis C virus infection. Semin Liver Dis. 2000; 20(1): 37-46), putting them at high risk.

HCV is a single stranded RNA virus of the Flaviviridae family. There are 6 HCV genotypes (1a, 1b, 2a, 2b, 3, 4, 5, and 6) and more than 50 subtypes. These genotypes differ by as much as 30-50% in their nucleotide sequences. The virus has a high propensity to mutate, which further adds to the difficulties in vaccine development and treatment efficacy.

The hepatitis C virus enters the body through direct blood exposure. The virus attacks cells in the liver, where it multiplies (replicates) and therefore, causes liver inflammation and kills liver cells. Regardless of mode of acquisition, as many as 50-70% of people initially infected with HCV become chronically infected (the infection does not clear up within six months), and more than 50% of the HCV-infected people will develop chronic liver disease. Most people with chronic HCV infection do not have symptoms and lead normal lives. However, in 10-25% of people with chronic HCV infection, the disease progresses over decades, and may lead to serious liver damage, cirrhosis, and/or liver cancer. The prevalence of cirrhosis, which is pathologically characterized by loss of the normal microscopic lobular architecture, with fibrosis and nodular regeneration, is above 50% in these patients. Today, HCV infection is the leading cause for liver transplants.

The current understanding of the liver pathology in chronic HCV-infected patients is that the damage is due to the host immune response and not to the virus itself. Several lines of evidence support the concept that HCV, similar to HBV, is a non-cytopathic virus in the majority of cases (Rehermann B. Cellular immune response to the hepatitis C virus. J Viral Hepatol. 1999; 6 Suppl 1:31-5; Nelson D. R. et al. Pathogenesis of chronic hepatitis C virus infection. Antivir Ther. 1998; 3 (Suppl 3):25-35; Rehermann B. et al. Cell mediated immune response to the hepatitis C virus. Curr Top Microbiol Immunol. 2000; 242:299-325). A heightened host CD8+ cytotoxic T lymphocyte (CTL) response and an elevated cytokine tumor necrosis factor alpha (TNF-a) level, which are important in limiting viral replication, become the same immune responses responsible for damage to the liver once the infection has become chronic (Takaki A. et al. Cellular immune responses persist and humoral responses decrease two decades after recovery from a single-source outbreak of hepatitis C. Nat Med. 2000; 6(5):578-82). A significant correlation has also been found to exist between the number of lobular CD8+ cells and liver enzymes levels, suggesting the prominent role of T-cell mediated cytotoxicity in the genesis of hepatocellular damage (Rehermann B., supra. (1999); Nelson D. R. et al. supra.; Rehermann B. et al. supra. (2000); Naoumov N. V. Hepatitis C virus-specific CD4 (+) T cells: do they help or damage? Gastroenterology. 1999; 117(4): 1012-4; Gerlach J. T. et al. Recurrence of hepatitis C virus after loss of virus-specific CD4 (+) T-cell response in acute hepatitis C. Gastroenterology. 1999; 117(4):933-41; Lohr H. F. et al. The viral clearance in interferon-treated chronic hepatitis C is associated with increased cytotoxic T cell frequencies. J Hepatol. 1999; 31 (3):407-15).

There is currently no vaccine or cure for HCV infection. Current treatments are either based on anti-viral drugs or focus on attempts to augment the anti-viral immune response. However, the results of these approaches have been largely disappointing. The current response rate to the combination therapy of interferon and ribavirin is less than 50%. The vast majority of treated patients are either non-respondents or will suffer from relapse of the disease following termination of treatment. Moreover, these treatments are associated with a high percentage of side effects.

A positive effect of a CSP or active fragment thereof may be monitored in a hepatitis patient by assessing an effect on liver enzymes, or by measurement of hepatitis virus titers in the blood (serum or plasma) using standard PCR (polymerase chain reaction) methodology.

Non-Alcoholic Steatohepatitis

While the CSP, homolog or fragment thereof is contemplated for treatment of individuals suffering from liver cirrhosis or fibrosis associated with an infection or alcohol consumption, it is also contemplated for use in treating non-alcoholic steatohepatitis (NASH), also known as non-alcoholic fatty liver disease, which describes a hepatic disorder typically characterized by an alcoholic pathogenesis without alcohol consumption (Blechacz B. et al. NASH—nonalcoholic steatohepatitis [in German]. Z Gastroenterol. 2003;41(1):77-90). The fat deposit in liver cells is mostly triglyceride, and the severity of NASH is directly related to the amount of fat in the liver. Histologically, if 50% of liver cells had steatosis (fatty liver accumulation), or if the total weight of fat is greater than 5% of the entire liver, then steatohepatitis can be diagnosed. NASH is further characterized by elevated serum aminotransferase activities with hepatic steatosis, inflammation, and occasionally fibrosis that may progress to cirrhosis.

The prevalence of NASH is 3-19% throughout most of the world. There are many possible causes of NASH but there isn't a definite source. The most likely causes are obesity from poor diet, diabetes, long-term use of steroids and use of tetracycline (Bacon B. R. et al. Nonalcoholic steatohepatitis: An expanded clinical entity. Gastroenterology 1994; 107:1103-91; Powell E. E. et al. The natural history of nonalcoholic steatohepatitis: a follow-up study of forty-two patients for up to 21 years. Hepatology 1990; 11:74-80). Some studies have shown sign of steatosis reversal after weight loss (Eriksson S. et al. Nonalcoholic steatohepatitis in obesity: A reversible condition. Acta Med Scand. 1986; 220:83-8; Sheth S. G. et al. Nonalcoholic steatohepatitis. Ann Intern Med. 1997; 126(2): 137-45).

There is currently no established treatment that exists for this potentially serious disorder. Treatment of patients with nonalcoholic fatty liver has typically been focused on the management of associated conditions such as obesity, diabetes mellitus, and hyperlipidemia as well as discontinuation of potentially hepatotoxic drugs (Angulo P. et al. Treatment of nonalcoholic fatty liver: Present and emerging therapies. Sem Liver Dis. 2001;21(1):81-88).

Cirrhosis of the liver is a chronic disease that results in nodular regeneration of hepatocytes separated by thick septi of fibrous scar tissue. (See Conn's Current Therapy, "Cirrhosis," pp. 465-470, P. Pockros, (R. E. Rakel, ed.), W. B. Saunders Co., Philadelphia (2000)). The tissue growth is due to the hyperproliferation of hepatocytes (forming the nodules) and fibroblasts leading to extensive fibrosis (forming the scar tissue within the liver). Cirrhosis results in loss of function of hepatocytes and portal hypertension, ultimately resulting in liver failure. The causes of cirrhosis include alcoholism, nutritional deficiency, poisons, drugs or chemicals that are hepatotoxic, inflammation caused by a virus or bacteria, prolonged congestive heart failure and autoimmunity (such as primary biliary cirrhosis). Ongoing infection and/or inflammation is frequently involved in the disease.

In addition to the hepatic fibrosis that occurs during cirrhosis, localized or generalized fibrosis of the liver is associated with other diseases, including idiopathic portal hypertension, schistosomiasis, and congenital hepatic fibrosis. (See Harrison's Principles of Internal Medicine: Part Eleven, "Disorders of the Gastrointestinal System," Chapter 298, pp. 1704-1710, A. S. Fauci et al., (eds.), McGraw-Hill, New York (1998)).

Liver diseases, including fibrosis and cirrhosis, often result from, at least in part, ongoing inflammatory processes. These inflammatory processes may be caused by, among other things, viral, parasitic or bacterial infection, exposure of the liver to chemicals and other hepatotoxins or autoimmunity. The inflammatory process results in injury to the liver, ultimately leading to diseases including fibrosis and cirrhosis. The circumsporozoite proteins, homologs thereof and fragments thereof may prove beneficial in treating these conditions.

Use of CSP and Fragments thereof for Treatment of Other Inflammatory Diseases

Based on the findings of the present invention, a CSP or fragment thereof that modulates the levels of cAMP and $IP_3$ in macrophages, and which inhibits the respiratory burst in macrophages while altering the cytokine profile such that pro-inflammatory cytokines are decreased while anti-inflammatory cytokines are increased, may be used to treat other inflammatory diseases or conditions associated with the presence of inflammatory cells. In a particular embodiment, the agent for treating such disease or condition would be a substantially purified CSP, either obtained (isolated and purified) from a *Plasmodium* species, or it may be produced recombinantly using techniques known in the art. In another particular embodiment, a biologically active fragment obtained from a CSP (by "biologically active", as used herein, is meant that the fragment retains the ability to inhibit macrophage activity or suppress macrophage function, in particular, the fragment retains the anti-inflammatory properties associated with the full-length CSP parent molecule) may be contemplated for use. The treatment with such a molecule may diminish the tissue damage associated with the presence of the inflammatory cells and mediators. The diseases for which treatment with such a molecule may be effective are summarized below.

Inflammatory Bowel Disease

The CSP or a biologically active fragment, analogue, derivative or mimic thereof, or any combination of the foregoing, may be particularly effective for treating an inflammatory bowel disease (IBD). Ulcerative colitis (UC) and Crohn's disease are the two major forms of idiopathic Inflammatory Bowel Disease (IBD) in humans, and are widespread and poorly understood disorders (Kirsner, J. B., et al., eds., Inflammatory Bowel Disease: 3rd ed., Lea and Febiger, Philadelphia (1988); Goldner, F. H., et al., Idiopathic Inflammatory Bowel Disease, in Stein, J. H., ed., Internal Medicine, Little Brown & Co., Boston, pp. 369-380 (1990); Cello, J. P., et al. Ulcerative Colitis, in Sleisenger, M. H., et al. eds., Gastrointestinal Disease: Pathophysiology Diagnosis Management, W. B. Saunders Co., Philadelphia, p. 1435 (1989)). Other forms of IBD include those caused by infectious agents, drugs, or the solitary rectal ulcer syndrome and collagenous colitis. The diagnosis of IBD of known and unknown etiology is difficult and sometimes impossible to make (Riddell, R. H., ed., Pathology of Drug-induced and Toxic Diseases, Churchill Livingstone, New York (1982)).

Colitis generally refers to a more superficial mucosal disease in contrast to Crohn's disease, which presents as a deep, often transmucosal involvement and fissures (Riddell, R. H., ed., Pathology of Drug-induced and Toxic Diseases, Churchill Livingstone, New York (1982); Morrison, B. C., et al. eds., Gastrointestinal Pathology, 2d ed., London (1979); Fenoglio-Preiser, C. M., et al., eds., Gastrointestinal Pathology: An Atlas and Text, Raven Press, New York (1989); Goldman, H., et al., Hum. Pathol. 13:981-1012 (1982)). Ulcerative colitis typically involves the rectum and extends proximally without intervening uninvolved areas. These uninvolved areas are usually the hallmark of Crohn's disease. The histologic features of active ulcerative colitis include, beside the superficial ulcers, infiltration by inflammatory cells (e.g., mainly lymphocytes, plasma cells, variable number of neutrophils, eosinophils and mast cells) involving extensively the lamina propria. Crypt abscesses, which are aggregates of neutrophils near and invading the crypt epithelium, are generally reliable indicators of activity, while depletion of mucin in goblet cells is a less frequent finding. Foreign-body giant cells and collection of a few histiocytes, however, may be present due to the rupture of crypt abscesses and the spilling of mucin into the submucosa, which often elicits a cellular reaction. Noncaseating granulomas, may be present in gut segments from Crohn's disease, which is often also called granulomatous colitis.

The etiology and pathogenesis of idiopathic IBD, as the name implies, are poorly understood. Numerous theories, however, implicate genetic predisposition, environmental factors, infectious agents and immunologic alterations (Kirsner, J. B., et al. eds., Inflammatory Bowel Disease, 3rd ed., Lea and Febiger, Philadelphia (1988); Zipser, R. D., ed., Dig. Dis. Sci., 33 Suppl.: 1S-87S (1988)).

Eliakim et al. have demonstrated enhanced production of platelet-activating factor (PAF) during active disease and inhibition by sulfasalazine and prednisolone (Eliakim, R., et al., Gastroenterology 95:1167-1172 (1988)), thus implicating PAF as a possible mediator in the disease process. Furthermore, an enhanced synthesis of eicosanoids such as prostaglandins, thromboxanes and leukotrienes has been shown in both human and experimental IBD (Schumert, R., et al., Dig. Dis. Sci. 33 Suppl.:58S-64S (1988)). These products may be involved in the pathogenesis of IBD. Selective inhibition of leukotrienes may be a therapeutic strategy to reduce inflammation in IBD (Schumert, R., et al., Dig. Dis. Sci. 33 Suppl.: 58S-64S (1988); Goetzl, E. J., et al., Dig. Dis. Sci. 33 Suppl.: 36S-40S (1988); Allgayer, H., et al., Gastroenterology 96:1290-1300 (1989)).

Potential humoral mediators of inflammation may also be involved in the pathogenesis of IBD, e.g., tumor necrosis factor, growth factors, neuropeptides, lipoxins, and mast cell products (Zipser, R. D., ed., Dig. Dis. Sci., 33 Suppl.:IS-87S (1988); Shanahan, F., et al., Dig. Dis. Sci. 33 Suppl.:41S-49S (1988); Nast, C. C., et al., Dig. Dis. Sci 33 Suppl.:50S-57S (1988); Mayer, E. A., et al., Dig. Dis. Sci. 33 Suppl.:71S-77S (1988)). It is also possible that not only the number of inflammatory cells and their products are changed, but the number of receptors increase, such as the increased neutrophil receptors for and response to the proinflammatory peptide formyl-methionyl-leucyl-phenylalanine (FMLP) (Anton, P. A., et al., Gastroenterology 97:20-28 (1989)) and the adherence of leukocytes (Cason, J., et al., J. Clin. Pathol. 41:241-246 (1988)) in Crohn's disease.

The immunologic alterations in IBD are primarily autoimmune in nature, with colonic autoantibodies and lymphocyte-cytotoxicity directed against colonic epithelial cells. There are many animal models utilized to study the etiology and pathogenesis of IBD. The criteria for an animal model of IBD have been reviewed (Strober, W., Dig. Dis. Sci. 33 Suppl.:3S-1OS (1988); Beekan, W. L., Experimental inflammatory bowel disease, in: Kirsner, J. B., et al., eds., Inflammatory Bowel Disease, Lea and Febiger, Philadelphia, pp. 37-49 (1988)). The available animal models can be divided into naturally occurring and experimentally induced IBD animal models. Only a few spontaneous and rarely occurring models of intestinal inflammation due to a genetic defect are available and most of these are not idiopathic but are induced by bacteria or other infectious agents (e.g., hyperplasia, crypt abscesses, ulcers in mice with *Bacillus psyliformnis* and hamster with "rod-shaped bacteria") (Strober, W., Dig. Dis. Sci. 33 Suppl.:3S-1OS (1988)). Rare forms of spontaneous ulcerative colitis and granulomatous enterocolitis also occur in rats and horses, respectively.

Experimentally induced animal models of ulcerative colitis are usually produced by exposure to toxic dietary substances, pharmacologic agents or other environmental chemicals, or by administration of materials derived from patients, or by manipulation of the animal's immune system (Strober, W., Dig. Dis. Sci. 33 Suppl.:3S-1OS (1988); Beekan, W. L., Experimental inflammatory bowel disease, in: Kirsner, J. B., et al., eds., Inflammatory Bowel Disease, Lea and Febiger, Philadelphia, pp. 37-49 (1988); Onderdonk, A. B., Dig. Dis. Sci. 33 Suppl.:40S-44S (1988)).

The most widely used models are the experimental colonic lesions produced by dinitrobenzene sulfonic acid (DNBS), 2,4,6-trinitro-benzensulfonic acid (TNBS) and carrageenan. These models involve tissue destruction in the colon. Intrarectal administration of 5-30 mg of TNBS in 0.25 ml of 50% ethanol in the rat produces dose-dependent colonic ulcers and inflammation which are observed by gross and light microscopic examination, and by biochemical measurement of myeloperoxidase activity in the colon at 3-4 weeks (Morris, G. P., et al., Gastroenterology 96:795-803 (1989)). Histologically, the inflammatory infiltrate of mucosa and submucosa included polymorphonuclear leukocytes, lymphocytes, macrophages and connective tissue mast cells. Initially, massive edema and in the healing state (6-8 weeks) fibroblasts are also detected. Granulomas are also seen in 57% of rats killed at 3 weeks.

Carrageenan is a sulfated polygalactose (molecular weight above 100,000) widely used in the food industry and is considered safe for human use. Degraded forms of this polysaccharide (molecular weight 20,000-40,000) administered through drinking water induce ulcerative colitis in two weeks or later in experimental animals (Beekan, W. L., Experimental inflammatory bowel disease, in: Kirsner, J. B., et al., eds., Inflammatory Bowel Disease, Lea and Febiger, Philadelphia, pp. 37-49 (1988); Onderdonk, A. B., Dig. Dis. Sci. 33 Suppl.: 40S-44S (1988); Benitz, K. F., et al., Food Cosmet. Toxicol. 11:565 (1973); Engster, M., et al., Toxicol. Appl. Pharmacol. 38:265 (1976)). In addition to ulcers, acute and chronic inflammation, macrophages laden with degraded carrageenan and suppressed phagocytosis are seen.

In addition to carrageenan, the FMLP-induced experimental colonic lesions also represent a transition between chemically and cellularly induced animal models. This bacterial peptide activates and attracts neutrophils, and causes ulcers and inflammation in the rat ileum (VonRitter, C., et al., Gastroenterology 95:651-656 (1988); VonRitter, C., et al., Gastroenterology 96:811-816 (1989)). This new animal model, like the TNB, has not yet been extensively used.

Szabo proposed a new model for ulcerative colitis, which incorporates the administration of a sulfhydryl blocker, such as N-ethylmaleimide, iodoacetamide, iodoacetate or chloroacetate (U.S. Pat. No., 5,214,066), to the intestinal mucosa of animals. Delivery of these agents to the colon of rodents resulted in chronic ulcerative colitis.

Multiple Sclerosis

Another inflammatory disease that may respond to treatment with a CSP or biologically active fragment thereof is multiple sclerosis. MS is a multi-factorial inflammatory disease of the human central nervous system resulting in the slowing of electrical conduction along the nerve. The disease is characterized by an increase in the infiltration of inflammatory cells, loss of oligodendrocytes, and increased gliosis (astrocyte hypertrophy and proliferation). (For review see Amit et al., 1999; Pouly et al., 1999; Steinman et al., 1993; Miller, 1994). Myelin is the target of this cellular autoimmune inflammatory process, leading to impaired nerve conduction (for a review, see e.g. Thompson 1996, Clin. Immunother. 5, 1-11). Clinical manifestations are variable, but are usually characterized by an initial relapsing-remitting course, with acute exacerbation followed by periods of clinical stability. Over time, a steady deterioration in neurological functions takes place as the disease evolves into a chronic progressive phase. This deterioration is responsible for disabling complications and side-effects, which greatly affect quality of life and increases mortality risk of affected patients. It is estimated that close to a third of a million people in the United States have MS.

There are several models that are widely used for testing therapies that may be effective in treating MS. One model is the Experimental Allergic Encephalomyelitis (EAE) model. EAE is a T cell mediated autoimmune disease of the central nervous system (CNS). Disease can be induced in susceptible strains of mice (SJL mice) by immunization with CNS myelin antigens or alternatively, disease can be passively transferred to susceptible mice using antigen stimulated CD4+ T cells (Pettinelli, J. Immunol. 127, 1981, p. 1420). EAE is widely recognized as an acceptable animal model for multiple sclerosis in primates (Alvord et al. (eds.) 1984. Experimental allergic encephalomyelitis—A useful model for multiple sclerosis. Alan R. Liss, New York). Another commonly utilized experimental MS model is a viral model, whereby an MS like disease is induced by Theiler's murine encephalomyelitis virus (TMEV) (Dal Canto, M. C., and Lipton, H. L., Am. J. Path., 88:497-500 (1977)). Additionally, the lysolecithin model is widely accepted as a model for demyelinating conditions such as MS.

Arthritis

It is also possible that a CSP or biologically active fragment thereof may be used to treat arthritis, both rheumatoid arthritis and osteoarthritis.

Rheumatoid arthritis (RA) is a chronic, systemic and articular inflammatory disorder which is characterized as an imbalance in the immune system that causes an overproduction of pro-inflammatory cytokines, e.g., tumor necrosis factor alpha (TNFα), interleukin 1 (IL-1), and a lack of anti-inflammatory cytokines, e.g. IL-10, IL-11. RA is characterized by synovial inflammation, which progresses to cartilage destruction, bone erosion and subsequent joint deformity. The primary symptoms of RA are joint inflammation, stiffness, swelling, fatigue, difficulty moving, and pain. During the inflammatory process, polymorphonuclear cells, macrophages, and lymphocytes are released. Activated T-lymphocytes produce cytotoxins and pro-inflammatory cytokines, while macrophages stimulate the release of prostaglandins and cytotoxins. Vasoactive substances (histamine, kinins, and prostaglandins) are released at the site of inflammation and cause edema, warmth, erythema, and pain associated with inflamed joints.

The pathogenesis of rheumatoid arthritis, leading to the destruction of the joints, is characterized by two phases: 1) an exudative phase involving the microcirculation of the synovial cells that allow an influx of plasma proteins and cellular elements into the joint and 2) a chronic inflammatory phase occurring in the sub-synovium and sub-chondral bone, characterized by pannus (granulation tissue) formation in the joint space, bone erosion, and cartilage destruction. The pannus may form adhesions and scar tissue which causes the joint deformities characteristic of rheumatoid arthritis.

The etiology of rheumatoid arthritis remains obscure. Infectious agents such as bacteria and viruses have been implicated.

Current rheumatoid arthritis treatment consists predominantly of symptomatic relief by administration of non-steroidal anti-inflammatory drugs (NSAIDs). NSAID treatment is mainly effective in the early stages of rheumatoid arthritis; it is unlikely it will produce suppression of joint inflammation if the disease is present for more than one year. Gold, methotrexate, immunosuppressants and corticosteroids are also used.

Osteoarthritis is a disorder of the movable joints characterized by deterioration and abrasion of articular cartilage, as well as by formation of new bone at the joint periphery and usually presents as pain, which worsens with exercise, or simply an X-ray that clearly shows thinning cartilage. Common joints affected are the knees, hips and spine, finger, base of thumb and base of the big toe. Osteoarthritis is characterized by degenerative changes in the articular cartilage (the supporting structure) and subsequent new bone formation at the articular margins. As osteoarthritis progresses, the surface of the articular cartilage is disrupted and wear-particles gain access to the synovial fluid which in turn stimulates phagocytosis by macrophage cells.

Thus, an inflammatory response is eventually induced in osteoarthritis. Common clinical symptoms of osteoarthritis include cartilaginous and bony enlargements of the finger joints and stiffness on awakening and painful movement.

There is no definitive answer regarding the cause of osteoarthritis. A natural erosion of cartilage occurs with age, but excessive loads placed on joints, obesity, heredity, trauma, decreased circulation, poor bone alignment, and repetitive stress motion play a role. Osteoarthritis may also be the result of free radical damage, thought to be a major cause of many diseases, including the aging process, cancer, heart disease and degenerative diseases.

There is no known drug that claims to reverse osteoarthritis. Most therapeutic agents are directed at reducing the inflammation and relieving pain. Non-steroidal anti-inflammatory drugs (NSAIDs) are the first line of treatment for osteoarthritis. Other treatments include disease-modifying arthritic drugs ("DMARDs"), steroids, and physical therapy.

One of the models used to test for new therapies for arthritis includes the collagen-induced arthritis model (CIA) (Myers, L. K. et al. Life Sci. (1997), 61(19): 1861-1878). In this model, immunization of genetically susceptible rodents or primates with Type II collagen (CII) leads to the development of a severe polyarticular arthritis that is mediated by an autoimmune response. It mimics RA in that synovitis and erosions of cartilage and bone are the hallmarks of CIA.

Diabetes

It is also possible that a CSP or a biologically active fragment thereof may be used to treat diabetes, in particular insulin-dependent diabetes mellitus (IDDM). The main clinical feature of IDDM is elevated blood glucose levels (hyperglycemia). The elevated blood glucose level is caused by auto-immune destruction of insulin-producing β-cells in the islets of Langerhans of the pancreas (Bach et al. 1991, Atkinson et al. 1994). This is accompanied by a massive cellular infiltration surrounding and penetrating the islets (insulitis) composed of a heterogeneous mixture of CD4+ and CD8+ T-lymphocytes, B-lymphocytes, macrophages and dendritic cells (O'Reilly et al. 1991).

One animal model that is particularly useful in testing agents for treating IDDM is the NOD mouse. The NOD mouse represents a model in which auto-immunity against beta-cells is the primary event in the development of IDDM. Diabetogenesis is mediated through a multi-factorial interaction between a unique MHC class II gene and multiple, unlinked, genetic loci, as in the human disease. Moreover, the NOD mouse demonstrates beautifully the critical interaction between heredity and environment, and between primary and secondary auto-immunity. Its clinical manifestation is, for example, depending on various external conditions, most importantly on the micro-organism load of the environment in which the NOD mouse is housed.

Another animal model for studying the effects of therapeutic agents in IDDM, for example, a CSP or biologically active fragment thereof, is the streptozotocin (STZ) model (Hartner, A. et al. (2005), BMC Nephrol. 6(1):6). This model has been used extensively as an animal model to study the mechanisms involved in the destruction of pancreatic beta cells in IDDM. In this model, diabetes is induced in rodents by the beta-cell toxin streptozotocin (STZ). STZ is taken up by the pancreatic beta cell through the glucose transporter GLUT-2. This substance decomposes intracellularly, and causes damage to DNA either by alkylation or by the generation of NO. The appearance of DNA strand breaks leads to the activation of the abundant nuclear enzyme poly(ADP-ribose) polymerase (PARP), which synthesizes large amounts of the (ADP-ribose) polymer, using NAD+ as a substrate. As a consequence of PARP activation, the cellular concentration of NAD+ may then decrease to very low levels, which is thought to abrogate the ability of the cell to generate sufficient energy and, finally, to lead to cell death.

Other Therapeutic Indications

Further, other inflammation inducing conditions may be treated to ameliorate symptoms associated with inflammation or to diminish the existing inflammation. Inflammation or irritation associated therewith may be from a variety of sources either physical or chemical, and may include: insect bites or stings, contact with a particular type plant (e.g., poison oak, etc.), radiation (e.g., U.V.), non-infectious conjunctivitis, hemorrhoids (acute), abrasions, ingrown finger or toenail (granulation), skin graft donor sites, vaginitis, psoriasis, herpes simplex (cold sores, aphthous ulcers), pruritis ani/cruri, chemical inflammation, and the like. Accordingly, the compositions and methods set forth herein, find utility not only in treating inflammatory diseases, but also for treatment of the associated conditions and symptoms.

Inflammation is the result of extraneously induced damage to cells or tissue. As noted above, the damage to cells and/or tissues can be attributed in part to the release of free radicals at the site of disease or injury. In addition, due to the influx of inflammatory cells to a site of disease or injury, the inflammatory cells, such as macrophages, monocytes or neutrophils may exacerbate the condition due to the release of certain cytokines, protein factors, as well as reactive oxygen or nitrogen species. In addition, such damage may be induced by chemical and/or physical influences upon the skin or mucus membranes of humans and animals. Examples of physical influences are infarction, heat, cold, radiation and electrical shock, and examples of chemical influences are contact with acids, bases and allergens. Inflammation may be induced by microorganisms acting on the skin, as well as being the result of microorganisms invading the human or animal body.

A variety of symptoms are associated with inflammation and include, but are not limited to one or more of the following: pain, increased surface temperature, swelling, itching, and reduced or ceased function.

The inflammatory responses that may be ameliorated by treating with a CSP or an active fragment thereof, may be on the skin or a mucus membrane of an animal and includes, but is not limited to, conditions such as inflammation around erupting wisdom teeth, following extraction of teeth, periodontal abscesses, prosthesis induced pressure sores on the mucosa, fungal infections, for treating exposed bone surface in alveolitis sicca dolorosa, which is a painful condition which may arise following extraction of teeth, chronic and acute inflammatory diseases including, but not limited to, pancreatitis, rheumatoid arthritis, osteoarthritis, asthma, inflammatory bowel disease, psoriasis and in certain neurological disorders such as Alzheimer's disease or stroke, or following a traumatic injury to the brain or spinal cord.

The CSP or active fragment thereof and compositions thereof may also be useful in wound repair, when used alone to treat the accompanying inflammation or when used in conjunction with a wound healing agent. A wound is tissue loss or damage anywhere in the body caused by physical or chemical means, chronic irritation and/or inflammation of body tissue. Agents known to be useful in wound repair include anti-inflammatory agents and locally applied agents useful in the production of collagen and fibrous tissue.

As those of ordinary skill in the art can readily appreciate, while the CSP or active fragments thereof are contemplated for use primarily in humans, veterinary uses are also within the scope of the present invention. In one embodiment, the composition for cosmetic, pharmaceutical or dermatological usage comprises at least one CSP or active fragment thereof, or a combination of the foregoing, which suppresses macrophage activation as measured by one or more of the following: suppression of pro-inflammatory cytokine release (including for example, TNF- alpha, IL-1, IL-6) by a macrophage, or an increase in cAMP or IL3 in a macrophage, or a decrease in the respiratory burst in a macrophage, or a decrease in the release of one or more free radicals by a macrophage.

Use of the Circumsporozoite Proteins or Homologs or Fragments thereof for Inducing Tolerance or for Treatment of Autoimmune Disease The invention provides for the induction of tolerance to an autoantigen for the treatment of autoimmune diseases by administering the antigen for which tolerance is desired along with the CSP or homolog or fragment thereof. For example, autoantibodies directed against the acetylcholine receptor (AChR) are observed in patients with Myasthenia gravis, and, accordingly, AchR-antigen or antigen expressing vectors may be used in the invention to be delivered in conjunction with a CSP or homolog or fragment thereof to treat and prevent Myasthenia gravis.

By way of another non-limiting example, an individual who is a candidate for a transplant from a non-identical twin may suffer from rejection of the engrafted cells, tissues or organs, as the engrafted antigens are foreign to the recipient. Prior tolerance of the recipient individual to the intended graft abrogates or reduces later rejection. Reduction or elimination of chronic anti-rejection therapies may be achieved by the practice of the present invention. In another example, many autoimmune diseases are characterized by a cellular immune response to an endogenous or self antigen. Tolerance of the immune system to the endogenous antigen is desirable to control the disease.

In a further example, sensitization of an individual to an industrial pollutant or chemical, such as may be encountered on-the-job, presents a hazard of an immune response. Prior tolerance of the individual's immune system to the chemical, in particular in the form of the chemical reacted with the individual's endogenous proteins, may be desirable to prevent the later occupational development of an immune response.

Allergens are other antigens for which tolerance of the immune response thereto is also desirable. Likewise, autoantigens could be delivered to an inflammatory cell by a way that elicits specific immunotolerance. In one particular embodiment, the antigen for which tolerance is desired may be delivered with the CSP, homolog thereof or fragment thereof intravenously via the portal vein.

Notably, even in diseases where the pathogenic autoantigen is unknown, bystander suppression may be induced using antigens present in the anatomical vicinity injected along with the CSP or homolog or fragment thereof. For example, autoantibodies to collagen are observed in rheumatoid arthritis and, accordingly, a collagen-encoding gene may be utilized as the antigen-expressing gene module in order to treat rheumatoid arthritis (see e.g. Choy (2000) Curr Opin Investig Drugs 1: 58-62). Furthermore, tolerance to beta cell autoantigens may be utilized to prevent development of type 1 diabetes (see e.g. Bach and Chatenoud (2001) Ann Rev Immunol 19: 131-161).

As another example, auto-antibodies directed against myelin oligodendrocyte glycoprotein (MOG) is observed in autoimmune encephalomyelitis and in many other CNS diseases as well as multiple sclerosis (see e.g. Iglesias et al. (2001) Glia 36: 22-34). Accordingly, use of MOG antigen expressing constructs in the invention delivered with a CSP or a homolog or fragment thereof allows for treatment of multiple sclerosis as well as related autoimmune disorders of the central nervous system.

Still other examples of candidate autoantigens for use in treating autoimmune disease include: pancreatic beta-cell antigens, insulin and GAD to treat insulin-dependent diabetes mellitus; collagen type 11, human cartilage gp 39 (HCgp39) and gp130-RAPS for use in treating rheumatoid arthritis; myelin basic protein (MBP), proteolipid protein (PLP) and myelin oligodendrocyte glycoprotein (MOG, see above) to treat multiple sclerosis; fibrillarin, and small nucleolar protein (snoRNP) to treat scleroderma; thyroid stimulating factor receptor (TSH-R) for use in treating Graves' disease; nuclear antigens, histones, glycoprotein gp70 and ribosomal proteins for use in treating systemic lupus erythematosus; pyruvate dehydrogenase dehydrolipoamide acetyltransferase (PCD-E2) for use in treating primary billiary cirrhosis; hair follicle antigens for use in treating alopecia areata; and human tropomyosin isoform 5 (hTM5) for use in treating ulcerative colitis.

Nucleic Acids of the Present Invention

The invention provides for circumsporozoite protein-encoding and other nucleic acids, homologs thereof, and fragments or portions thereof. Preferred nucleic acids have a sequence at least about 50%, 60%, 65%, 70%, 75%, 80%, and more preferably 85% homologous and more preferably 90% and more preferably 95% and even more preferably at least 99% homologous with a nucleotide sequence of a subject gene, e.g., CSP-encoding gene. Nucleic acids at least 90%, more preferably 95%, and most preferably at least about 98-99% identical with a nucleic sequence represented in one of the subject nucleic acids of the invention or complement thereof are of course also within the scope of the invention. In preferred embodiments, the nucleic acid is mammalian and in particularly preferred embodiments, includes all or a portion of the nucleotide sequence corresponding to the coding region which correspond to the coding sequences of the subject CSP or homolog or fragment-encoding DNAs. In a particular embodiment, the nucleic acids encoding the CSP or fragments thereof are set forth in SEQ ID NOS: 1, 3, 5, 7, 9, 11, 13, 15, 17 and 19.

The invention also pertains to isolated nucleic acids comprising a nucleotide sequence encoding CSP polypeptides, variants and/or equivalents of such nucleic acids. The term equivalent is understood to include nucleotide sequences encoding functionally equivalent CSP polypeptides or functionally equivalent peptides having an activity of a CSP protein such as described herein. Equivalent nucleotide sequences will include sequences that differ by one or more nucleotide substitution, addition or deletion, such as allelic variants; and will, therefore, include sequences that differ from the nucleotide sequences of e.g. the corresponding CSP gene GenBank entries due to the degeneracy of the genetic code.

Preferred nucleic acids are vertebrate CSP nucleic acids. Particularly preferred vertebrate CSP nucleic acids are mammalian. Regardless of species, particularly preferred CSP nucleic acids encode polypeptides that are at least 50%, 60%, 65%, 70%, 75%%, 80%, 85%, 90%, 95%, or 99% similar or identical to an amino acid sequence of a vertebrate CSP protein. In one embodiment, the nucleic acid is a cDNA encoding a polypeptide having at least one bio-activity of the subject CSP polypeptides. Preferably, the nucleic acid includes all or a portion of the nucleotide sequence corresponding to the nucleic acids available through GenBank.

Still other preferred nucleic acids of the present invention encode a CSP-encoding polypeptide which is comprised of at least 2, 5, 10, 25, 50, 100, 150 or 200 amino acid residues. For example, such nucleic acids can comprise about 50, 60, 70, 80, 90, or 100 base pairs. Also within the scope of the invention are nucleic acid molecules for use as probes/primer or antisense molecules (i.e. noncoding nucleic acid molecules), which can comprise at least about 6, 12, 20, 30, 50, 60, 70, 80, 90 or 100 base pairs in length.

Another aspect of the invention provides a nucleic acid which hybridizes under stringent conditions to a nucleic acid represented by any of the subject nucleic acids of the invention. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6 or in Molecular Cloning: A Laboratory Manual, Cold Spring Harbor Press (1989). For example, the salt concentration in the wash step can be selected from a low stringency of about 2.0×SSC at 500° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature and salt concentration may be held constant while the other variable is changed. In a preferred embodiment, an antigen nucleic acid of the present invention will bind to one of the subject SEQ ID NOs. or complement thereof under moderately stringent conditions, for example at about 2.0×SSC and about 40° C. In a particularly preferred embodiment, a CSP encoding nucleic acid of the present invention will bind to one of the nucleic acid sequences of SEQ ID NOs: 1, 3, 5, 7, 9, 11, 13, 15, 17, 19 or complement thereof under high stringency conditions. In another particularly preferred embodiment, a CSP-encoding nucleic acid sequence of the present invention will bind to one of the nucleic acids of the invention which correspond to a CSP-encoding ORF nucleic acid sequences, under high stringency conditions.

Nucleic acids having a sequence that differs from the nucleotide sequences shown in one of the nucleic acids of the invention or complement thereof due to degeneracy in the genetic code are also within the scope of the invention. Such nucleic acids encode functionally equivalent circumsporozoite peptides (i.e., peptides having a biological activity of a CSP-encoding polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a circumsporozoite polypeptide. However, it is expected that DNA sequence polymorphisms that do lead to changes in the amino acid sequences of the subject circumsporozoite polypeptides will exist among mammals. One skilled in the art will appreciate that these variations in one or more nucleotides (e.g., up to about 3-5% of the nucleotides) of the nucleic acids encoding polypeptides having an activity of a circumsporozoite-encoding polypeptide may exist among individuals of a given species due to natural allelic variation.

Polypeptides of the Present Invention

The present invention makes available isolated polypeptides which are isolated from, or otherwise substantially free of other cellular proteins. The term "substantially free of other cellular proteins" (also referred to herein as "contaminating proteins") or "substantially pure or purified preparations" are defined as encompassing preparations of circumsporozoite (or homologs thereof) polypeptides having less than about 20% (by dry weight) contaminating protein, and preferably having less than about 5% contaminating protein. Functional forms of the subject polypeptides can be prepared, for the first time, as purified preparations by using a cloned gene as described herein.

Preferred circumsporozoite proteins of the invention have an amino acid sequence which is at least about 50%, 55%, 60%, 65%, 70%, 75%, 80%, 85%, 90%, 95%, or 99% identical or homologous to an amino acid sequence of a SEQ ID No. 2 and 4 of the invention. Even more preferred circumsporozoite proteins comprise an amino acid sequence of at least 10, 20, 30, or 50 residues which is at least about 50, 60, 70, 80, 90, 95, 97, 98, or 99% homologous or identical to an amino acid sequence of any one of SEQ ID Nos: 2, 4, 6, 8, 10, 12, 14, 16, 18, 20 or 21-48, particularly 31-48, and which share the common motif in region II-plus as shown in FIG. 9. Such proteins can be recombinant proteins, and can be, e.g., produced in vitro from nucleic acids comprising a nucleotide sequence set forth in any one of SEQ ID NOs: 1, 3, 5, 7, 9, 11, 13, 15, 17 or 19, or homologs thereof. For example, recombinant polypeptides preferred by the present invention can be encoded by a nucleic acid, which is at least 50% homologous or 75% homologous and more preferably 90% homologous and most preferably 95% homologous with a nucleotide sequence set forth in any one of SEQ ID Nos. 1, 3, 5, 7, 9, 11, 13, 15, 17 or 19, of the invention, and which encode the region II-plus motif as shown in FIG. 9. Polypeptides which are encoded by a nucleic acid that is at least about 98-99% homologous with the sequence of a SEQ ID Nos.: 1, 3, 5, 7, 9, 11, 13, 15, 17 or 19, of the invention are also within the scope of the invention. Most preferably, a homolog of CSP or a fragment thereof shares the region II-plus motif as shown in FIG. 9 of the present invention, exemplified in SEQ ID NOS: 31-48.

In a preferred embodiment, an circumsporozoite protein of the present invention is a mammalian circumsporozoite protein. In a particularly preferred embodiment a circumsporozoite protein is set forth as a SEQ ID NOs. 2 and 4 of the invention. In another particular embodiment, the circumsporozoite protein is selected from any one or more of the proteins selected from the group consisting of SEQ ID NOS: 2, 4, 6, 8, 10, 12, 14, 16, 18 and 20. In a particularly preferred embodiment, a circumsporozoite protein (or a homolog thereof or a fragment thereof) has inflammatory cell suppressing or deactivating bioactivity. It will be understood that certain post-translational modifications, e.g., phosphorylation and the like, can increase the apparent molecular weight of the circumsporozoite protein relative to the unmodified polypeptide chain.

The invention also features protein isoforms encoded by splice variants of the present invention. Such isoforms may have biological activities identical to or different from those possessed by the circumsporozoite proteins specified by any one of SEQ ID Nos: 2, 4, 6, 8, 10, 12, 14, 16, 18, 20 of the invention. Such isoforms may arise, for example, by alternative splicing of one or more circumsporozoite gene transcripts.

Full length proteins or fragments corresponding to one or more particular motifs and/or domains or to arbitrary sizes, for example, at least 5, 10, 20, 25, 50, 75 and 100, amino acids in length are within the scope of the present invention.

For example, isolated circumsporozoite polypeptides can be encoded by all or a portion of a nucleic acid sequence shown in any of the sequences shown in a SEQ ID Nos: 1, 3, 5, 7, 9, 11, 13, 15, 17, 19 of the invention. Isolated peptidyl portions of circumsporozoite proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a circumsporozoite polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") circumsporozoite protein.

In general, polypeptides referred to herein as having an activity (e.g., are "bioactive") of a circumsporozoite protein are defined as polypeptides which include an amino acid sequence encoded by all or a portion of the nucleic acid sequences shown in one of the subject SEQ ID Nos. 1, 3, 5, 7, 9, 11, 13, 15, 17, 19 and which mimic or antagonize all or a portion of the biological/biochemical activities of a naturally occurring circumsporozoite protein.

Other biological activities of the subject circumsporozoite proteins will be reasonably apparent to those skilled in the art. According to the present invention, a polypeptide has biological activity if it is a specific agonist or antagonist of a naturally-occurring form of an circumsporozoite protein, and if retains all of the inflammatory suppressing or deactivating properties of the naturally occurring protein.

Assays for determining whether a compound, e.g., a protein, such as a circumsporozoite protein or variant thereof, has one or more of the above biological activities include those assays, well known in the art, which are used for assessing circumsporozoite agonist and circumsporozoite antagonist activities.

Other preferred proteins of the invention are those encoded by the nucleic acids set forth in the section pertaining to nucleic acids of the invention. In particular, the invention provides fusion proteins, e.g., circumsporozoite-immunoglobulin fusion proteins. Such fusion proteins can provide, e.g., enhanced stability and solubility of circumsporozoite proteins and may thus be useful in therapy. Fusion proteins can also be used to produce an immunogenic fragment of a circumsporozoite protein. For example, the VP6 capsid protein of rotavirus can be used as an immunologic carrier protein for portions of the circumsporozoite polypeptide, either in the monomeric form or in the form of a viral particle. The nucleic acid sequences corresponding to the portion of a subject circumsporozoite protein to which antibodies are to be raised can be incorporated into a fusion gene construct which includes coding sequences for a late vaccinia virus structural protein to produce a set of recombinant viruses expressing fusion proteins comprising circumsporozoite epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a circumsporozoite protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple antigen peptide system for peptide-based immunization can also be utilized to generate an immunogen, wherein a desired portion of a circumsporozoite polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of circumsporozoite proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the circumsporozoite polypeptides of the present invention. For example, circumsporozoite polypeptides can be generated as glutathione-Stransferase (GST-fusion) proteins. Such GST-fusion proteins can enable easy purification of the circumsporozoite polypeptide, as for example by the use of glutathione-derivatized matrices (see, for example, Current Protocols in Molecular Biology, eds. Ausubel et al. (N.Y.: John Wiley & Sons, 1991)). Additionally, fusion of circumsporozoite polypeptides to small epitope tags, such as the FLAG or hemagluttinin tag sequences, can be used to simplify immunological purification of the resulting recombinant polypeptide or to facilitate immunological detection in a cell or tissue sample. Fusion to the green fluorescent protein, and recombinant versions thereof which are known in the art and available commercially, may further be used to localize circumsporozoite polypeptides within living cells and tissue.

The present invention further pertains to methods of producing the subject circumsporozoite polypeptides. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant circumsporozoite polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant circumsporozoite polypeptide is a fusion protein containing a domain which facilitates its purification, such as GST fusion protein.

Moreover, it will be generally appreciated that, under certain circumstances, it may be advantageous to provide homologs of one of the subject circumsporozoite polypeptides which function in a limited capacity as one of either an circumsporozoite agonist (mimetic) or a circumsporozoite antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of circumsporozoite proteins.

Homologs of each of the subject circumsporozoite proteins can be generated by mutagenesis, such as by discrete point mutation(s), or by truncation. For instance, mutation can give rise to homologs which retain substantially the same, or merely a subset, of the biological activity of the circumsporozoite polypeptide from which it was derived. Alternatively, antagonistic forms of the protein can be generated which are able to inhibit the function of the naturally occurring form of the protein.

The recombinant circumsporozoite polypeptides of the present invention also include homologs of the wildtype circumsporozoite proteins, such as versions of those protein which are resistant to proteolytic cleavage, as for example, due to mutations which alter ubiquitination or other enzymatic targeting associated with the protein.

Circumsporozoite polypeptides may also be chemically modified to create circumsporozoite derivatives by forming covalent or aggregate conjugates with other chemical moieties, such as glycosyl groups, lipids, phosphate, acetyl groups and the like. Covalent derivatives of circumsporozoite proteins can be prepared by linking the chemical moieties to functional groups on amino acid sidechains of the protein or at the N-terminus or at the C-terminus of the polypeptide.

Modification of the structure of the subject circumsporozoite polypeptides can be for such purposes as enhancing therapeutic or prophylactic efficacy, stability (e.g., ex vivo shelf life and resistance to proteolytic degradation), or post-translational modifications (e.g., to alter phosphorylation pattern of protein). Such modified peptides, when designed to retain at least one activity of the naturally-occurring form of the protein, or to produce specific antagonists thereof, are considered functional equivalents of the circumsporozoite polypeptides described in more detail herein. Such modified peptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2.sup.nd ed., Ed. by L. Stryer, W H Freeman and Co.: 1981). Whether a change in the amino acid sequence of a peptide results in a functional circumsporozoite homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject circumsporozoite proteins as well as truncation mutants, and is especially useful for identifying potential variant sequences (e.g., homologs). The purpose of screening such combinatorial libraries is to generate, for example, novel circumsporozoite homologs which can act as either agonists or antagonist, or alternatively, possess novel activities all together. Thus, combinatorially-derived homologs can be generated to have an increased potency relative to a naturally occurring form of the protein.

In one embodiment, the variegated circumsporozoite libary of circumsporozoite variants is generated by combinatorial mutagenesis at the nucleic acid level, and is encoded by a variegated gene circumsporozoite library. For instance, a mixture of synthetic oligonucleotides can be enzymatically ligated into gene sequences such that the degenerate set of potential circumsporozoite sequences are expressible as individual polypeptides, or alternatively, as a set of larger fusion proteins (e.g., for phage display) containing the set of circumsporozoite sequences therein.

There are many ways by which such libraries of potential circumsporozoite homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential circumsporozoite sequences. The synthesis of degenerate oligonucleotides is well known in the art (see for example, Narang, S A (1983) Tetrahedron 39:3; Itakura et al. (1981) Recombinant DNA, Proc 3.sup.rd Cleveland Sympos. Macromolecules, ed. A G Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386-390; Roberts et al. (1992) PNAS 89:2429-2433; Devlin et al. (1990) Science 249: 404-406; Cwirla et al.

(1990) PNAS 87: 6378-6382; as well as U.S. Pat. Nos. 5,223,409, 5,198,346, and 5,096,815).

Likewise, a library of coding sequence fragments can be provided for a circumsporozoite clone in order to generate a variegated population of circumsporozoite fragments for screening and subsequent selection of bioactive fragments. A variety of techniques are known in the art for generating such 1, including chemical synthesis. In one embodiment, a library of coding sequence fragments can be generated by (i) treating a double stranded PCR fragment of a circumsporozoite coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of circumsporozoite homologs. The most widely used techniques for screening large gene libraries typically comprises cloning the gene library into replicable expression vectors, transforming appropriate cells with the resulting libraries of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate circumsporozoite sequences created by combinatorial mutagenesis techniques. Combinatorial mutagenesis has a potential to generate very large libraries of mutant proteins, e.g., in the order of 1026 molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, PNAS USA 89:7811-7815; Yourvan et al., 1992, Parallel Problem Solving from Nature, 2., In Maenner and Manderick, eds., Elsevir Publishing Co., Amsterdam, pp. 401-410; Delgrave et al., 1993, Protein Engineering 6(3):327-331).

The invention also provides for use of the circumsporozoite proteins to generate mimetics, e.g., peptide or non-peptide agents, such as small molecules, which are able to disrupt binding of a circumsporozoite polypeptide of the present invention with a molecule, e.g. target peptide. Thus, such mutagenic techniques as described above are also useful to map the determinants of the circumsporozoite proteins which participate in protein-protein interactions involved in, for example, binding of the subject circumsporozoite polypeptide to a target molecule or receptor on an inflammatory cell. To illustrate, the critical residues of a subject circumsporozoite polypeptide which are involved in molecular recognition of its receptor can be determined and used to generate circumsporozoite derived peptidomimetics or small molecules which competitively inhibit binding of the authentic circumsporozoite protein with that moiety. By employing, for example, scanning mutagenesis to map the amino acid residues of the subject circumsporozoite proteins which are involved in binding other proteins, peptidomimetic compounds can be generated which mimic those residues of the circumsporozoite protein which facilitate the interaction. Such mimetics may then be used to interfere with the normal function of a circumsporozoite protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9.sup.th American Peptide Symposium) Pierce Chemical Co. Rockland, Ill., 1985), b-turn dipeptide cores (Nagai et al. (1985) Tetrahedron Lett 26:647; and Sato et al. (1986) J Chem Soc Perkin Trans 1:1231), and b-aminoalcohols (Gordon et al. (1985) Biochem Biophys Res Commun126:419; and Dann et al. (1986) Biochem Biophys Res Commun 134:71).

Therapeutic Methods

The invention herein further provides for the development of circumsporozoite polypeptides or homologs or fragments thereof, as described herein, as a therapeutic for the treatment of patients suffering from disorders, for example, inflammatory diseases, including but not limited to inflammatory liver diseases, autoimmune diseases or other inflammation-related diseases, disorders or conditions, such as arthritis, inflammatory bowel disease, or neurological disorders resulting from disease or injury. For example, inflammatory liver disease may result from infection with a bacteria, a virus, or a parasite. Alternatively, inflammatory liver disease may result from a cancerous condition or treatment with drugs that are hepatotoxic. Inflammatory liver disease can also result from chronic alcohol consumption. In addition, the circumsporozoite polypeptides or homologs or fragments thereof can be used for induction of tolerance to particular antigens, including autoantigens, alloantigens, or transplant antigens, or allergens, as described herein.

Methods of Administration

Methods known in the art for the therapeutic delivery of agents such as proteins or nucleic acids can be used for the therapeutic delivery of a circumsporozoite polypeptide or a nucleic acid encoding such polypeptide of the invention for treating a deleterious condition or disease in a subject, e.g., cellular transfection, gene therapy, direct administration with a delivery vehicle or pharmaceutically acceptable carrier, indirect delivery by providing recombinant cells comprising a nucleic acid encoding a fusion polypeptide of the invention.

Various delivery systems are known and can be used to administer the circumsporozoite polypeptide of the invention, e.g., encapsulation in liposomes, microparticles, microcapsules, microspheres, recombinant cells capable of expressing the protein, receptor-mediated endocytosis (see, e.g., Wu and Wu, 1987, J. Biol. Chem. 262:4429-4432), construction of a nucleic acid as part of a retroviral or other vector, etc.

Methods of introduction can be enteral or parenteral and include but are not limited to intradermal, intramuscular, intraperitoneal, intravenous, subcutaneous, pulmonary, intranasal, intraocular, epidural, and oral routes. In one particular embodiment, the CSP is administered intravenously via the portal vein along with an antigen for which tolerance is desired. The proteins may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

Delivery of the CSP or homolog or fragment thereof to an inflammatory cell may be accomplished by attachment to a ligand that is recognized by a receptor (for example, an endocytic receptor) on the inflammatory cell, such as a macrophage, monocyte, Kupffer cell, neutrophil or eosinophil, and may be by any suitable means, including but not limited to covalent attachment by means of a bifunctional cross-linking reagent, and activation of one member and then cross-linking to a functional group on the other. Various cross-linking agents and functional group activating agents such as described from Pierce Chemical Co., Rockford, Ill., are useful for these purposes. In the instance wherein both the endocytic receptor-binding molecule/ligand and the agent that reduces the activity or function of the inflammatory cell are proteins or peptides, they may be expressed on a single polypeptide chain, wherein the single polypeptide chain retains the endocytic receptor-binding activity and the protein or peptide retains its desired features.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, fibers, or commercial skin substitutes.

In another embodiment, the active agent can be delivered in a vesicle, in particular a liposome (see Langer (1990) Science 249:1527-1533). Liposomes are synthetic, single or multi-compartmental vesicles having lipid or lipid/polymer membranes enclosing aqueous chambers. It is to be understood that wherever the term "lipid" is used herein, it also includes "lipid/polymer" as an alternative. There are at least three types of liposomes. "Multilamellar liposomes or vesicles (MLV)" have multiple "onion-skin" concentric lipid membranes, in between which are shell-like concentric aqueous compartments. "Unilamellar liposomes or vesicles (ULV)" refers to liposomal structures having a single aqueous chamber. "Multivesicular liposomes (MVL)" are lipid vesicles comprising lipid membranes enclosing multiple, non-concentric aqueous compartments.

Preparation of liposomes containing proteins or nucleic acids are described in U.S. patent publication numbers 2003/0026831, U.S. 2002/0182225 and 2002/0012699, all of which are incorporated by reference in their entireties. Furthermore, methods for incorporating, i.e., reconstituting, proteins into liposomes are known in the art. See Rigaud, J-L., et al., "Liposomes as Tools for the Reconstitution of Biological Systems," p. 71-88, in Liposomes as Tools in Basic Research and Industry, ed. Philippot, J. R. and Schuber, F., CRC Press, Boca Raton, Fla. (1995).

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject. For example, smooth muscle cells can be targeted with an antibody binding specifically to SM22a, a smooth muscle cell marker. Retinal cells and RPE cells can similarly be targeted.

In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

Any means for the introduction of polynucleotides into mammals, human or non-human, may be adapted to the practice of this invention for the delivery of the various constructs of the invention that encode a circumsporozoite protein or homolog or fragment thereof into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al. Colloidal dispersion systems.

In a preferred method of the invention, the DNA constructs are delivered using viral vectors. The transgene may be incorporated into any of a variety of viral vectors useful in gene therapy, such as recombinant retroviruses, adenovirus, adeno-associated virus (.AAV), and herpes simplex virus-1, or recombinant bacterial or eukaryotic plasmids. While various viral vectors may be used in the practice of this invention, AAV- and adenovirus-based approaches are of particular interest. Such vectors are generally understood to be the recombinant gene delivery system of choice for the transfer of exogenous genes in vivo, particularly into humans. The following additional guidance on the choice and use of viral vectors may be helpful to the practitioner. As described in greater detail below, such embodiments of the subject expression constructs are specifically contemplated for use in various in vivo and ex vivo gene therapy protocols.

Nucleic Acid Construction and Expression of CSP Polypeptides

Individual components of the fusion polypeptides of the invention may be produced from nucleic acids molecules using molecular biological methods known to the art. Nucleic acid molecules are inserted into a vector that is able to express the polypeptides when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the polypeptides of the invention under control of transcriptional/translational control signals. These methods may include in vitro recombinant DNA and synthetic techniques and in vivo recombinations (See Sambrook et al. *Molecular Cloning, A Laboratory Manual*, Cold Spring Harbor Laboratory; Current Protocols in Molecular Biology, Eds. Ausubel, et al., Greene Publ. Assoc., Wiley-Interscience, NY).

Expression of the nucleic acid molecules of the invention may be regulated by a second nucleic acid sequence so that the molecule is expressed in a host transformed with the recombinant DNA molecule. For example, expression of the nucleic acid molecules of the invention may be controlled by any promoter/enhancer element known in the art. Promoters which may be used to control expression of the fusion polypeptide molecules include, but are not limited to, the long terminal repeat as described in Squinto et al. (1991) Cell 65:1-20; the SV40 early promoter region, the CMV promoter, the M-MuLV 5' terminal repeat the promoter contained in the 3' long terminal repeat of Rous sarcoma virus, the herpes thymidine kinase promoter, the regulatory sequences of the metallothionine gene; prokaryotic expression vectors such as the β-lactamase promoter, or the tac promoter (see also "Useful proteins from recombinant bacteria" in Scientific American (1980) 242:74-94); promoter elements from yeast or fungi such as the Gal 4 promoter, the ADH (alcohol dehydrogenase) promoter, PGK (phosphoglycerol kinase) promoter, alkaline phosphatase promoter, and tissue-specific transcriptional control regions derived from elastase I gene, insulin gene, immunoglobulin gene, mouse mammary tumor virus, albumin gene, α-fetoprotein gene, α1-antitrypsin gene, β-globin gene, myelin basic protein gene, myosin light chain-2 gene, and gonadotropic releasing hormone gene.

The nucleic acid constructs of the invention are inserted into an expression vector or viral vector by methods known to the art, wherein the nucleic acid molecule is operatively linked to an expression control sequence. Also provided is a host-vector system for the production of a tissue-specific fusion polypeptide of the invention, which comprises the expression vector of the invention, which has been introduced into a host cell suitable for expression of the fusion polypeptide. The suitable host cell may be a bacterial cell such as *E. coli*, a yeast cell, such as *Pichia pastoris*, an insect cell, such as *Spodoptera frugiperda*, or a mammalian cell, such as a COS, CHO, 293, BHK or NS0 cell.

The invention further encompasses methods for producing the polypeptides of the invention by growing cells transformed with an expression vector under conditions permitting production of the polypeptides and recovery of the polypeptides so produced. Cells may also be transduced with a recombinant virus comprising the nucleic acid construct of the invention.

The polypeptides may be purified by any technique, which allows for the subsequent formation of a stable polypeptide. For example, and not by way of limitation, the polypeptides may be recovered from cells either as soluble polypeptides or as inclusion bodies, from which they may be extracted quantitatively by 8M guanidinium hydrochloride and dialysis. In order to further purify the polypeptides, conventional ion exchange chromatography, hydrophobic interaction chromatography, reverse phase chromatography or gel filtration may be used. The polypeptides may also be recovered from conditioned media following secretion from eukaryotic or prokaryotic cells.

Cellular Transfection and Gene Therapy

The present invention encompasses the use of nucleic acids encoding the polypeptides of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell. The compositions are administered to a subject in an amount sufficient to elicit a therapeutic response.

In another aspect, the invention provides a method of treating a target site, i.e., a target cell or tissue, in a human or other animal comprising transfecting a cell with a nucleic acid encoding a polypeptide of the invention, wherein the nucleic acid comprises an inducible promoter operably linked to the nucleic acid encoding the fusion polypeptide. For gene therapy procedures in the treatment or prevention of human disease, see for example, Van Brunt (1998) Biotechnology 6:1149-1154. Non-limiting examples of techniques which can be used to introduce an expression vector encoding the fusion polypeptides into a host cell are described below.

Adenovirus-Polylysine DNA Complexes: Naked DNA can be introduced into cells by complexing the DNA to a cation, such as polylysine, which is then coupled to the exterior of an adenovirus virion (e.g., through an antibody bridge, wherein the antibody is specific for the adenovirus molecule and the polylysine is covalently coupled to the antibody) (see Curiel et al. (1992) Human Gene Therapy 3:147-154). Entry of the DNA into cells exploits the viral entry function, including natural disruption of endosomes to allow release of the DNA intracellularly. A particularly advantageous feature of this approach is the flexibility in the size and design of heterologous DNA that can be transferred to cells.

Receptor-Mediated DNA Uptake: Naked DNA can also be introduced into cells by complexing the DNA to a cation, such as polylysine, which is coupled to a ligand for a cell-surface receptor (see for example Wu et al. (1988) J. Biol. Chem. 263:14621; Wilson et al. (1992) J Biol. Chem. 267:963-967; and U.S. Pat. No. 5,166,320). Binding of the DNA-ligand complex to the receptor facilitates uptake of the DNA by receptor-mediated endocytosis. Receptors to which a DNA-ligand complex have targeted include the transferrin receptor and the asialoglycoprotein receptor. Additionally, a DNA-ligand complex can be linked to adenovirus capsids which naturally disrupt endosomes, thereby promoting release of the DNA material into the cytoplasm and avoiding degradation of the complex by intracellular lysosomes (see for example Curiel et al. (1991) Proc. Natl. Acad. Sci. USA 88:8850; and Cotten et al. (1992) Proc. Natl. Acad. Sci. USA 89:6094-6098; Wagner et al. (1992) Proc. Natl. Acad. Sci. USA 89:6099-6103). Receptor-mediated DNA uptake can be used to introduce DNA into cells either in vitro or in vivo and, additionally, has the added feature that DNA can be selectively targeted to a particular cell type by use of a ligand which binds to a receptor selectively expressed on a target cell of interest.

Liposome-Mediated transfection ("lipofection"): Naked DNA can be introduced into cells by mixing the DNA with a liposome suspension containing cationic lipids. The DNA/liposome complex is then incubated with cells. Liposome mediated transfection can be used to stably (or transiently) transfect cells in culture in vitro. Protocols can be found in Current Protocols in Molecular Biology, Ausubel, F. M. et al. (eds.) Greene Publishing Associates, (1989), Section 9.4 and other standard laboratory manuals. Additionally, gene delivery in vivo has been accomplished using liposomes. See for example Nicolau et al. (1987) Meth. Enz. 149:157-176; Wang and Huang (1987) Proc. Natl. Acad. Sci. USA 84:7851-7855; Brigham et al. (1989) Am. J Med. Sci. 298:278; and Gould-Fogerite et al. (1989) Gene 84:429-438.

Direct Injection: Naked DNA can be introduced into cells by directly injecting the DNA into the cells. For an in vitro culture of cells, DNA can be introduced by microinjection, although this not practical for large numbers of cells. Direct injection has also been used to introduce naked DNA into cells in vivo (see e.g., Acsadi et al. (1991) Nature 332:815-818; Wolff et al. (1990) Science 247:1465-1468). A delivery apparatus (e.g., a "gene gun") for injecting DNA into cells in vivo can be used. Such an apparatus is commercially available (e.g., from BioRad).

Retroviral Mediated Gene Transfer: Defective retroviruses are well characterized for use in gene transfer for gene therapy purposes (for a review see Miller, A. D. (1990) Blood 76:271). A recombinant retrovirus can be constructed having a nucleic acid encoding a gene of interest (e.g., an antibody homologue) inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art.

Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J Immunol. 150:4104-4115; U.S. Pat. Nos. 4,868,116; 4,980,286; WO 89/07136; WO 89/02468; WO 89/05345; and WO 92/07573). While any retrovirus may be utilized, the lentivirus approach allows for delivery to a broad variety of cellular targets, both ex vivo (cell lines, primary cells including stem cells, fertilized oocytes, and blastocysts) and in vivo (e.g., brain, lung, liver). The lentivirus vector-mediated delivery of siRNAs allows for the controllable suppression of cellular genes both with a high degree of efficacy and without significant leakiness.

Adenoviral Mediated Gene Transfer: The genome of an adenovirus can be manipulated such that it encodes and expresses a gene product of interest (e.g., an antibody homologue) but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482-6486), hepatocytes (Herz and Gerard (1993) Proc. Natl. Acad. Sci. USA 90:2812-2816) and muscle cells (Quantin et al. (1992) Proc. Natl. Acad. Sci. USA 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to many other gene delivery vectors (Berkner et al. cited supra; Haj-Ahmand and Graham (1986) J Virol. 57:267). Most replication-defective adenoviral vectors currently in use are deleted for all or parts of the viral E1 and E3 genes but retain as much as 80% of the adenoviral genetic material.

Adeno-Associated Viral Mediated Gene Transfer: Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97-129). It is also one of the few viruses that may integrate its DNA into non-dividing cells, and exhibits a high frequency of stable integration (see for example Flotte et al. (1992) Am. J Respir. Cell. Mol. Biol. 7:349-356; Samulski et al. (1989) J Virol. 63:3822-3828; and McLaughlin et al. (1989) J Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J Virol. 51:611-619; and Flotte et al. (1993) J Biol. Chem. 268:3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of the introduced DNA can be detected, for example, by Northern blotting, RNase protection or reverse transcriptase-polymerase chain reaction (RT-PCR). Expression of the introduced gene product (e.g., the antibody homologue) in the cell can be detected by an appropriate assay for detecting proteins, for example by immunohistochemistry.

As will be appreciated by those skilled in the art, the choice of expression vector system will depend, at least in part, on the host cell targeted for introduction of the nucleic acid. For example, nucleic acid encoding a polypeptide is preferably introduced into tissues containing inflammatory cells.

The functional outcome of expression of the polypeptides can be assessed by suitable assays that monitor the expression and/or function of the target protein, including standard immunohistochemistry or immunoelectron microscopy techniques.

Alternatively, macrophage activity or function can be measured by many procedures known to those skilled in the art, for example, by monitoring respiratory burst activity by chemiluminescence, or by monitoring second messenger activity such as cAMP or IP3, or by measuring inflammatory cytokine activity including but not limited to IL-1, Il-6 or TNF activity and suppression of their expression or release upon treatment of the cell or subject with a CSP or homolog thereof. These can all be measured using commercially available assays. In addition, the functional outcome of expression of a polypeptide can also be assessed in vivo using animal model systems that may be predictive of therapeutic efficacy in humans.

Combination Therapies

In numerous embodiments, the polypeptides of the present invention may be administered in combination with one or more additional compounds or therapies. For example, the CSP polypeptide or nucleic acid encoding the polypeptide can be co-administered in conjunction with one or more therapeutic compounds, in particular, any compound or agent that helps to maintain the tolerogenic state. Examples of such compounds are cyclosporine A, rapamycin, sirolimus, and tacrolimus or corticosteroids. The combination therapy may encompass simultaneous or alternating administration. In addition, the combination may encompass acute or chronic administration.

Pharmaceutical Compositions

The present invention also provides pharmaceutical compositions comprising a CSP polypeptide of the invention or a homolog or fragment thereof and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the polypeptide of the invention which will be effective in the treatment of a condition or disease can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20-5000 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Screening for Novel CSP Analogs, Fragments, Derivatives or Mimics Candidate Compounds and Agents As used herein, the term "candidate compound" or "candidate therapeutic" or "test compound" or "agent" or "test agent" refers to any compound or molecule that is to be tested (for example, CSP analogues, derivatives, variants, or mimics or fragments thereof). As used herein, the terms, which are used interchangeably, refer to biological or chemical compounds such as simple or complex organic or inorganic molecules, peptides, proteins, peptidomimetics, peptide mimics, antibodies, oligonucleotides, polynucleotides (e.g., DNA and RNA), carbohydrates, lipoproteins, lipids, small molecules and other drugs. A vast array of compounds can be synthesized, for example oligomers, such as oligopeptides and oligonucleotides, and synthetic organic compounds based on various core structures, and these are also included in the terms noted above. In addition, various natural sources can provide compounds for screening, such as plant or animal extracts, and the like. Compounds can be tested singly or in combination with one another. Agents or candidate compounds can be randomly selected or rationally selected or designed. As used herein, an agent or candidate compound is said to be "randomly selected" when the agent is chosen randomly without considering the specific interaction between the agent and the target compound or site. As used herein, an agent is said to be "rationally selected or designed", when the agent is chosen on a nonrandom basis which takes into account the specific interaction between the agent and the target site and/or the conformation in connection with the agent's action. Moreover, the agent may be selected by its effect on the gene expression profile obtained from screening in vitro or in vivo. For example, the gene expression data for activated or suppressed macrophages or monocytes (including Kupffer cells) can be accessed online through databases including Pub Med, Human Genome Project (HGP), Gene Bank and PDB (Protein Data Bank). Furthermore, candidate compounds can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. Nos. 5,738,996; and 5,807,683).

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented, e.g., presented in solution (e.g., Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) orphage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310).

If the screening for compounds that modulate the activity or function of a macrophage, including, but not limited to, a Kupffer cell, is done with a library of compounds, it may be necessary to perform additional tests to positively identify a compound that satisfies all required conditions of the screening process. There are multiple ways to determine the identity of the compound. One process involves mass spectrometry, for which various methods are available and known to the skilled artisan (see for instance neogenesis.com).

Screening/Testing for Active CSP Candidate Proteins, Analogues and Peptide Mimics Any screening technique known in the art can be used to screen for active CSP peptides or mimics of CSP that inhibit macrophage activation or that suppress macrophage function. The present invention contemplates screens for small molecule mimics, as well as screens for natural proteins or peptides that bind to and inhibit such macrophage activity in vitro or in vivo. For example, natural products or peptide libraries can be screened using assays of the invention for molecules that have the ability to alter the cytokine profile from macrophages, eg. inhibit the expression, production and/or release of pro-inflammatory cytokines or enhance the expression, production and/or release of anti-inflammatory cytokines from macrophages, or that inhibit the respiratory burst from macrophages using the methods described in the Examples.

Identification and screening of a molecule is further facilitated by determining structural features of the protein, e.g., using X-ray crystallography, neutron diffraction, nuclear magnetic resonance spectrometry, and other techniques for structure determination. These techniques provide for the rational design or identification of proteins, or peptide fragments that have an inhibitory effect on macrophage activity or function. For example, it is envisioned that CSP, or a CSP-derived peptide, or analogue, or active fragment thereof may be crystallized together with LRP to determine the interacting domains.

Another approach uses recombinant bacteriophage to produce large libraries. Using the "phage method" [Scott and Smith, 1990, Science 249:386-390 (1990); Cwirla, et al., Proc. Natl. Acad. Sci., 87:6378-6382 (1990); Devlin et al., Science, 249:404-406 (1990)], very large libraries can be constructed ($10^6$-$10^8$ chemical entities). A second approach uses primarily chemical methods, of which the Geysen method [Geysen et al., Molecular Immunology 23:709-715 (1986); Geysen et al. J. Immunologic Method 102:259-274 (1987)] and the method of Fodor et al. [Science 251:767-773 (1991)] are examples. Furka et al. [14th International Congress of Biochemistry, Volume 5, Abstract FR:013 (1988); Furka, Int. J. Peptide Protein Res. 37:487-493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as activators or inhibitors.

Screening phage-displayed random peptide libraries offers a rich source of molecular diversity and represents a powerful means of identifying peptide ligands that bind a receptor molecule of interest (Cwirla, et al., Proc. Natl. Acad. Sci., 87:6378-6382 (1990); Devlin et al., Science, 249:404-406 (1990)). Phage expressing binding peptides are selected by affinity purification with the target of interest. This sytem allows a large number of phage to be screened at one time. Since each infectious phage encodes the random sequence expressed on its surface, a particular phage, when recovered from an affinity matrix, can be amplified by another round of infection. Thus, selector molecules immobilized on a solid support can be used to select peptides that bind to them. This procedure reveals a number of peptides that bind to the selector and that often display a common consensus amino acid sequence. Biological amplification of selected library members and sequencing allows the determination of the primary structure of the peptide(s).

Peptides are expressed on the tip of the filamentous phage M13, as a fusion protein with the phage surface protein pilus (at the N-terminus). Typically, a filamentous phage carries on its surface 3 to 5 copies of pili and therefore of the peptide. In such a system, no structural constraints are imposed on the N-terminus; the peptide is therefore free to adopt many different conformations, allowing for a large diversity. However, biases in the distribution of peptides in the library may be caused by biological selection against certain of the peptides, which could reduce the diversity of peptides contained in the library. In practice, this does not appear to be a significant problem. When randomly selected peptides expressed at the N-terminus of pili were analyzed (Cwirla, et al., *Proc. Natl. Acad. Sci.*, 87:6378-6382 (1990)), most amino acids appeared at each position of the variable peptide, indicating that no severe discrimination against particular amino acids had occurred. Selection against particular combinations of amino acids would however not have been detected in this analysis.

In another aspect, synthetic libraries [Needels et al., *Proc. Natl. Acad. Sci. USA* 90:10700-4 (1993); Ohlmeyer et al., *Proc. Natl. Acad. Sci. USA* 90:10922-10926 (1993); Lam et al., International Patent Publication No. WO 92/00252; Kocis et al., International Patent Publication No. WO 9428028, each of which is incorporated herein by reference in its entirety], and the like can be used to screen for novel peptides or mimics thereof or fragments thereof according to the present invention.

Alternatively, the effect of a candidate CSP analogue or candidate fragment thereof may be tested on macrophages obtained from tissues, or blood, or on a macrophage cell line, such as the RAW264.7 cell line or the U937 cell line. For example, one may assess the effects of the candidate CSP analogue, mimic, or active fragment thereof, on the cytokine profile (on the gene or protein) in these cells, or on release of one or more cytokines from these cells. A positive candidate would alter the cytokine profile such that the pro-inflammatory cytokines (such as but not limited to IL-6, IL-12, TNF alpha) would be reduced and the anti-inflammatory cytokines (such as but not limited to IL-10) would be increased. The candidate CSP analogues or mimics can be provided as recombinant or synthetic proteins.

The methods used to measure the effect of the candidate CSP analogue or mimic on macrophages, more particularly, on the cytokine expression profile, may include standard procedures known to those skilled in the art. For example, the level of expression of a gene or gene product (protein) may be determined by a method selected from, but not limited to, cDNA microarray, reverse transcription-polymerase chain reaction (RT-PCR), real time PCR and proteomics analysis. Other means such as electrophoretic gel analysis, enzyme immunoassays (ELISA assays), Western blots, dotblot analysis, Northern blot analysis and in situ hybridization may also be contemplated for use, although it is to be understood that the former assays that are noted (eg. micrarrays, RT-PCR, real time PCR and proteomics analysis) provide a more sensitive, quantitative and reliable measurement of genes or gene products that are modulated by a candidate CSP or an analogue, mimic or fragment thereof. Sequences of the genes or cDNA from which probes are made (if needed) for analysis may be obtained, e.g., from GenBank.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Effect of Malaria Circumsporozoite Protein on Kupffer Cells (Liver Macrophages)

Materials and Methods

Materials. Heparinase, heparitinase and chondroitinase ABC were from Seikagaku (Falmouth, Mass.), collagenase H was from Boehringer (Indianapolis, Ind.). Recombinant human RAP was purchased from Innovative Research (Southfield, Mich.). The mAb 8B8 against the 85 kDa light chain of LRP-1 was from Maine Biotechnology Services (Portland, Me.). Goat anti-mouse IgG conjugated to fluorescein isothiocyanate (FITC) was from Chemicon (Temecula, Calif.), protein A-FITC and protein G-Alexa 488 were from Molecular Probes (Eugene, Oreg.). Zymosan A (*Saccharomyces cerevisiae*), 12-O-tetradecanoylphorbol-13-acetate (PMA), type I collagen, lactoferrin (LF; from bovine colostrum), luminol (5-amino-2,3-dihydro-1,4-phthalazinedione), lucigenin (N,N'-Dimethyl-9,9'-biacridinium dinitrate), dibutyryl cAMP (db-cAMP), 9-(Tetrahydro-2-furanyl)-9H-purin-6-amine (SQ 22,536), N-[2-(p-Bromocinnamylamino) ethyl]-5-isoquinolinesulfonamide dihydrochloride (H89), Rp-cAMPS triethylammonium salt (Rp-cAMP) and 3-isobutyl-1 methylxanthine (IBMX) were purchased from Sigma (St. Louis, Mo.). Myristoylated protein kinase A inhibitor amide 14-22 ($PKI_{14-22}$) was from Calbiochem (San Diego, Calif.). Heparin Sepharose 6 Fast Flow and Percoll were from Amersham (Piscataway, N.J.), Ni-NTA Superflow resin was from Qiagen Inc. (Valencia, Calif.). Detoxi-Gel AffinityPak pre-packed columns were from Pierce (Rockford, Ill.). The PKA and EPAC activators 8-[4-chlorophenylthio]-2'-O-methyladenosine-3',5'-cAMP (8-CPT-2-Me-cAMP) and $N_6$-monobutyryladenosine-3',5'-cAMP (6-MB-cAMP) were from BioLog (Life Science, Arlington Heights, Ill.).

Purification of recombinant CSP. The *P. falciparum* CS protein CS27IVC-$His_6$ (AA 27-123$[NANPNVDP]_3$ $[NANP]_{21}$300-411) was expressed in *Escherichia coli* and purified by two step affinity chromatography using Ni-NTA Superflow and Heparin Sepharose 6 Fast Flow resins (Stüber D, Matile H, Garotta G (1990) System for high-level production in *Escherichia coli* and rapid purification of recombinant proteins: application to epitope mapping, preparation of antibodies, and structure—function analysis. Immunol. Methods IV: 121-152; Takacs B J, Girard M-F (1991) Preparation of clinical grade proteins produced by recombinant DNA technologies. J.Immunol. Methods 143: 231-240). The protein comprises amino acid sequences representing region I and II-plus as well as the complete repeat region from the T4 isolate (Cerami C, Frevert U, Sinnis P, Takacs B, Clavijo P, et al. (1992) The basolateral domain of the hepatocyte plasma membrane bears receptors for the circumsporozoite protein of *Plasmodium falcipanum* sporozoites. Cell 70: 1021-1033). The plasmid encoding the construct was kindly provided by Drs. Bela Takacs and Dietrich Stüber (F. Hoffmann-La Roche Ltd., Basel, Switzerland). To exclude a potential effect of LPS on ROS formation, we tested our recombinant CSP preparations for contamination with LPS using a *Limulus* amebocyte lysate assay (E-TOXATE Kit, Sigma) according to the instructions of the supplier. The final concentration of LPS in the experiments with recombinant CSP was less than 0.06 EU/ml. LPS was removed using polymyxin B-agarose prepacked columns (Detoxi-Gel, Pierce) according to manufacturer's instructions.

*Plasmodium* sporozoite purification. *P. berghei* or *P. yoelii* sporozoites were isolated from infected *Anopheles stephensi* salivary glands. As a control, extracts from uninfected salivary glands were prepared in an identical fashion.

Liver cell isolation. Liver cells were isolated from female Sprague Dawley rats (230-250 g). Livers were perfused with collagenase as described by Neufeld (Neufeld DS (1997) Isolation of rat liver hepatocytes. Methods in Molecular Biology, Vol 75: Basic Cell Culture Protocols 75: 145-151). Subsequently, liver cells were purified by a combined differential and Percoll gradient centrifugation using a Sorvall HS4 swinging bucket rotor (Smedsrod B, Pertoft H (1985) Preparation of pure hepatocytes and reticuloendothelial cells in high yield from a single rat liver by means of Percoll centrifugation and selective adherence. J.Leukocyte Biol 38: 213-230). After filtration through a 100-μm mesh polypropylene filter (Spectra/Mesh; Spectrum, Laguna Hills, Calif.), the cell suspension was centrifuged for 5 minutes at 50 g resulting in a hepatocyte-enriched pellet and a nonparenchymal cell-enriched supernatant. The nonparenchymal cell-containing supernatant was saved. The pellet was resuspended in ice-cold phosphate-buffered saline (PBS) and mixed in an equal volume of PBS-buffered isotonic Percoll. The gradient was centrifuged for 10 minutes at 50 g. The pellet was resuspended in PBS, centrifuged again, and the final pellet was resuspended in RPMI 1640 medium containing 10% FCS. The nonparenchymal cell-enriched supernatants were centrifuged for 15 minutes at 900 g. The pellet was resuspended in ice-cold PBS, layered over a 2-cushion Percoll gradient (Smedsrod B, Pertoft H (1985) Preparation of pure hepatocytes and reticuloendothelial cells in high yield from a single rat liver by means of Percoll centrifugation and selective adherence. J.Leukocyte Biol 38: 213-230) and centrifuged for 30 minutes at 900 g. The intermediate zone, containing mostly liver endothelial cells, and the bottom cushion, containing mostly Kupffer cells, were saved, mixed with PBS, and centrifuged for 15 minutes at 900 g. The pellet was resuspended in PBS with 1% FCS and the cells further separated into various fractions by centrifugal counterflow elutriation (Knook D L, Sleyster E C (1976) Separation of Kupffer and endothelial cells of the rat liver by centrifugal elutriation. Exp Cell Res 99: 444-449) using the Beckman Coulter JE-5.0 elutriator rotor supplied with a Sanderson chamber (Beckman Coulter, Palo Alto, Calif. USA). The cell suspension was introduced into the elutriator at a flow rate of 12 ml/min, and the elutriator speed set to 3250 rpm. Endothelial cells were obtained at a 32 ml/min flow rate, whereas Kupffer cells were collected at 70 ml/min. The cells were centrifuged at 200 g and resuspended in RPMI-1640 medium containing 10% fetal calf serum. The cell purity and viability were above 95% as determined by peroxidase stain and trypan blue exclusion.

Cell culture. Kupffer cells were seeded into 96-well microtiter plates ($0.25 \times 10^6$ cells/well) or 24-well plates ($1.0 \times 10^6$ cells/well). Endothelial cells were plated on 24-well plates ($1.5 \times 10^6$ cells/well), which had been previously coated with type I collagen (Sigma, St. Louis, Mo.). Rat hepatocytes and HepG2 cells (# HB-8065, ATCC, Rockville, Md.) were seeded at a density of $1 \times 10^5$ cells/cm$^2$ into Matrigel-coated (BD Biosciences, Bedford, Mass.) 12-well or 24-well plates (Nunc, Napierville, Ill.). All types of cells were cultivated in RPMI 1640 medium supplemented with 10% fetal calf serum (FCS), 25 mM HEPES, and antibiotics (100 U/ml penicillin G and 100 μg/ml streptomycin sulfate) at 37° C. in 5% $CO_2$. Nonadherent cells were removed after 1 h by replacing medium, and the cells were cultured in the same medium for 18 h and then in RPMI-1640 without FCS for 6 h. HepG2 cells were used on day 3 after plating.

Cell treatment. To study the effect of CSP on cell signaling, the cells were incubated with different concentration of CSP for 0-90 min at 37° C. in 5% $CO_2$. Before use, CSP was dialyzed extensively with 150 mM NaCl, 10 mM HEPES, pH 7.4 and diluted in culture medium. To inhibit GAG sulfation, the cells were cultivated for 18 h in a mixture (4:1) of low sulfate Ham's F-12 medium and RPMI-1640, containing 20 mM sodium chlorate and 2% desalted FCS. In wells with 20 mM chlorate, an appropriate amount of medium was replaced with water in order to maintain normal osmolarity (Pinzon-Ortiz C, Friedman J, Esko J, Sinnis P (2001) The binding of the circumsporozoite protein to cell surface heparan sulfate proteoglycans is required for *Plasmodium* sporozoite attachment to target cells. J Biol Chem 276: 26784-26791). For digestion of cell surface GAGs, the cells were treated with 20 mU/ml heparinase, 20 mU/ml heparitinase, and 500 mU/ml chondroitinase ABC in the medium without FCS for 3 h (Shakibaei M, Frevert U (1996) Dual interaction of the malaria circumsporozoite protein with the low density lipoprotein receptor-related protein (LRP) and cell surface heparan sulfate. J Exp Med 184: 1699-1711). To prevent binding of CSP to LRP-1, the cells were incubated with 500 nM of recombinant receptor associated protein (RAP) for 10 min before addition of CSP. To inhibit adenylyl cyclase, the cells were incubated 10 min with 100 μM SQ 22,536 before addition of sporozoites or CSP. To inhibit PKA, the cells were incubated for 30 min with 10 μM H-89, 10 μM PKI$_{14-22}$, or 200 μM Rp-cAMP (Aronoff D M, Canetti C, Serezani C H, Luo M, Peters-Golden M (2005) Cutting edge: macrophage inhibition by cyclic AMP (cAMP): differential roles of protein kinase A and exchange protein directly activated by cAMP-1. J Immunol 174: 595-599; Nogueira-Machado J A, Lima e Silva F C, Medina L O, Costa D C, Chaves M M (2003) Modulation of the reactive oxygen species (ROS) generation mediated by cyclic AMP-elevating agents or Interleukin 10 in granulocytes from type 2 diabetic patients (NIDDM): a PKA-independent phenomenon. Diabetes Metab 29: 533-537; Sozzani P, Cambon C, Vita N, Seguelas M H, Caput D, et al. (1995) Interleukin-13 inhibits protein kinase C-triggered respiratory burst in human monocytes. Role of calcium and cyclic AMP. J Biol Chem 270: 5084-5088; Orlic T, Loomis W H, Shreve A, Namiki S, Junger W G (2002) Hypertonicity increases cAMP in PMN and blocks oxidative burst by PKA-dependent and -independent mechanisms. Am J Physiol Cell Physiol 282: C1261-1269; Makranz C, Cohen G, Reichert F, Kodama T, Rotshenker S (2006) cAMP cascade (PKA, Epac, adenylyl cyclase, Gi, and phosphodiesterases) regulates myelin phagocytosis mediated by complement receptor-3 and scavenger receptor-AI/II in microglia and macrophages. Glia 53: 441-448; Lin P, Welch E J, Gao X P, Malik A B, Ye R D (2005) Lysophosphatidylcholine modulates neutrophil oxidant production through elevation of cyclic AMP. J Immunol 174: 2981-2989). The selective activators 8-CPT-2-Me-cAMP and 6-MB-cAMP were used to stimulate PKA and EPAC, respectively (Christensen et al., (2003), cAMP analog mapping of Epac1 and cAMP kinase. Discriminating analogs demonstrate thet Epac and cAMP kinase act synergistically to promote PC-12 cell neurite extension. J. Biol. Chem. 278: 35394-35402; Kang et al., (2003), Epac-selective cAMP analog 8-pCPT-2'-O-Me-cAMP as a stimulus for Ca2+ release and exocytosis in pancreatic beta cells, J. Biol. Chem. 278: 8279-8285). In some experiments, 3-isobutyl-1 methylxanthine (IBMX) or dibutyryl cAMP (db-cAMP) was added to the cells 30 min before measuring. IBMX and db-cAMP were used at a final concentration of 1 mM. IBMX was dissolved in dimethyl sulphoxide (DMSO). The final concentration of DMSO in culture medium did not exceed 0.1%. All other additives were dissolved in culture medium and were added as indicated in the figure legends. To study the effect of sporozoites on signaling, freshly isolated sporozoites were added to Kupffer cells at a ratio of 2:1. As a control, Kupffer cells were incubated with extracts from uninfected salivary glands.

cAMP radioimmunoassay. For cAMP determination, liver cell cultures were incubated in culture medium without FCS at 37° C. for 0-90 min. The cultures were then placed on ice, and the reaction was stopped by aspiration of the incubation medium followed by the addition of 1 ml of ice cold 65% (vol/vol) ethanol. The cells were scraped into Eppendorf tubes and centrifuged at 10000 g for 10 min at 4° C. The supernatants were dried in SC110 Speedvac Concentrator (Savant, Farmingdale, N.Y.) at room temperature, and the dried extracts were dissolved in assay buffer for cAMP determination with cAMP [$^{125}$I] Direct Biotrak Assay from Amersham Biosciences (Piscataway, N.J.), according to the instructions of the manufacturer. Samples were analyzed with a Beckman LS 6000 scintillation counter. The cAMP level in each sample was normalized to the protein concentration and expressed as fmol/µg of protein. Ethanol-precipitated cell pellets were diluted with 0.15 M NaOH and the protein concentration was measured with the Micro BCA Protein Assay Kit (Pierce Chemical Co., Rockford, Ill.) according to manufacturer's instructions.

Inositol-1,4,5-trisphosphate ($IP_3$) assay. Intracellular $IP_3$ levels were measured with a $IP_3$ [$^3$H] Biotrak Assay (Amersham Biosciences, Piscataway, N.J.). Liver cells ($3.0 \times 10^6$ per well) were incubated for 0, 30, 60, 120 sec with 100 nM CSP in RPMI-1640 containing 10 mM LiCl. The plates were then placed on ice, and the reaction was stopped by aspiration of the incubation medium followed by the addition of 20% ice-cold perchloric acid. After incubation on ice for 20 min, the cells were scraped into Eppendorf tubes. The precipitated protein was removed by centrifugation at 10000 g for 15 min at 4° C. The supernatant was neutralized to pH 7.5 by titrating with ice-cold 1.5 M KOH containing 60 mM HEPES buffer. The precipitated $KClO_4$ was removed by centrifugation at 5000 g for 15 min at 4° C. Radioactivity in the supernatant was measured with a Beckman LS 6000 scintillation counter.

Chemiluminescence. The production of reactive oxygen species (ROS) by Kupffer cells was measured using luminol or lucigenin-enhanced chemiluminescence (Allen R C, Loose L D (1976) Phagocytic activation of a luminol-dependent chemiluminescence in rabbit alveolar and peritoneal macrophages. Biochem Biophys Res Commun 69: 245-252). Lucigenin reacts predominantly with superoxide, generated by the NADPH oxidase complex (Gyllenhammar, 1987), while luminol detects mainly hydrogen peroxide plus an additional spectrum of reactive oxygen species (hydrochlorous acid, nitric oxide, peroxyl radicals, and peroxynitrite anions) (Allen R C, Loose L D (1976) Phagocytic activation of a luminol-dependent chemiluminescence in rabbit alveolar and peritoneal macrophages. Biochem Biophys Res Commun 69: 245-252). Kupffer cells were cultivated in white 96-well plates (Isoplate, PerkinElmer Life and Analytical Sciences, Inc., Boston, M A) in RPMI-1640 without phenol. Before starting the experiments, the plates were washed three times with Hanks' balanced salt solution (HBSS), pH 7.4 and then incubated in HBSS containing 100 µM luminol or 50 µM lucigenin. The light emission kinetics were analyzed at 37° C. using a GENios-Plus multifunctional microplate reader (Tecan Austria GmbH, Salzburg, Austria) using the following conditions: each well was measured 60-90 times at 120 s intervals with a integration time of 1000 ms per measurement. Data were acquired with Magellan standard software and exported into XFluor4 software (Tecan). The results are expressed as relative light units (RLU) and represent the mean of four to six wells. To stimulate Kupffer cells, the cells were treated with 200 mM PMA or 0.25 mg/ml non-opsonized zymosan. Luminol and PMA were dissolved in DMSO. The final concentration of DMSO in medium did not exceed 0.1%. All other additives were dissolved in HBSS and were added as indicated in the figure legends. Zymosan A from *Saccharomyces cerevisiae* was suspended (20 mg/ml) and boiled in distilled water for 30 min followed by three washes in HBSS.

Immunolocalization of LRP-1. Frozen sections of paraformaldehyde-fixed normal rat liver were cut with a Reichert-Jung 2800 Frigocut E cryostat. Hepatocytes, Kupffer cells, and sinusoidal endothelia were purified from rat liver, cultivated overnight, and fixed with 4% paraformaldehyde in PBS. Frozen sections or fixed liver cell cultures were labeled with mAb 8B8 against the 85 kDa light chain of human LRP-1 followed by goat anti-mouse IgG conjugated to FITC (GAM-FITC) or protein A-FITC (PA-FITC) and counterstained with 0.1% Evans blue in PBS.

Microscopy and image analysis. Immunofluorescence specimens were analyzed using a Zeiss LSM 510 confocal laser scanning microscope. Digital images were processed with Adobe Photoshop (Adobe, San Jose, Calif.) and Microsoft PowerPoint software.

Statistical analysis. All experimental data were presented as the mean±STD from 4-8 wells from one of three representative experiments. Results were normalized per well or µg of cell protein. Statistical significance between groups was determined by Student's paired t-test.

Results

Figure 2A:
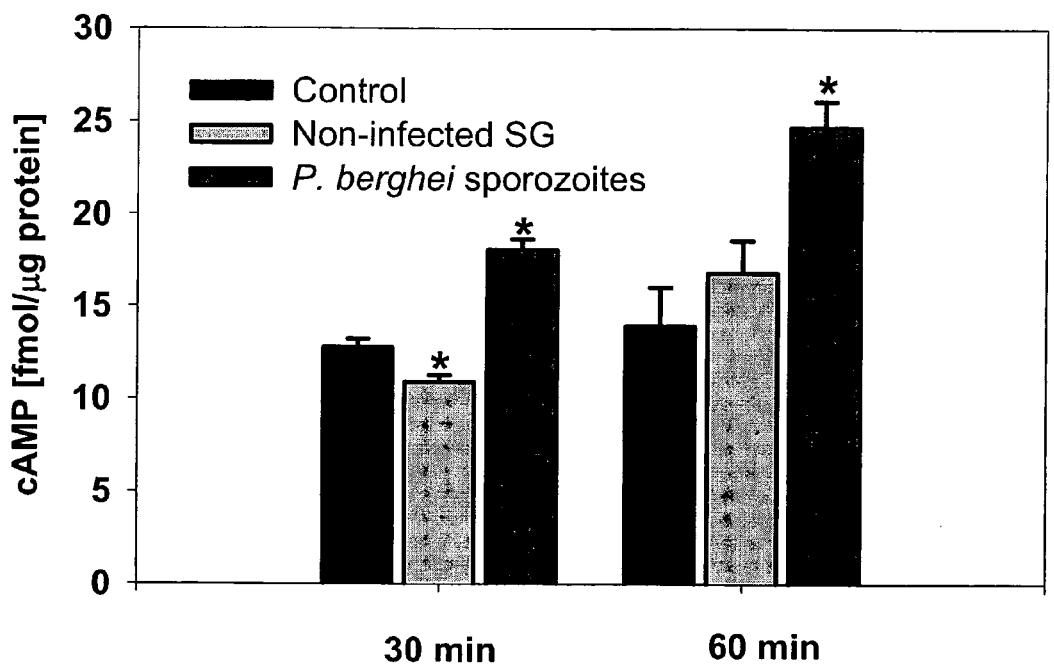
FIG. 2. Sporozoites and CSP raise the cAMP concentration in Kupffer cells. (A) *P. berghei* sporozoites raise the intracellular cAMP level. Kupffer cells ($2 \times 10^5$ per well) were cultivated for 18 h in RPMI-1640 with 10% FCS and for 6 h without FCS at 37° C. Then, the cells were exposed to *P. berghei* sporozoites ($4 \times 10^5$ per well) or equal volumes of extract from non-infected *An. stephensi* salivary glands for 30 or 60 min at 37° C. The reaction was terminated by aspirating the medium and adding 65% ice-cold ethanol. Data are represented as the mean±S.E., n=8. *Significantly different from control, $P<0.05$ by Student's t-test. (B and C) CSP increases the cAMP level in Kupffer cells in a time- and concentration-dependent fashion. Kupffer cells were cultivated as in (A) and then incubated (B) with 0.5, 5, 50, 100, or 200 nM recombinant *P. falciparum* CSP for 30 min or (C) with 50 nM CSP in RPMI-1640 at 37° C. for up to 90 min. *$P<0.05$, **$P<0.001$ compared to cells incubated without CSP. (D) Phosphodiesterase inhibition has no effect on the CSP-induced generation of cAMP. Kupffer cells were cultivated as in (A) and then treated with 50 nM CSP in RPMI-1640 without FCS for 30 min at 37° C. IBMX was added 10 min before addition of CSP. *Significantly different from control, P<0.001 by Student's t-test.

Sporozoites induce the generation of intracellular cAMP in Kupffer cells. Previous work showed that malaria sporozoites pass through Kupffer cells before invasion of hepatocytes (Pradel G, Frevert U (2001) *Plasmodium* sporozoites actively enter and pass through Kupffer cells prior to hepatocyte invasion. Hepatology 33: 1154-1165) and that CSP binds to proteoglycans and LRP-1 on the surface of mammalian cells (Shakibaei M, Frevert U (1996) Dual interaction of the malaria circumsporozoite protein with the low density lipoprotein receptor-related protein (LRP) and cell surface heparan sulfate. J Exp Med 184: 1699-1711). Since ligand binding to LRP-1 causes a cAMP increase in a variety of cells (Misra U K, Pizzo S V (2002) Regulation of cytosolic phospholipase A2 activity in macrophages stimulated with receptor-recognized forms of alpha 2-macroglobulin: role in mitogenesis and cell proliferation. J Biol Chem 277: 4069-4078; Misra U K, Gonzalez-Gronow M, Gawdi G, Pizzo S V (2005) The role of MTJ-1 in cell surface translocation of GRP78, a receptor for alpha 2-macroglobulin-dependent signaling. J Immunol 174: 2092-2097; Goretzki L, Mueller B M (1997) Receptor-mediated endocytosis of urokinase-type plasminogen activator is regulated by cAMP-dependent protein kinase. J Cell Sci 110 (Pt 12): 1395-1402; Zhu Y, Hui D Y (2003) Apolipoprotein E binding to low density lipoprotein receptor-related protein-1 inhibits cell migration via activation of cAMP-dependent protein kinase A. J Biol Chem 278: 36257-36263), and since LRP-1 is expressed on Kupffer cells (Moestrup S K, Gliemann J, Pallesen G (1992) Distribution of the $a_2$-macroglobulin receptor/low density lipoprotein receptor-related protein in human tissues. Cell Tissue Res 269: 375-382), we asked if sporozoites are able to induce intracellular signaling in these macrophages. *P. yoelii* or *P. berghei* sporozoites were isolated from the salivary glands of *An. stephensi* mosquitoes and incubated with Kupffer cells at a ratio of 2:1. The intracellular cAMP levels were analyzed after co-incubation for 30 or 60 min. Exposure to *P. berghei* (FIG. 2A) or *P. yoelii* sporozoites (not shown) increased the cAMP concentration in Kupffer cells significantly, while control extracts prepared from the same number of uninfected *An. stephensi* salivary glands had no effect. Thus, malaria sporozoites elicit the generation of cAMP in Kupffer cells.

Figure 2B:
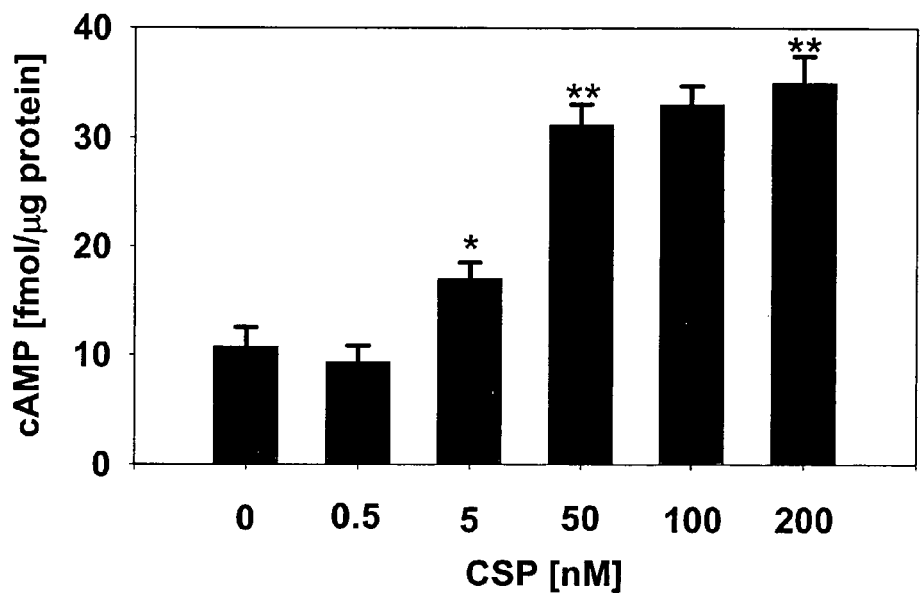
Figure 2C:
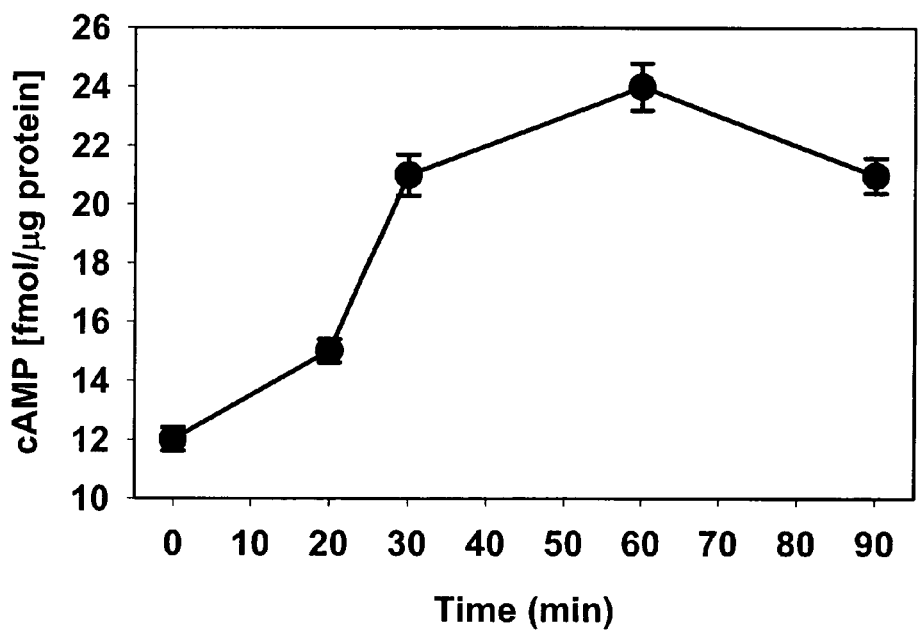
Figure 2D:
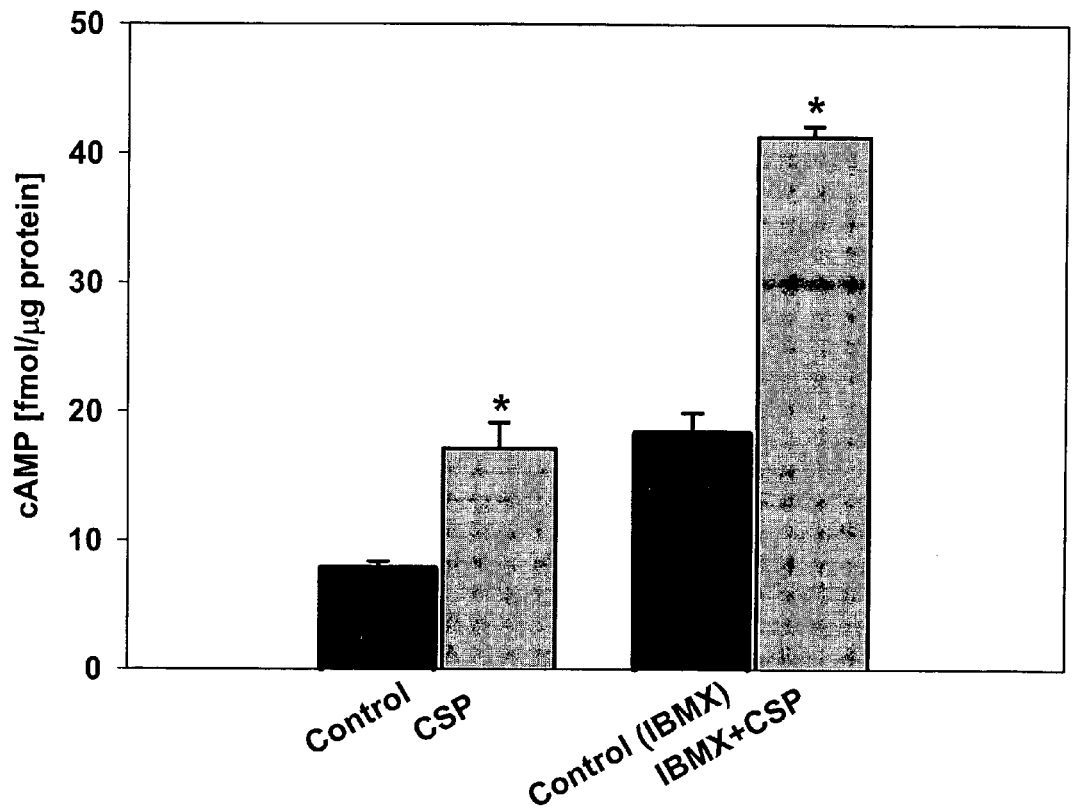

CSP raises the intracellular cAMP concentration in Kupffer cells. To elucidate the mechanism of the sporozoite-induced elevation of cAMP in Kupffer cells we performed similar experiments with CSP. Various cell types were purified from rat liver, cultivated overnight, and exposed to recombinant *P. falciparium* CSP. Incubation with CSP induced a concentration-dependent elevation of the cAMP level in Kupffer cells with maximum (3-fold) increase at 50 nM (FIG. 2B). The effect of CSP on the intracellular cAMP level in Kupffer cells was also time-dependent; immediately upon CSP binding, the cAMP concentration began to rise and reached a maximum between 30 and 60 min (FIG. 2C). The intracellular cAMP level depends on the balance between synthesis by adenylyl cyclase and degradation by phosphodiesterase. Preincubation of Kupffer cells with IBMX, a specific inhibitor of phosphodiesterase, did not reduce the CSP-induced generation of cAMP suggesting that the cAMP elevation was due to activation of adenylyl cyclase rather than inhibition of phosphodiesterase (FIG. 2D). Interestingly, CSP had no effect on the cAMP concentration in other types of liver cells (hepatocytes and endothelial cells) or in the human hepatoma cell line HepG2 (Table 1) suggesting that the CSP-induced signaling is specific for Kupffer cells.

Figure 3:
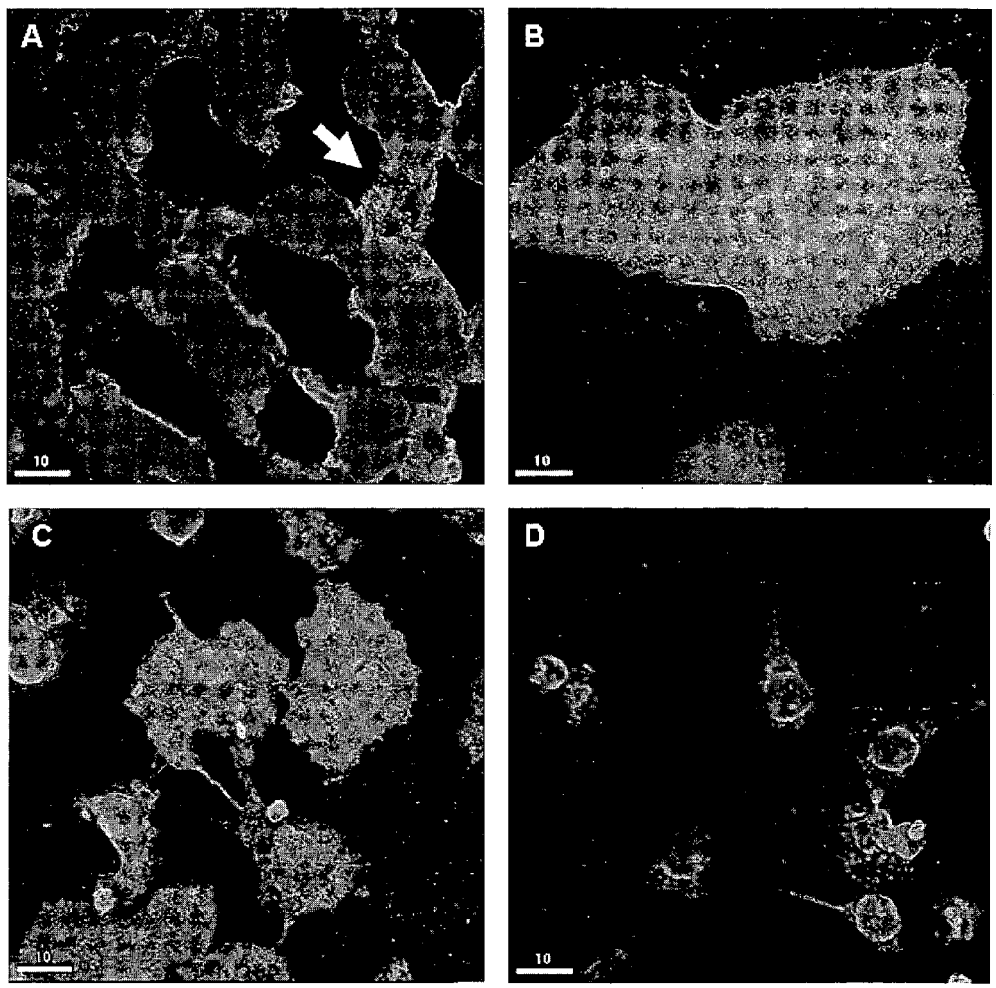
FIG. 3. LRP-1 expression is liver cell type-specific. (A) LRP-1 is associated with the sinusoids and the surface of Kupffer cells (arrow) on frozen liver sections. In cultures of purified liver cells, LRP-1 is detectable in large amounts on Kupffer cells (B) and hepatocytes (C), but not on sinusoidal endothelia (D). The cells were cultivated for 18 h and then fixed and permeabilized. LRP-1 was detected with mAb 8B8 directed against the light chain of the receptor in combination with FITC-conjugated protein A. Evans blue (shown in red) was used as a counterstain.

LRP-1 expression on the surface of liver cells. To determine whether this selective responsiveness is mirrored by a cell type-specific expression of LRP-1 in the rat liver, frozen sections were labeled with mAb 5A6/8B8, a monoclonal antibody specific for the 85 kDa light chain of LRP-1 (Strickland D K, Ashcom J D, Williams S, Burgess W H, Migliorini M, et al. (1990) Sequence identity between the a2-macroglobulin receptor and low density lipoprotein receptor-related protein suggests that this molecule is a multifunctional receptor. JBiolChem 265: 17401-17404) in combination with protein A-FITC or protein G Alexa 488. In agreement with previous work (Moestrup S K, Gliemann J, Pallesen G (1992) Distribution of the $a_2$-macroglobulin receptor/low density lipoprotein receptor-related protein in human tissues. Cell Tissue Res 269: 375-382), LRP-1 was found in high concentrations on the surface of Kupffer cells as well as lining the sinusoids (FIG. 3A). However, the close association between hepatocytes and sinusoidal endothelia along the space of Disse made it difficult to assign the LRP-1 label to one or the other cell type. We therefore determined the contribution of the various liver cell types to this sinusoidal labeling pattern using cultures of purified primary rat hepatocytes, Kupffer cells and sinusoidal endothelia. Confocal microscopy revealed high expression levels of LRP-1 on the surface of Kupffer cells (FIG. 3C) and hepatocytes (FIG. 3B), while sinusoidal endothelia were only faintly labeled (FIG. 3D). Human HepG2 hepatoma cells, which had previously been shown to support LRP-1-mediated endocytosis of CSP (Shakibaei M, Frevert U (1996) Dual interaction of the malaria circumsporozoite protein with the low density lipoprotein receptor-related protein (LRP) and cell surface heparan sulfate. J Exp Med 184: 1699-1711), expressed a high LRP-1 concentration similar to hepatocytes (data not shown). These data explain the absence of CSP-mediated signaling in sinusoidal endothelia, but not in hepatocytes suggesting that components crucial for the induction of the signaling cascade in macrophages are missing on parenchymal cells.

Figure 4A:
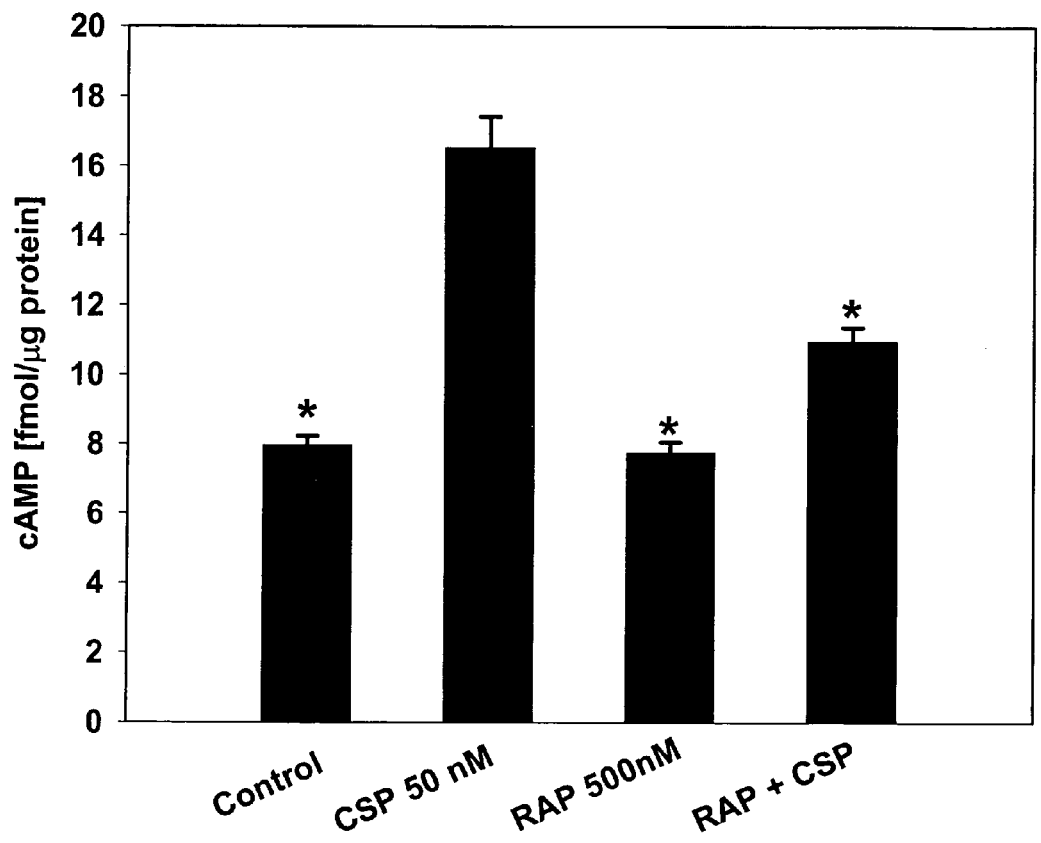
FIG. 4. Blockage of LRP-1 and syndecans inhibits the CSP-induced generation of cAMP in Kupffer cells. (A) RAP inhibits the CSP-mediated cAMP elevation. Kupffer cells were cultivated in RPMI-1640 with 10% FCS for 18 h and without FCS for 6 h at 37° C. The cells were then incubated with 50 nM CSP in RPMI-1640 without FCS for 30 min. RAP (500 nM) was added to some wells 10 min before addition of CSP. The reaction was terminated by aspirating the medium and adding 65% ice-cold ethanol. *P<0.001 compared to cells treated with CSP. (B) Combined inhibition of GAG sulfation and digestion of surface GAGs inhibits the CSP-induced generation of cAMP. Kupffer cells were incubated for 18 h at 37° C. with RPMI-1640 with 10% FCS or with a 4:1 mixture of Ham's F-12 medium and RPMI-1640 containing 20 mM sodium chlorate and 2% desalted FCS. The cells were then digested for 3 h with 20 mU/ml heparinase, 20 mU/ml heparitinase, and 500 mU/ml chondroitinase ABC in the same medium without FCS. Subsequently, 50 nM CSP was added for another 30 min. The data represent the CSP-induced cAMP elevation in percent. Results are means±S.E. of three independent experiments. *P<0.05, **P<0.001 compared with control.

Blockage of LRP-1 prevents CSP-induced signaling in Kupffer cells. To evaluate the contribution of LRP-1 to the CSP-mediated generation of cAMP, we used the universal inhibitor RAP, which blocks the binding to LRP-1 of CSP and all other ligands except α2M* (Herz J, Strickland D K (2001) LRP: a multifunctional scavenger and signaling receptor. J Clin Invest 108: 779-784; Strickland D K, Ranganathan S (2003) Diverse role of LDL receptor-related protein in the clearance of proteases and in signaling. J Thromb Haemost 1: 1663-1670). Preincubation of Kupffer cells with a 10-fold excess of RAP (500 nM) blocked the CSP-induced generation of cAMP in Kupffer cells, while 500 nM RAP alone had no effect (FIG. 4A). Lactoferrin, another LRP-1 ligand, had no significant effect on the cAMP level in any of the liver cell types studied (Table 1). These data suggest that LRP-1 is crucial for the cAMP elevation in Kupffer cells.

Figure 4B:
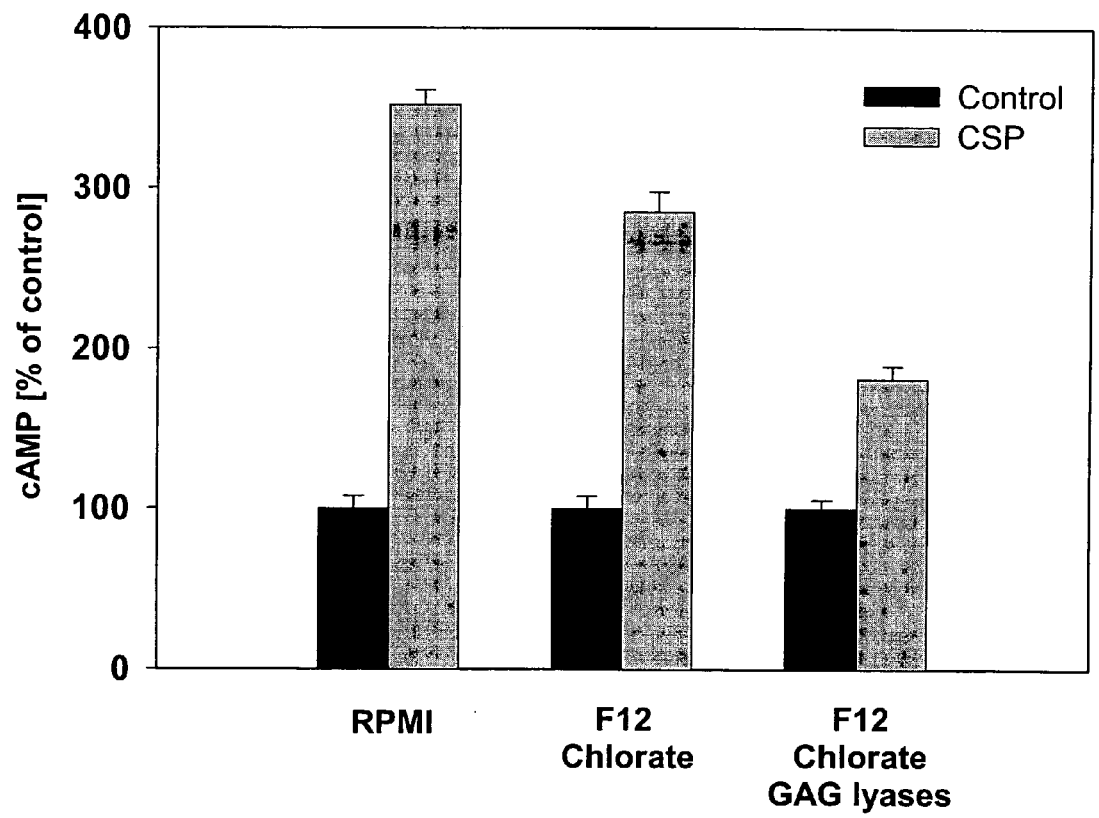

Cell surface GAGs contribute to the CSP-mediated signaling in Kupffer cells. Since both chondroitin sulfate and heparan sulfate proteoglycans are involved in the binding of CSP to Kupffer cells (Pradel G, Garapaty S, Frevert U (2002) Proteoglycans mediate malaria sporozoite targeting to the liver. Mol Microbiol 45: 637-651), we asked if signaling in Kupffer cells can be abolished by elimination of GAGs as CSP binding sites by digestion with specific GAG lyases (Frevert U, Sinnis P, Cerami C, Shreffler W, Takacs B, et al. (1993) Malaria circumsporozoite protein binds to heparan sulfate proteoglycans associated with the surface membrane of hepatocytes. J Exp Med 177: 1287-1298) in combination with sodium chlorate treatment (Pinzon-Ortiz C, Friedman J, Esko J, Sinnis P (2001) The binding of the circumsporozoite protein to cell surface heparan sulfate proteoglycans is required for *Plasmodium* sporozoite attachment to target cells. J Biol Chem 276: 26784-26791). Sodium chlorate prevents GAG sulfation by forming an abortive complex with the active sulfate donor for all known sulfation reactions (Baeuerle P A, Huttner W B (1986) Chlorate - a potent inhibitor of protein sulfation in intact cells. Biochem Biophys Res Comm 141: 870-877). Chlorate treatment alone inhibited the CSP-induced generation of cAMP in Kupffer cells by 20% (FIG. 4B). In combination with GAG lyase digestion using a cocktail of heparinase, heparitinase, and chondroitinase ABC, chlorate treatment reduced the cAMP increase by 50%, indicating that syndecans contribute to the CSP-induced cAMP production in Kupffer cells.

Figure 5:
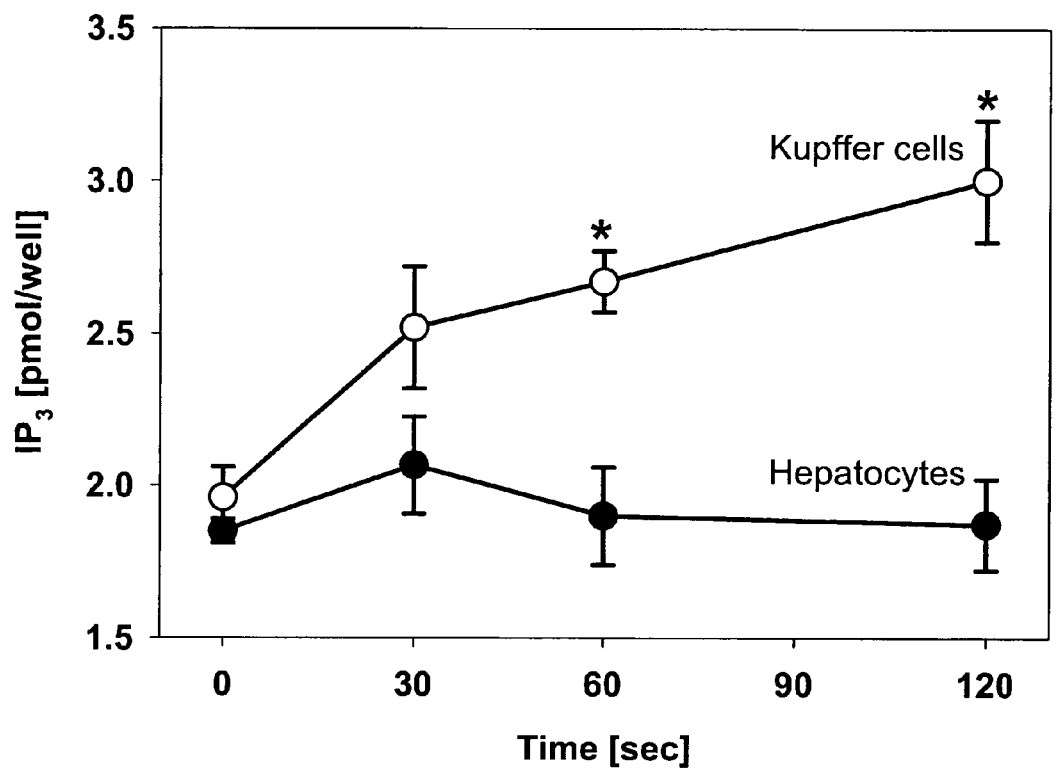
FIG. 5. CSP increases the intracellular $IP_3$ level in Kupffer cells, but not in hepatocytes. Liver cells ($3.0 \times 10^6$ per well) were cultivated for 18 h at 37° C. in RPMI-1640 with 10% FCS and for another 6 h in the same medium without FCS. The cells were then incubated with 50 nM CSP in RPMI-1640 containing 10 mM lithium chloride for the times indicated. The reactions were stopped by addition of 6.25% ice-cold perchloric acid, and $IP_3$ was extracted as described in "Experimental Procedures." *P<0.001 compared with basal level.

CSP raises the intracellular concentration of $IP_3$. We also analyzed the effect of CSP binding to Kupffer cells and hepatocytes on the generation of another second messenger, inositol-1,4,5-triphosphate ($IP_3$). Upon addition of 50 nM CSP, Kupffer cells responded with a time-dependent increase in the intracellular $IP_3$ concentration (FIG. 5), while hepatocytes showed no effect. Preincubation of Kupffer cells for 10 min with 500 nM RAP before addition of CSP prevented this increase, and RAP alone had no effect (data not shown). Taken together, these data support the concept that the CSP-induced signaling is selective for Kupffer cells and that LRP is crucially involved in these events.

Figure 6A:
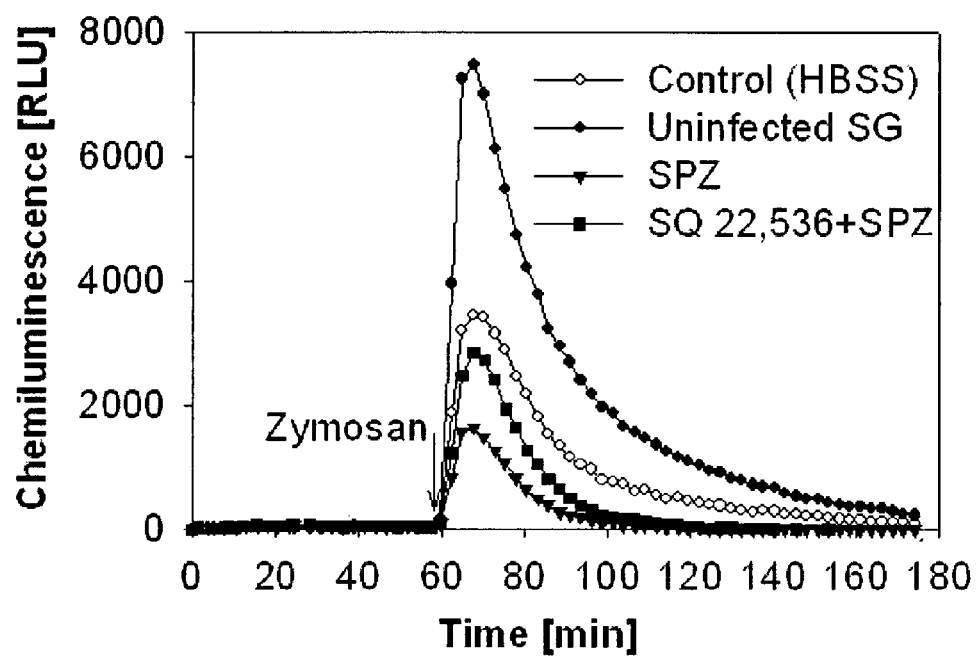
FIG. 6. Sporozoites and CSP suppress the respiratory burst in Kupffer cells. Kupffer cells ($1.5-2.5 \times 10^5$ per well) were cultivated for 18 h at 37° C. in 96-well plates in RPMI-1640 containing 10% FCS and for another 6 h in the same medium without FCS. After washing, the cells were incubated for 30-60 min with HBSS in the presence of the following additives: (A) *P. yoelii* sporozoites ($4 \times 10^5$ per well) with or without 100 µM of the adenylyl cyclase inhibitor SQ 22,536, or extract from non-infected *An. stephensi* salivary glands; or (B) 1 mM IBMX or 1 mM db-cAMP. The production of ROS was determined by luminol-enhanced chemiluminescence. The kinetics of light emission was analyzed before and after stimulation of the cells with non-opsonized zymosan. The results are expressed as relative light units (RLU) and represent the mean of four to six wells from one of three representative experiments.
Figure 6B:
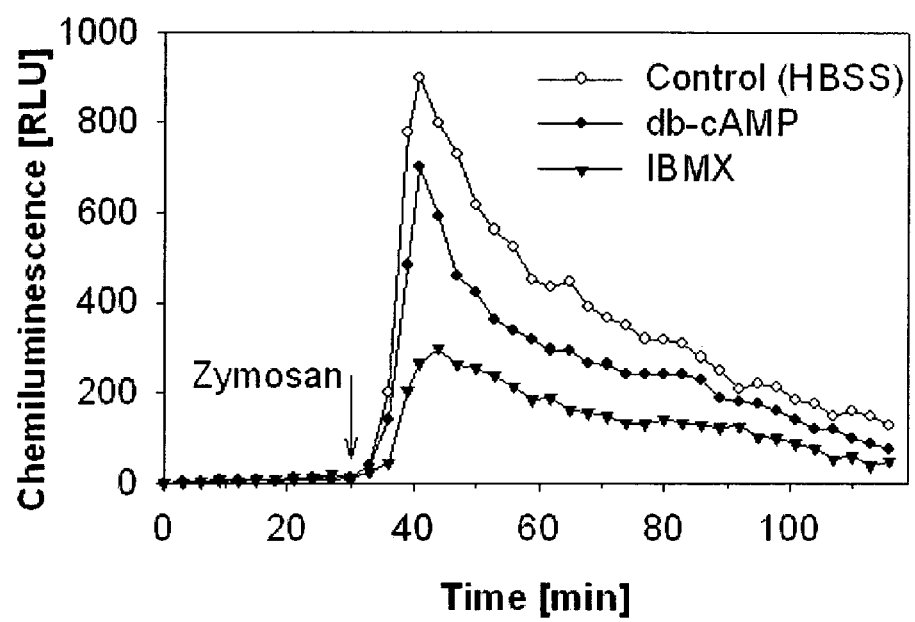

Sporozoites and CSP use a cAMP-dependent mechanism to inhibit the respiratory burst in Kupffer cells. Kupffer cells, which represent more than 80% of the total population of tissue macrophages (Kuiper J, Brouwer A, Knook D L, Berkel T J Cv (1994) Kupffer and sinusoidal endothelial cells. In: Arias I M, Boyer J L, Fausto N, Jakoby W B, Schachter D A et al., editors. The Liver: Biology and Pathobiology. 3 ed. New York: Raven Press, Ltd. pp. 791-818), play a pivotal role in the host defense against invading microorganisms. Phagocytosis of foreign microorganisms by macrophages results in activation of the NADPH oxidase (Mauël J (1996) Intracellular survival of protozoan parasites with special reference to *Leishmania* spp., *Toxoplasma gondii* and *Trypanosoma cruzi*. AdvParasitol 38: 1-51). Agents that stimulate the adenylyl cyclase inhibit the generation of ROS (Nielson C P, Bayer C, Hodson S, Hadjokas N (1992) Regulation of the respiratory burst by cyclic 3',5'-AMP, an association with inhibition of arachidonic acid release. J Immunol 149: 4036-4040). Based on the finding that sporozoites and CSP elevate the cAMP level in Kupffer cells, we hypothesized that malaria sporozoites are able to suppress the respiratory burst in these macrophages. To examine the effect of live parasites on the respiratory burst, which is normally elicited by phagocytosis of zymosan, we exposed Kupffer cells to *P. yoelii* sporozoites and measured the produced reactive oxygen intermediates by lucigenin- or luminol-enhanced chemiluminescence. Lucigenin, which detects predominantly superoxide (Gyllenhammar H (1987) Lucigenin chemiluminescence in the assessment of neutrophil superoxide production. J Immunol Methods 97: 209-213), was used to measure the reactive oxygen species originally generated by the NADPH oxidase complex. Luminol also reacts with superoxide anions, but in addition detects secondary ROS such as hydrogen peroxide, singlet molecular oxygen, and nitric oxide, was used as another luminophor (Wang J F, Komarov P, de Groot H (1993) Luminol chemiluminescence in rat macrophages and granulocytes: the role of NO, $O_2^-/H_2O_2$, and HOCl. Arch Biochem Biophys 304: 189-196). Identically prepared extracts from uninfected salivary glands were used as a control to determine the effect of mosquito tissue debris and bacteria, which contaminate routine sporozoite preparations in large quantities (Frevert, unpublished). Neither *P. yoelli* infected nor uninfected salivary gland extracts had any effect on the chemiluminescence within the 60 min incubation period (FIG. 6A) suggesting that neither sporozoites nor bacteria or salivary gland debris induce a respiratory burst in resting Kupffer cells. Subsequent exposure to zymosan, however, induced a respiratory burst in Kupffer cells with a maximum chemiluminescence response at 10 min (FIG. 6A). In relation to control cells incubated with HBSS, Kupffer cells that had been exposed to extract from uninfected control glands showed an enhanced ROS generation in response to zymosan (FIG. 6A) suggesting that the salivary gland debris and/or the bacteria had a priming effect on the Kupffer cells. This enhanced respiratory burst activity was inhibited by sporozoites by 78%. The specific adenylyl cyclase inhibitor SQ 22,536 abrogated the inhibitory effect of sporozoites on the zymosan-induced respiratory burst (FIG. 6A), suggesting that an increased cAMP concentration was responsible for the inhibition of ROS production. Indeed, the zymosan-induced respiratory burst was inhibited by 22% and 67%, respectively (FIG. 6B) when the intracellular cAMP concentration was raised by db-cAMP, a membrane-permeable cAMP analogue, or with the phosphodiesterase inhibitor IBMX (FIG. 6B). Taken together, the data indicate that the increased cAMP levels lead to a block in ROS formation.

Figure 7A:
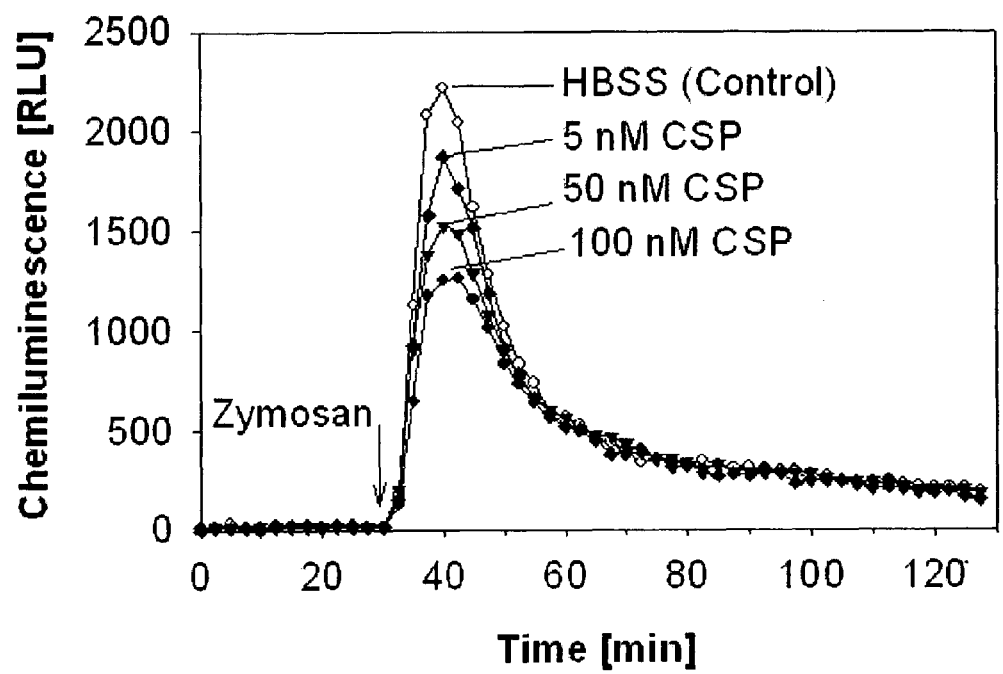
FIG. 7. CSP Blocks the Generation of ROS in Kupffer Cells Kuppfer cells ($1.5-2.5 \times 10^5$ per well) were cultivated for 48 hours at 37° C. in 96 well plates in phenol red-free RPMI-1640 containing 10% FCS and for another 6 hours in the same medium without FCS. After washing, the cells were incubated for 0-90 minutes with HBSS (A) 5, 50, or 100 nM CSP; (B) 100 nM CSP or 1 µg/ml LPS; (C) 100 mM CSP. (A, B) The kinetics of luminol-enhanced light emission was analyzed after stimulation of the cells with non-opsonized zymosan. (C) Superoxide production was monitored for 60 minutes by lucigenin-enhanced chemiluminescence after stimulation with 200 nM PMA and expressed as percent compared with the control, to which equal volumes of vehicle were added. *, P<0.05; **P<0.01 vs. control (0 min).
Figure 7B:
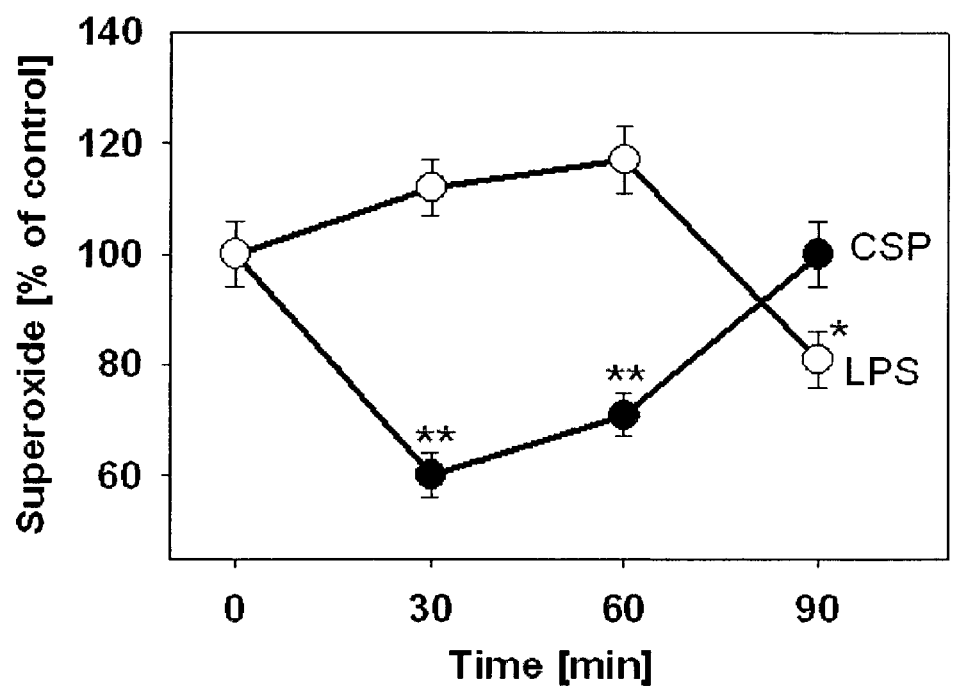

CSP is responsible for the sporozoite-mediated suppression of ROS formation. Preincubation of Kupffer cells with recombinant *P. falciparum* CSP inhibited the zymosan-induced ROS production in a dose-dependent fashion, ranging from 16% at 5 nM to 43% at 100 nM (FIG. 7A), confirming the role of CSP in the inhibition of the respiratory burst by sporozoites. To exclude that *E. coli*-derived (heat-resistant) LPS contributed to the observed effect of CSP on ROS formation, we studied the effect of heat-inactivation on the activity of our recombinant CSP preparation. Boiling for 10 min at 950 completely prevented the CSP-mediated suppression of the respiratory burst in Kupffer cells indicating that LPS was not responsible for this activity. This is supported by the finding that elimination of LPS from the incubation medium by polymyxin B did not change the effect of CSP on the respiratory burst, but completely prevented the effect of *E. coli* O55:B5 LPS (data not shown). We also compared the time-dependent effect of CSP and LPS on the production of superoxide anions and found that the suppressive effect of CSP peaked 30 min after addition of the recombinant protein and slowly decreased thereafter, while LPS began to show a small inhibitory effect only after 90 min (FIG. 7B). Because LPS can induce cyclooxygenase in Kupffer cells, thereby triggering the production of prostaglandins [Victorov A V, Hoek J B (1995) Secretion of prostaglandins elicited by lipopolysaccharide and ethanol in cultured rat Kupffer cells. Biochem Biophys Res Commun 215: 691-697], we assume that the observed delayed LPS effect is a result of a prostanoid-mediated cAMP elevation. Taken together, the data suggest that sporozoites use CSP to block the respiratory burst.

Figure 7C:
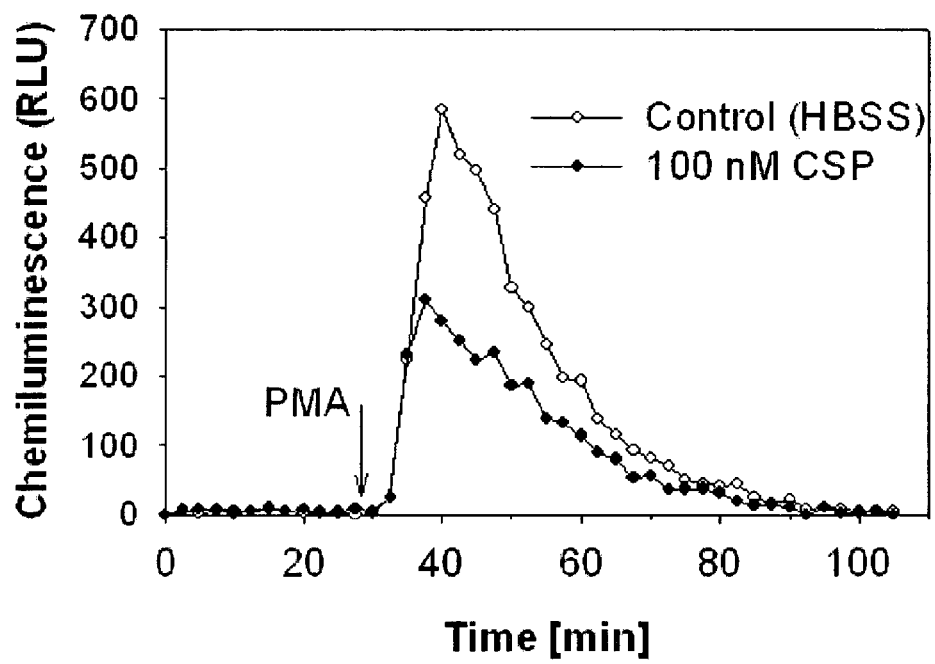
Figure 8:
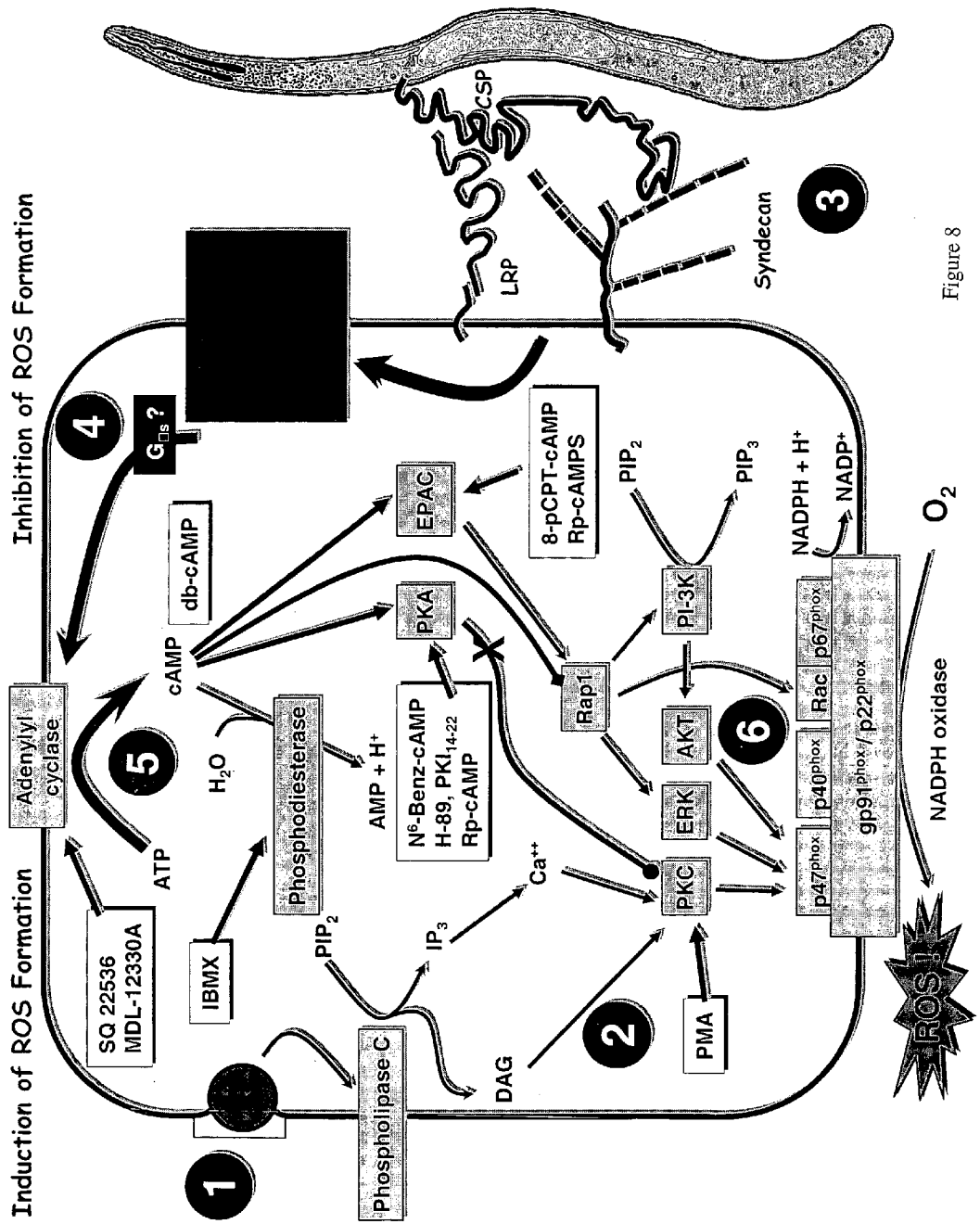
FIG. 8. Model for the CSP-mediated inhibition of the respiratory burst in Kupffer cells. (1) Phagocytosis is normally accompanied by PLC-mediated hydrolysis of $PIP_2$ and formation of DAG and $IP_3$. (2) DAG activates PKC resulting in the assembly of the NADPH oxidase and induction of a respiratory burst. $IP_3$ induces the release of $Ca^{++}$ from the endoplasmic reticulum, which also contributes to PKC activation. (3) *Plasmodium* sporozoites block these effector mechanisms. Parasite adhesion to Kupffer cells is mediated by a multivalent, high-avidity interaction between the major sporozoite surface protein CSP and the chondroitin and heparan sulfate chains from syndecans. The intimate interaction between the sporozoite and Kupffer cell surfaces facilitates engagement of some CSP molecules in a specific, high affinity interaction with LRP. (4) Sporozoite contact causes a rapid increase in the $IP_3$ level in the Kupffer cell, which leads to adenylyl cyclase activation in a calcium-dependent process, (5) causing an increase in the intracellular cAMP concentration. (6) The CSP-mediated cAMP elevation activates PKA, which blocks the assembly of the NADPH oxidase thus preventing the formation of ROS.

CSP blocks the respiratory burst downstream from PKC. NADPH oxidase assembly and induction of the respiratory burst is normally triggered by the PLC-mediated generation of DAG and $IP_3$ from $PIP_2$. $IP_3$ mediates the release of $Ca^{++}$ from intracellular stores, which, in combination with DAG, is required for PKC activation. By phosphorylating $p47^{phox}$, PKC is involved in the assembly of the NADPH oxidase and functions as an important regulator of the respiratory burst (Reeves E P, Dekker L V, Forbes L V, Wientjes F B, Grogan A, et al. (1999) Direct interaction between p47phox and protein kinase C: evidence for targeting of protein kinase C by p47phox in neutrophils. Biochem J 344 Pt 3: 859-866). To define the action of CSP on the NADPH oxidase activation cascade in relation to PKC, Kupffer cells were stimulated with phorbol-12-myristate-13-acetate (PMA), a synthetic analog of DAG and activator of PKC. PMA induced a rapid generation of ROS in Kupffer cells, which was inhibited by 47% by a 30 min preincubation of the cells with 100 nM CSP (FIG. 7C). CSP treatment alone does not induce the production of ROS in Kupffer cells (FIG. 6B, 6C, 7A). Taken together, these results suggest that elevated intracellular cAMP levels are responsible for the CSP-mediated inhibition of the respiratory burst in Kupffer cells and that the block of the NADPH oxidase activation cascade occurs downstream from PKC.

FIG. 9 illustrates the structure of the *Plasmodium* circumsporozoite proteins and the region II-plus motif present in other proteins.

Figure 10A:
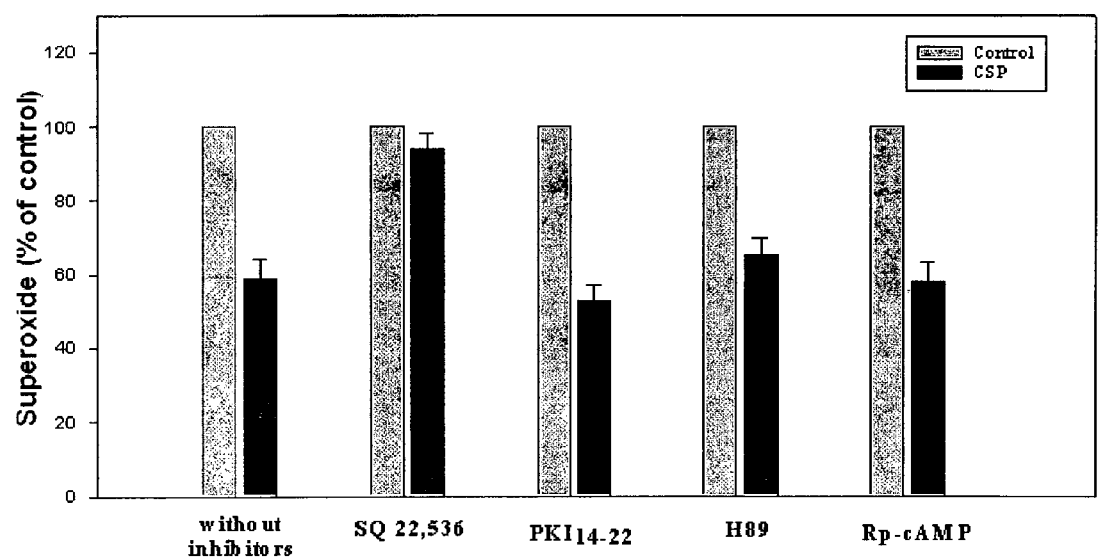
FIG. 10. Suppression of the zymosan-induced respiratory burst in Kupffer cells by CSP is cAMP-dependent, and EPAC dependent, but PKA-independent. A. Kupffer cells ($1.5-2.5 \times 10^5$ per well) were cultivated for 48 h at 37° C. in 96-well plates in phenol red-free RPMI-1640 containing 10% FCS and for another 6 h in the same medium without FCS. After washing, the cells were pretreated for 30 min with or without the adenylyl cyclase inhibitor SQ 22,536 or the protein kinase A inhibitors $PKI_{14-22}$, H-89 and Rp-cAMP) followed by incubation with 100 nM CSP for 30 min. The kinetics of light emission was analyzed after stimulation of the cells with non-opsonized zymosan. Superoxide production was monitored for 60 min by lucigenin-enhanced chemiluminescence and expressed as percent of the control, to which equal volumes of vehicle or inhibitors were added. *, P<0.001. B. Kupffer cells ($1.5-2.5 \times 10^5$ per well) were pretreated for 40 minutes with 3 mM of the EPAC activator 8-CPT-2-Me-cAMP, the PKA activator 6-MB-cAMP, or both activators. Superoxide production was monitored by luminol-enhanced chemiluminescence. The data are expressed as relative light units (RLU) and the values represent the mean of four wells from one representative of three experiments.

The inhibition of the respiratory burst is cAMP-dependent, but PKA-independent. To obtain further insight into the ROS signaling cascade in Kupffer cells, we used lucigenin-enhanced chemiluminescence to investigate the effect of adenylyl cyclase inhibitors on the CSP-induced suppression of the respiratory burst. FIG. 10A demonstrates that the adenylyl cyclase inhibitor SQ 22,536 reversed the suppressive effect of CSP on superoxide generation, suggesting that adenylyl cyclase activation led to the inhibition of the NADPH oxidase. Because PKA activation has been reported to interfere with the assembly of the NADPH oxidase in human neutrophils by preventing the PKC-mediated phosphorylation of $p47^{phox}$ [Bengis-Garber C, Gruener N (1996) Protein kinase A downregulates the phosphorylation of p47 phox in human neutrophils: a possible pathway for inhibition of the respiratory burst. Cell Signal 8: 291-296], we also tested the effect of PKA inhibitors. Preincubation of Kupffer cells with the specific PKA inhibitors H-89, $PKI_{14-22}$, and Rp-cAMP [Gjertsen B T, Mellgren G, Otten A, Maronde E, Genieser H G, et al. (1995) Novel (Rp)-cAMPS analogs as tools for inhibition of cAMP-kinase in cell culture. Basal cAMP-kinase activity modulates interleukin-1 beta action. J Biol Chem 270: 20599-20607] failed to prevent the CSP-mediated inhibition of the respiratory burst (FIG. 10A). These data indicate that the intracellular cAMP increase is responsible for the CSP-mediated inhibition of the respiratory burst, but that an alternative, PKA-independent pathway prevents the assembly of the NADPH oxidase in Kupffer cells.

Figure 10B:
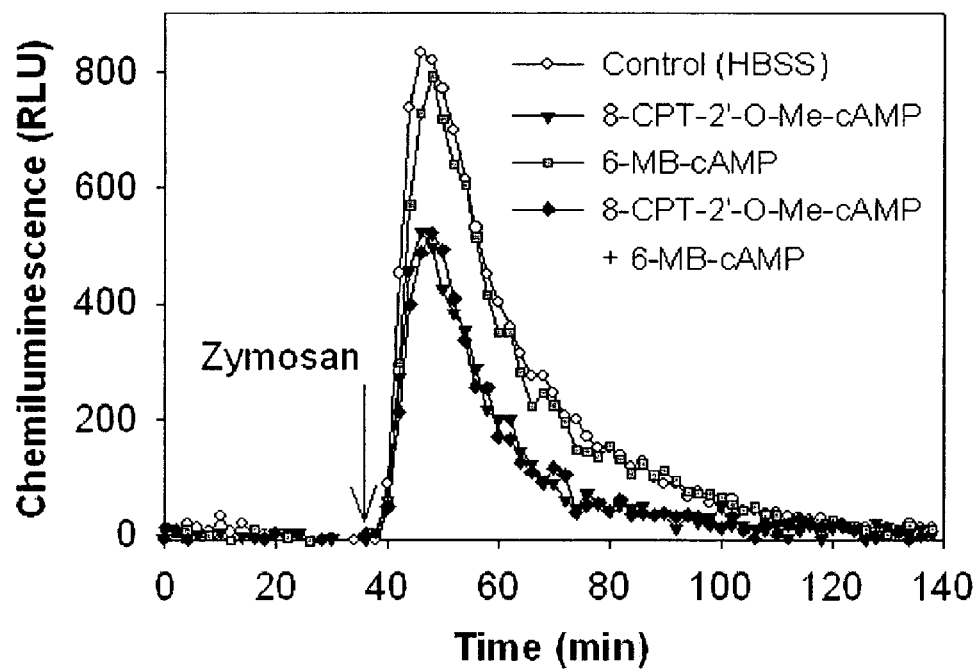

ROS formation in Kupffer cells is regulated by EPAC. Because activation of the "Exchange Protein Directly Activated by cAMP" (EPAC) suppresses ROS formation in human alveolar macrophages [Aronoff D M, Canetti C, Serezani C H, Luo M, Peters-Golden M (2005) Cutting edge: macrophage inhibition by cyclic AMP (cAMP): differential roles of protein kinase A and exchange protein directly activated by cAMP-1. J Immunol 174: 595-599], we considered the possibility that the exchange protein directly activated by cAMP (EPAC) regulates the assembly of the NADPH oxidase also in Kupffer cells. Specific EPAC inhibitors are not available to date, so that the involvement of EPAC in the CSP-mediated inhibition of ROS formation could not be tested directly. To obtain insight into the general contribution of PKA and EPAC to the regulation of the respiratory burst, we incubated Kupffer cells with selective PKA and EPAC activators [Rehmann H, Schwede F, Doskeland S O, Wittinghofer A, Bos J L (2003) Ligand-mediated activation of the cAMP-responsive guanine nucleotide exchange factor Epac. J Biol Chem 278: 38548-38556; Seino S, Shibasaki T (2005) PKA-dependent and PKA-independent pathways for cAMP-regulated exocytosis. Physiol Rev 85: 1303-1342]. FIG. 10B shows that when incubated with 3 mM concentrations, the selective EPAC activator 8-CPT-2-Me-cAMP inhibited the zymosan-induced ROS formation by Kupffer cells, while the PKA activator 6-MB-cAMP had no effect. Simultaneous incubation with both 8-CPT-2-Me-cAMP and 6-MB-cAMP did not exceed the effect of the EPAC activator alone. Thus, EPAC activation can inhibit ROS production by rat Kupffer cells.

TABLE 1

Effect of CSP and lactoferrin on intracellular level of cAMP in liver cell types

| Cell culture | cAMP, fmol/μg protein | | |
|---|---|---|---|
| | Control | CSP | Lactoferrin |
| Kupffer cells | 10.85 ± 1.73 | 31.22 ± 1.84* | 14.10 ± 2.10 |
| Liver endothelial cells | 6.41 ± 0.23 | 6.35 ± 0.26 | 5.58 ± 0.30 |
| Hepatocytes | 2.03 ± 0.25 | 2.40 ± 0.24 | 2.61 ± 0.09 |
| HepG2 cells | 6.22 ± 0.56 | 6.37 ± 0.30 | 6.50 ± 0.07 |

Table 1. Effect of CSP and lactoferrin on the intracellular cAMP level in liver cells. The cells ($2 \times 10^5$ per well) were incubated for 30 min at 37° C. with serum-free RPMI-1640 containing 50 nM CSP or 100 nM lactoferrin. After washing with PBS on ice, the reactions were stopped by addition of 65% ice-cold ethanol. The data represent the mean±S.E. of three independent experiments. n=6-10. *Significantly different from control, p<0.01 by Student's t-test.

TABLE 2

SEQUENCE IDENTIFIERS FOR THE PLASMODIUM CIRCUMSPOROZOITE PROTEINS

| | PubMed Accession No. | Nucleic Acid | Protein |
|---|---|---|---|
| P. falciparum | AY878621 | 1 | 2 |
| P. vivax | S73385 | 3 | 4 |
| P. simium | L05068 | 5 | 6 |
| P. knowlesi | AY327572 | 7 | 8 |
| P. cynomolgi | M15102 | 9 | 10 |
| P. brasilianum | J03203 | 11 | 12 |
| P. malariae | S69014 | 13 | 14 |
| P. berghei | X17606 | 15 | 16 |
| P. yoelii | DQ012939 | 17 | 18 |
| P. gallinaceum | U65959 | 19 | 20 |

Discussion

Malaria sporozoites must pass through Kupffer cells to reach hepatocytes, their initial site of multiplication in the mammalian host (Frevert U, Engelmann S, ZougbédéS, Stange J, Ng B, et al. (2005) Intravital observation of *Plasmodium berghei* sporozoite infection of the liver. PLoS Biol 3: e192; Baer K, Roosevelt M, Van Rooijen N, Clarkson Jr. A B, Frevert U (2006) Kupffer cells are obligatory for *Plasmodium* sporozoite infection of the liver. Cell Microbiol in press; Frevert, U. et al, (2006), Nomadic or sessile: can Kupffer cells function as portals for malaria sporozoites to the liver? Cell Microbiol., In press; Frevert, U. et al. (2006), Penetrating Biological Barriers. Liver: *Plasmodium* sporozoite passage across the sinusoidal cell layer. In: Soldati, D., Burleigh, B A, editors, Molecular Mechanisms of Parasite Invasion: Landes, In press). Here we show that sporozoite contact not only fails to induce a respiratory burst in Kupffer cells, but also suppresses the induction of ROS formation in response to secondary stimuli. By using the high-affinity interaction between CSP and the scavenger receptor LRP-1 (Shakibaei M, Frevert U (1996) Dual interaction of the malaria circumsporozoite protein with the low density lipoprotein receptor-related protein (LRP) and cell surface heparan sulfate. J Exp Med 184: 1699-1711), sporozoites raise the intracellular cAMP concentration in Kupffer cells, thus preventing the fatal consequences of the assembly of the NADPH oxidase. Syndecans contribute to the induction of the signaling cascade by providing a large number of multivalent CSP-binding glycosaminoglycan chains (Pradel G, Garapaty S, Frevert U (2002) Proteoglycans mediate malaria sporozoite targeting to the liver. Mol Microbiol 45: 637-651), thereby facilitating the binding of CSP to LRP-1. These findings explain why malaria sporozoites survive the Kupffer cell passage unharmed and why *Plasmodium* liver stages can develop inside hepatocytes in the vicinity of traversed Kupffer cells. Thus, *Plasmodium* sporozoites exploit the overall macrophage deactivating and anti-inflammatory properties of cAMP to suppress ROS production in Kupffer cells, thus facilitating the establishment of a malaria infection.

The archetypal second messenger cAMP, which is responsible for the conversion of many intercellular signals to intracellular events, has been implicated in the modulation of numerous immunologic reactions. In macrophages including Kupffer cells, increased cAMP levels inhibit phagocytosis, phagolysosomal fusion, the LPS-mediated induction of macrophage activation, and killing of carcinoma cells (Aronoff D M, Canetti C, Serezani C H, Luo M, Peters-Golden M (2005) Cutting edge: macrophage inhibition by cyclic AMP (cAMP): differential roles of protein kinase A and exchange protein directly activated by cAMP-1. J Immunol 174: 595-

599; Sionov R V, Gallily R (1990) Engulfment and intracellular killing of F9 teratocarcinoma cells by non-activated murine macrophages. Int Immunol 2: 291-301; Rossi A G, McCutcheon J C, Roy N, Chilvers E R, Haslett C, et al. (1998) Regulation of macrophage phagocytosis of apoptotic cells by cAMP. J Immunol 160: 3562-3568; Kambayashi T, Wallin R P, Ljunggren H G (2001) cAMP-elevating agents suppress dendritic cell function. J Leukoc Biol 70: 903-910; Nogueira-Machado J A, Lima e Silva F C, Medina L O, Costa D C, Chaves M M (2003) Modulation of the reactive oxygen species (ROS) generation mediated by cyclic AMP-elevating agents or Interleukin 10 in granulocytes from type 2 diabetic patients (NIDDM): a PKA-independent phenomenon. Diabetes Metab 29: 533-537; Chini E N, Chini C C, Bolliger C, Jougasaki M, Grande J P, et al. (1997) Cytoprotective effects of adrenomedullin in glomerular cell injury: central role of cAMP signaling pathway. Kidney Int 52: 917-925; Lowrie D B, Aber V R, Jackett P S (1979) Phagosome-lysosome fusion and cyclic adenosine 3':5'-monophosphate in macrophages infected with *Mycobacterium microti, Mycobacterium bovis* BCG or *Mycobacterium lepraemurium*. J Gen Microbiol 110: 431-441; Metzger Z, Hoffeld J T, Oppenheim J J (1981) Regulation by PGE2 of the production of oxygen intermediates by LPS-activated macrophages. J Immunol 127: 1109-1113; Ichinose M, Sawada M, Maeno T (1994) Inhibitory effect of vasoactive intestinal peptide (VIP) on phagocytosis in mouse peritoneal macrophages. Regul Pept 54: 457-466; Hahn P Y, Yoo P, Ba Z F, Chaudry I H, Wang P (1998) Upregulation of Kupffer cell beta-adrenoceptors and cAMP levels during the late stage of sepsis. Biochim Biophys Acta 1404: 377-384; Newman S L, Mikus L K, Tucci M A (1991) Differential requirements for cellular cytoskeleton in human macrophage complement receptor- and Fc receptor-mediated phagocytosis. J Immunol 146: 967-974; Chaves M M, Silvestrini A A, Silva-Teixeira D N, Nogueira-Machado J A (1996) Effect in vitro of gamma interferon and interleukin-10 on generation of oxidizing species by human granulocytes. Inflamm Res 45: 313-315; Nogueira-Machado J A, Lima E S F C, Lima E S R, Medina L O, Costa D C, et al. (2002) Effect in vitro of cyclic nucleotides-elevating agents on nitric oxide production by human granulocytes from type 2-diabetic patients. Diabetes Metab 28: 45-50]. There is also solid evidence that cAMP elevating agents suppress the respiratory burst in various types of phagocytic cells in a dose-dependent fashion (Nogueira-Machado J A, Lima e Silva F C, Medina L O, Costa D C, Chaves M M (2003) Modulation of the reactive oxygen species (ROS) generation mediated by cyclic AMP-elevating agents or Interleukin 10 in granulocytes from type 2 diabetic patients (NIDDM): a PKA-independent phenomenon. Diabetes Metab 29: 533-537; O'Dowd Y M, El-Benna J, Perianin A, Newsholme P (2004) Inhibition of formyl-methionyl-leucyl-phenylalanine-stimulated respiratory burst in human neutrophils by adrenaline: inhibition of Phospholipase A2 activity but not p47phox phosphorylation and translocation. Biochem Pharmacol 67: 183-190; Mitsuyama T, Takeshige K, Minakami S (1993) Cyclic AMP inhibits the respiratory burst of electropermeabilized human neutrophils at a downstream site of protein kinase C. Biochim Biophys Acta 1177: 167-173; Wang J P, Raung S L, Huang L J, Kuo S C (1998) Involvement of cyclic AMP generation in the inhibition of respiratory burst by 2-phenyl-4-quinolone (YT-1) in rat neutrophils. Biochem Pharmacol 56: 1505-1514; Martins Chaves M, Prates Rodrigues A L, Pereira dos Reis A, Gerzstein N C, Nogueira-Machado J A (2002) Correlation between NADPH oxidase and protein kinase C in the ROS production by human granulocytes related to age. Gerontology 48: 354-359; Hoffman M, Feldman S R, Pizzo S V (1983) Alpha 2-macroglobulin 'fast' forms inhibit superoxide production by activated macrophages. Biochim Biophys Acta 760: 421-423). However, information on the exact time sequence by which the various subunits assemble to form the functional NADPH oxidase and the molecular events that control the onset of the assembly cascade is scarce, and data on the NADPH oxidase from Kupffer cells are lacking. In human neutrophils, elevation of cAMP by prostaglandins, histamine, adenosine, and β-adrenergic agonists inhibit superoxide generation in response to stimulation with the chemotactic peptide fMLP (Sedgwick J B, Berube M L, Zurier R B (1985) Stimulus-dependent inhibition of superoxide generation by prostaglandins. Clin Immunol Immunopathol 34: 205-215; Cronstein B N, Rosenstein E D, Kramer S B, Weissmann G, Hirschhorn R (1985) Adenosine; a physiologic modulator of superoxide anion generation by human neutrophils. Adenosine acts via an A2 receptor on human neutrophils. J Immunol 135: 1366-1371; Nielson C P (1987) Beta-adrenergic modulation of the polymorphonuclear leukocyte respiratory burst is dependent upon the mechanism of cell activation. J Immunol 139: 2392-2397). The mechanism of suppression has been suggested to involve inhibition of phospholipase D (Tyagi S R, Olson S C, Burnham D N, Lambeth J D (1991) Cyclic AMP-elevating agents block chemoattractant activation of diradylglycerol generation by inhibiting phospholipase D activation. J Biol Chem 266: 3498-3504) and phospholipase $A_2$ signaling pathways (Nielson C P, Bayer C, Hodson S, Hadjokas N (1992) Regulation of the respiratory burst by cyclic 3',5'-AMP, an association with inhibition of arachidonic acid release. J Immunol 149: 4036-4040), resequestration of cytosolic calcium by up-regulation of the endomembrane calcium-ATPase (Anderson R, Goolam Mahomed A, Theron A J, Ramafi G, Feldman C (1998) Effect of rolipram and dibutyryl cyclic AMP on resequestration of cytosolic calcium in FMLP-activated human neutrophils. Br J Pharmacol 124: 547-555), and PKA-dependent down-regulation of $p47^{phox}$ phosphorylation (Bengis-Garber C, Gruener N (1996) Protein kinase A downregulates the phosphorylation of p47 phox in human neutrophils: a possible pathway for inhibition of the respiratory burst. Cell Signal 8: 291-296). CSP inhibited the respiratory burst in Kupffer cells both after exposure to zymosan and after direct stimulation of PKC with PMA suggesting that the cAMP-mediated block of ROS formation occurred at or downstream from PKC. However, unlike human neutrophils, in which PKA down-regulates the phosphorylation of $p47^{phox}$ and specific PKA inhibitors consequently restore the cAMP-mediated inhibition of the respiratory burst (Bengis-Garber C, Gruener N (1996) Protein kinase A downregulates the phosphorylation of p47 phox in human neutrophils: a possible pathway for inhibition of the respiratory burst. Cell Signal 8: 291-296; Mitsuyama T, Takeshige K, Minakami S (1993) Cyclic AMP inhibits the respiratory burst of electropermeabilized human neutrophils at a downstream site of protein kinase C. Biochim Biophys Acta 1177: 167-173; Mitsuyama T, Takeshige K, Furuno T, Tanaka T, Hidaka K, et al. (1995) An inhibitor of cyclic AMP-dependent protein kinase enhances the superoxide production of human neutrophils stimulated by N-formyl-methionyl-leucyl-phenylalanine. Mol Cell Biochem 145: 19-24), PKA does not appear to play a role in the CSP-mediated suppression of the respiratory burst in Kupffer cells. An alternative way of linking the cAMP increase to the block in ROS formation is via a family of cAMP binding proteins termed Epac (exchange protein directly activated by cAMP) (de Rooij J, Zwartkruis F J, Verheijen M H, Cool R H, Nijman S M, et al. (1998) Epac is a Rap1 guanine-nucleotide-exchange factor directly activated by cyclic AMP. Nature 396: 474-477; Kawasaki H, Springett G M, Mochizuki N, Toki S, Nakaya M, et al. (1998) A family of cAMP-binding proteins that directly activate Rap1. Science 282: 2275-2279). Specific EPAC inhibitors are unavailable to date, but others have demonstrated that stimulation of both PKA and EPAC-1 inhibits $H_2O_2$ production in alveolar macrophages in a dose-dependent fashion (Bengis-Garber C, Gruener N (1996) Protein kinase A downregulates the phosphorylation of p47 phox in human neutrophils: a possible pathway for inhibition of the respiratory burst. Cell Signal 8: 291-296; Aronoff D M, Canetti C, Serezani C H, Luo M, Peters-Golden M (2005) Cutting edge: macrophage inhibition by cyclic AMP (cAMP): differential roles of protein kinase A and exchange protein directly activated by cAMP-1. J Immunol 174: 595-599]. We used the selective EPAC and PKA activators 8-CPT-2-Me-cAMP and 6-MB-cAMP (Rehmann H, Schwede F, Doskeland S O, Wittinghofer A, Bos J L (2003) Ligand-mediated activation of the cAMP-responsive guanine nucleotide exchange factor Epac. J Biol Chem 278: 38548-38556; Seino S, Shibasaki T (2005) PKA-dependent and PKA-independent pathways for cAMP-regulated exocytosis. Physiol Rev 85: 1303-1342; Gjertsen B T, Mellgren G, Otten A, Maronde E, Genieser H G, et al. (1995) Novel (Rp)-cAMPS analogs as tools for inhibition of cAMP-kinase in cell culture. Basal cAMP-kinase activity modulates interleukin-1 beta action. J Biol Chem 270: 20599-20607; Aronoff D M, Canetti C, Serezani C H, Luo M, Peters-Golden M (2005) Cutting edge: macrophage inhibition by cyclic AMP (cAMP): differential roles of protein kinase A and exchange protein directly activated by cAMP-1. J Immunol 174: 595-599), to show that EPAC, but not PKA activation causes inhibition of ROS formation in Kupffer cells. Together with the finding that the specific PKA inhibitors H-89, $PKI_{14-22}$, and Rp-cAMP had no effect on the CSP-mediated inhibition of ROS formation and because there is no evidence that cAMP blocks ROS formation in macrophages via Rac (Diebold B A, Bokoch G M (2005) Rho GTPases and the control of the oxidative burst in polymorphonuclear leukocytes. Curr Top Microbiol Immunol 291: 91-111; Hordijk P L (2006) Regulation of NADPH oxidases: the role of Rac proteins. Circ Res 98: 453-462; Bokoch G M, Diebold B A (2002) Current molecular models for NADPH oxidase regulation by Rac GTPase. Blood 100: 2692-2696), we conclude that *Plasmodium* CSP activates a cAMP/EPAC-independent pathway in Kupffer cells that interferes with the complex assembly cascade of the NADPH oxidase.

Signaling through syndecans is not associated with an increase in the intracellular cAMP level (Carey D J (1997) Syndecans: multifunctional cell-surface co-receptors. Biochem J 327: 1-16; Rapraeger A C (2000) Syndecan-regulated receptor signaling. J Cell Biol 149: 995-997; Rapraeger A C (2001) Molecular interactions of syndecans during development. Sem Cell Dev Biol 12: 107-116; Rapraeger A C, Ott V L (1998) Molecular interactions of the syndecan core proteins. Curr Op Cell Biol 10: 620-628; Woods A, Couchman J R (1998) Syndecans: synergistic activators of cell adhesion. Trends Cell Biol 8: 189-193; Woods A, Oh E-S, Couchman J R (1998) Syndecan proteoglycans and cell adhesion. Matrix Biology 17: 477-483; Zimmermann P, David G (1999) The syndecans, tuners of transmembrane signaling. FASEB J 13 (Suppl.): S91-S100). We assume, therefore, that the contribution of syndecans to the observed signaling is to provide a multivalent, high-avidity platform on the macrophage surface that facilitates the transfer of CSP to LRP-1. On the other hand, LRP-1 has been reported to stimulate adenylyl cyclase directly by interacting with a G$\alpha$s protein (Goretzki L, Mueller B M (1998) Low-density-lipoprotein-receptor-related protein (LRP) interacts with a GTP-binding protein. Biochem J 336 (Pt 2): 381-386). Despite its nature as a universal scavenger receptor and its fairly wide tissue distribution (Moestrup S K, Gliemann J, Pallesen G (1992) Distribution of the $\alpha_2$-macroglobulin receptor/low density lipoprotein receptor-related protein in human tissues. Cell Tissue Res 269: 375-382), LRP can induce selective, cell type-specific signaling cascades by cooperating with a variety of signaling receptors. For example, identification of the urokinase-type plasminogen activator receptor (uPAR), the N-methyl-D-aspartate receptor (NMDAR), and the platelet-derived growth factor receptor (PDGFR) as LRP co-receptors (Herz J, Strickland D K (2001) LRP: a multifunctional scavenger and signaling receptor. J Clin Invest 108: 779-784; Loukinova E, Ranganathan S, Kuznetsov S, Gorlatova N, Migliorini M M, et al. (2002) Platelet-derived growth factor (PDGF)-induced tyrosine phosphorylation of the low density lipoprotein receptor-related protein (LRP). Evidence for integrated co-receptor function betwenn LRP and the PDGF. J Biol Chem 277: 15499-15506; Ma Z, Thomas K S, Webb D J, Moravec R, Salicioni A M, et al. (2002) Regulation of Rac1 activation by the low density lipoprotein receptor-related protein. J Cell Biol 159: 1061-1070; Orr A W, Pedraza C E, Pallero M A, Elzie C A, Goicoechea S, et al. (2003) Low density lipoprotein receptor-related protein is a calreticulin coreceptor that signals focal adhesion disassembly. J Cell Biol 161: 1179-1189; Herz J (2003) LRP: a bright beacon at the blood-brain barrier. J Clin Invest 112: 1483-1485) has greatly advanced our understanding of the signal transduction cascades and biological consequences elicited by the individual LRP ligands (Boucher P, Liu P, Gotthardt M, Hiesberger T, Anderson R G, et al. (2002) Platelet-derived growth factor mediates tyrosine phosphorylation of the cytoplasmic domain of the low density lipoprotein receptor-related protein in caveolae. J Biol Chem 277: 15507-15513; Loukinova E, Ranganathan S, Kuznetsov S, Gorlatova N, Migliorini M M, et al. (2002) Platelet-derived growth factor (PDGF)-induced tyrosine phosphorylation of the low density lipoprotein receptor-related protein (LRP). Evidence for integrated co-receptor function betwenn LRP and the PDGF. J Biol Chem 277: 15499-15506; Boucher P, Gotthardt M, Li W P, Anderson R G, Herz J (2003) LRP: role in vascular wall integrity and protection from atherosclerosis. Science 300: 329-332; Boucher P, Gotthardt M (2004) LRP and PDGF signaling: a pathway to atherosclerosis. Trends Cardiovasc Med 14: 55-60; Sitrin R G, Pan P M, Harper H A, Blackwood R A, Todd R F, 3rd (1999) Urokinase receptor (CD87) aggregation triggers phosphoinositide hydrolysis and intracellular calcium mobilization in mononuclear phagocytes. J Immunol 163: 6193-6200; Sitrin R G, Pan P M, Harper H A, Todd R F, 3rd, Harsh D M, et al. (2000) Clustering of urokinase receptors (uPAR; CD87) induces proinflammatory signaling in human polymorphonuclear neutrophils. J Immunol 165: 3341-3349; Nguyen D H, Webb D J, Catling A D, Song Q, Dhakephalkar A, et al. (2000) Urokinase-type plasminogen activator stimulates the Ras/Extracellular signal-regulated kinase (ERK) signaling pathway and MCF-7 cell migration by a mechanism that requires focal adhesion kinase, Src, and Shc. Rapid dissociation of GRB2/Sps-Shc complex is associated with the transient phosphorylation of ERK in urokinase-treated cells. J Biol Chem 275: 19382-19388). In neurons, apoE binding to the dual receptor system LRP/NMDAR raises the intracellular calcium concentration, which in turn elevates the cAMP level through a calcium/calmodulin-dependent mechanism (Bacskai B J, Xia M Q, Strickland D K, Rebeck G W, Hyman B T (2000) The endocytic receptor protein LRP also mediates neuronal calcium signaling via N-methyl-$_D$-aspartate receptors. Proc Natl Acad Sci USA 97: 11551-11556; Herz J, Strickland D K (2001) LRP: a multifunctional scavenger and signaling receptor. J Clin Invest 108: 779-784; Smit M J, Iyengar R (1998) Mammalian adenylyl cyclases. Adv Second Messenger Phosphoprotein Res 32:1-21; Beisiegel U, Weber W, Ihrke G, Herz J, Stanley K K (1989) The LDL-receptor-related protein, LRP, is an apolipoprotein E-binding protein. Nature 341: 162-164; Qiu Z, Crutcher K A, Hyman B T, Rebeck G W (2003) ApoE isoforms affect neuronal N-methyl-D-aspartate calcium responses and toxicity via receptor-mediated processes. Neuroscience 122: 291-303). NMDAR is also expressed on various macrophages (Dickman K G, Youssef J G, Mathew S M, Said S I (2004) Ionotropic glutamate receptors in lungs and airways: molecular basis for glutamate toxicity. Am J Respir Cell Mol Biol 30: 139-144; Mentaverri R, Kamel S, Wattel A, Prouillet C, Sevenet N, et al. (2003) Regulation of bone resorption and osteoclast survival by nitric oxide: possible involvement of NMDA-receptor. J Cell Biochem 88: 1145-1156; Merle B, Itzstein C, Delmas P D, Chenu C (2003) NMDA glutamate receptors are expressed by osteoclast precursors and involved in the regulation of osteoclastogenesis. J Cell Biochem 90: 424-436), however elimination of calcium from the medium or addition of the NMDAR inhibitor MK-801 had no effect on the CSP-mediated suppression of the respiratory burst (data not shown), rendering the possibility unlikely that CSP raises the cAMP concentration in Kupffer cells via an NMDAR-gated calcium influx. Initial experiments with the intracellular calcium chelator BAPTA (data not shown) support an alternative sequence of events, namely that the observed rapid increase in the intracellular IP$_3$ concentration in response to CSP binding mobilized calcium from intracellular stores, thus leading to early, transient adenylyl cyclase activation. A similar scenario has been described for the anti-inflammatory cytokine IL-13, which inhibits the respiratory burst in phagocytic cells by elevating IP$_3$ and calcium within 30-60 seconds, immediately followed by an initial small cAMP increase prior to the onset of a larger, more sustained cAMP elevation (Sozzani P, Cambon C, Vita N, Seguelas M H, Caput D, et al. (1995) Interleukin-13 inhibits protein kinase C-triggered respiratory burst in human monocytes. Role of calcium and cyclic AMP. J Biol Chem 270: 5084-5088). Taken together, the data support a model in which LRP-1 ligation leads to Gas-mediated adenylyl cyclase stimulation as well as to PLC activation; the resulting IP3 triggers the release of calcium from intracellular stores, which in turn further stimulates cAMP formation. We observed by intravital microscopy that after adhering to the surface of a Kupffer cell, sporozoites pause for a few minutes before starting the entry process [Frevert U, Engelmann S, Zougbédé S, Stange J, Ng B, et al. (2005) Intravital observation of Plasmodium berghei sporozoite infection of the liver. PLoS Biol 3: e192]. This time may be required to accumulate sufficient cAMP to ensure protection against the fatal consequences of the respiratory burst.

Mosquito salivary gland extract had a priming effect on Kupffer cells as shown by the considerably enhanced respiratory burst activity upon subsequent exposure to zymosan. We interpret this phenomenon as a response of the phagocytes to the bacteria and/or mosquito tissue debris, both of which contaminate routine sporozoite preparations in large amounts (Frevert, unpublished data). Importantly, sporozoites suppressed this enhanced burst activity by 78% suggesting that in addition to the CSP-mediated block of ROS formation, the parasites are also able to prevent macrophage priming. Other phagocytes such as neutrophil granulocytes respond to LPS and injurious substances including cytokines such as TNF-α with phagocytosis, secretion of stored enzymes and proteins, and production of oxygen intermediates [Condliffe A M, Kitchen E, Chilvers E R (1998) Neutrophil priming: pathophysiological consequences and underlying mechanisms. Clin Sci (Lond) 94: 461-471; Binder R, Kress A, Kan G, Herrmann K, Kirschfink M (1999) Neutrophil priming by cytokines and vitamin D binding protein (Gc-globulin): impact on C5a-mediated chemotaxis, degranulation and respiratory burst. Mol Immunol 36: 885-892; Dewas C, Dang P M, Gougerot-Pocidalo M A, El-Benna J (2003) TNF-alpha induces phosphorylation of p47(phox) in human neutrophils: partial phosphorylation of p47phox is a common event of priming of human neutrophils by TNF-alpha and granulocyte-macrophage colony-stimulating factor. J Immunol 171: 4392-4398]. Neutrophil priming can occur within seconds to minutes thus explaining the rapid reaction of the Kupffer cells to salivary gland extract. While Kupffer cells are not exposed to mosquito contaminants under natural transmission conditions, sporozoites cause substantial damage to hepatocytes while migrating to their final destination in the liver (Frevert U, Engelmann S, Zougbédé S, Stange J, Ng B, et al. (2005) Intravital observation of Plasmodium berghei sporozoite infection of the liver. PLoS Biol 3: e192; Mota M M, Pradel G, Vanderberg J P, Hafalla J C R, Frevert U, et al. (2001) Migration of Plasmodium sporozoites through cells before infection. Science 291: 141-144), and this may be one reason why Plasmodium has acquired a mechanism to avoid macrophage priming in response to tissue injury. Another important consideration in this context is that many in vivo studies involving Plasmodium infection of the liver are performed by intravenous injection of isolated sporozoites. Because the majority of the contaminants contained in such sporozoite preparations must be expected to be removed from the blood by Kupffer cells, suppressive or otherwise modulating effects on Plasmodium liver stage development due to priming of the entire Kupffer cell population cannot be excluded. Sporozoite purification by affinity chromatography (Kappe S H I, Gardner M J, Brown S M, Ross J, Matuschewski K, et al. (2001) Exploring the transcriptome of the malaria sporozoite stage. Proc Natl Acad Sci USA 98: 9895-9900; Mack S R, Vanderberg J P, Nawrot R (1978) Column separation of Plasmodium berghei sporozoites. J Parasitol 64: 166-168) should help minimize such unpredictable effects.

Like CSP, several other LRP-1 ligands also elevate the intracellular cAMP concentration. For instance, α2M* binding to the dual receptor system LRP-1/α2MSR raises the cAMP level via a pertussis-insensitive trimeric G protein in peritoneal macrophages, resulting in cell proliferation (Misra U K, Akabani G, Pizzo S V (2002) The role of cAMP-dependent signaling in receptor-recognized forms of alpha 2-macroglobulin-induced cellular proliferation. J Biol Chem 277: 36509-36520; Misra U K, Gonzalez-Gronow M, Gawdi G, Hart J P, Johnson C E, et al. (2002) The role of Grp 78 in alpha 2-macroglobulin-induced signal transduction. Evidence from RNA interference that the low density lipoprotein receptor-related protein is associated with, but not necessary for, GRP 78-mediated signal transduction. J Biol Chem 277: 42082-42087; Misra U K, Pizzo S V (2002) Regulation of cytosolic phospholipase A2 activity in macrophages stimulated with receptor-recognized forms of alpha 2-macroglobulin: role in mitogenesis and cell proliferation. J Biol Chem 277: 4069-4078; Misra U K, Gawdi G, Pizzo S V (1996) Binding of rat α1-inhibitor-3-methylamine to the α2-macroglobulin signaling receptor induces second messengers. J Cell Biochem 61: 61-71; Misra U K, Adlakha C L, Gawdi G, McMillian M K, Pizzo S V, et al. (2001) Apolipoprotein E and mimetic peptide initiate a calcium-dependent signaling response in macrophages. J Leukoc Biol 70: 677-683; Misra U K, Pizzo S V (1996) Ligation of the alpha 2-macroglobulin signaling receptor on macrophages induces synthesis of platelet activating factor. J Cell Biochem 61: 39-47). The cAMP increase is insensitive to RAP, but nevertheless requires the presence of LRP-1 on the cell surface (Bacskai B J, Xia M Q, Strickland D K, Rebeck G W, Hyman B T (2000) The endocytic receptor protein LRP also mediates neuronal calcium signaling via N-methyl-$_D$-aspartate receptors. Proc Natl Acad Sci USA 97: 11551-11556). In contrast, the cAMP elevation induced in peritoneal macrophages by the LRP-1 ligands lactoferrin and apoE triggers a PLC signaling cascade that causes PKA activation by a pertussis toxin-sensitive Gas protein and this cAMP increase, in agreement with our data, can be blocked by RAP [Misra U K, Chu CT-C, Gawdi G, Pizzo S V (1994) The relationship between low density lipoprotein-related/α2-macroglobulin (α2M) receptors and the newly described α2M signaling receptor. J Biol Chem 269: 18303-18306; Misra U K, Chu C T-C, Gawdi G, Pizzo S V (1994) Evidence for second α2-macroglobulin receptor. J Biol Chem 269: 12541-12547; Goretzki L, Mueller B M (1997) Receptor-mediated endocytosis of urokinase-type plasminogen activator is regulated by cAMP-dependent protein kinase. J Cell Sci 110 (Pt 12): 1395-1402; Goretzki L, Mueller B M (1998) Low-density-lipoprotein-receptor-related protein (LRP) interacts with a GTP-binding protein. Biochem J 336 (Pt 2): 381-386]. Thus, the mechanism CSP uses for adenylyl cyclase activation resembles that of lactoferrin and apoE rather than that of α2M*. Earlier studies showed that simultaneous elimination of both cell surface GAGs and LRP-1 markedly reduces $P.$ $berghei$ sporozoite invasion in vitro (Shakibaei M, Frevert U (1996) Dual interaction of the malaria circumsporozoite protein with the low density lipoprotein receptor-related protein (LRP) and cell surface heparan sulfate. J Exp Med 184: 1699-1711), while elimination of LRP-1 alone had only a minor effect (Shakibaei M, Frevert U (1996) Dual interaction of the malaria circumsporozoite protein with the low density lipoprotein receptor-related protein (LRP) and cell surface heparan sulfate. J Exp Med 184: 1699-1711; Marshall P, Rohlmann A, Nussenzweig V, Herz J, Sinnis P (2000) $Plasmodium$ sporozoites invade cells with targeted deletions in the LDL receptor related protein. Mol Biochem Parasitol 106: 293-298). To define the role of LRP-1 in sporozoite infection of the liver, transgenic LRP-1$^{flox/flox}$ Cre$^+$ mice with a functional defect of LRP-1 in hepatocytes were generated by conditional gene targeting (Rohlmann A, Gotthardt M, Hammer R E, Herz J (1998) Inducible inactivation of hepatic LRP gene by cre-mediated recombination confirms role of LRP in clearance of chylomicron remnants. J Clin Invest 101: 689-695; Rohlmann A, Gotthardt M, Willnow T E, Hammer R E, Herz J (1996) Sustained somatic gene inactivation by viral transfer of Cre recombinase. Nat Biotechnol 14: 1562-1565). The unexpected finding that infection of these LRP-1-deficient animals with $P.$ $yoelii$ sporozoites was not diminished (Marshall P, Rohlmann A, Nussenzweig V, Herz J, Sinnis P (2000) $Plasmodium$ sporozoites invade cells with targeted deletions in the LDL receptor related protein. Mol Biochem Parasitol 106: 293-298) may be explained as follows. First, the mutant LDLR$^{-/-}$;LRP-1$^{flox/flox}$ mice expressed normal levels of cell surface and, in particular, extracellular matrix GAGs in their livers and this obviously allowed normal sporozoite arrest and sinusoidal gliding to Kupffer cells (Frevert U, Engelmann S, Zougbédé S, Stange J, Ng B, et al. (2005) Intravital observation of $Plasmodium$ $berghei$ sporozoite infection of the liver. PLoS Biol 3: e192). Second, Cre adenovirus injection into LRP-1$^{flox/flox}$ and double mutant LDLR$^{-/-}$; LRP-1$^{flox/flox}$ mice resulted in LRP-1 gene inactivation in 100% of the hepatocytes [Rohlmann A, Gotthardt M, Willnow T E, Hammer R E, Herz J (1996) Sustained somatic gene inactivation by viral transfer of Cre recombinase. Nat Biotechnol 14: 1562-1565], but the livers of the LDLR$^{-/-}$;LRP-1$^{flox/flox}$ mice and, in particular the LRP-1$^{flox/flox}$ mice, still contained low levels of LRP-1 (Rohlmann A, Gotthardt M, Hammer R E, Herz J (1998) Inducible inactivation of hepatic LRP gene by cre-mediated recombination confirms role of LRP in clearance of chylomicron remnants. J Clin Invest 101: 689-695; Rohlmann A, Gotthardt M, Willnow T E, Hammer R E, Herz J (1996) Sustained somatic gene inactivation by viral transfer of Cre recombinase. Nat Biotechnol 14: 1562-1565). Since Ad5 viruses infect predominantly hepatocytes and to a minor degree also sinusoidal endothelia (Herz J, Gerard R D (1993) Adenovirus-mediated transfer of low density lipoprotein receptor gene acutely accelerates cholesterol clearance in normal mice. Proc Natl Acad Sci U S A 90: 2812-2816), but not Kupffer cells (Shayakhmetov D M, Li Z Y, Ni S, Lieber A (2004) Analysis of adenovirus sequestration in the liver, transduction of hepatic cells, and innate toxicity after injection of fiber-modified vectors. J Virol 78: 5368-5381), the residual LRP-1 in the Cre adenovirus injected LRP-1 mutant mice may have derived from these phagocytes. Thus, LRP-1-mediated signal transduction was likely unaffected in the Kupffer cells of the LRP-1$^{flox/flox}$ Cre$^+$ mice, explaining the unaltered rate of $P.$ $yoelii$ sporozoite entry into the liver. The host's adenylyl cyclase/phosphodiesterase system represents a key target for many microorganisms to sabotage macrophage function. For example, pathogenic bacteria such as $Bordetella$ $pertussis$, $Bacillus$ $anthracis$, $Pseudomonas$ $aeruginosa$, and $Yersinia$ $pestis$ secrete adenylate cyclase toxins that become activated by eukaryotic cofactors and either modulate or completely shut down the normal cell function (Ahuja N, Kumar P, Bhatnagar R (2004) The adenylate cyclase toxins. Crit Rev Microbiol 30: 187-196). By raising the cAMP concentration in neutrophils, for example, the $Bacillus$ $anthracis$ edema toxin blocks phagocytosis and inhibits both particulate and PMA-induced superoxide production. In lymphocytes, this bacterial enzyme alters the expression of immuno-regulatory genes and inhibits proliferation. Parasites such as $Toxoplasma$ $gondii$, $Giardia$ $lamblia$, $Entamoeba$ $histolytica$, $Schistosoma$ $mansoni$, and $Trypanosoma$ $cruzi$ manipulate the cAMP level in various cells of the host to down-modulate NO production, inhibit ROS formation, induce IL-6 synthesis, and inhibit contractility and locomotion (Rozenfeld C, Martinez R, Figueiredo R T, Bozza M T, Lima F R, et al. (2003) Soluble factors released by $Toxoplasma$ $gondii$-infected astrocytes down-modulate nitric oxide production by gamma interferon-activated microglia and prevent neuronal degeneration. Infect Immun 71: 2047-2057; Shant J, Ghosh S, Bhattacharyya S, Ganguly N K, Majumdar S (2004) The alteration in signal transduction parameters induced by the excretory-secretory product from $Giardia$ $lamblia$. Parasitology 129: 421-430; Rawal S, Majumdar S, Dhawan V, Vohra H (2004) $Entamoeba$ $histolytica$ Gal/GalNAc lectin depletes antioxidant defences of target epithelial cells. Parasitology 128: 617-624; Angeli V, Faveeuw C, Delerive P, Fontaine J, Barriera Y, et al. (2001) Schistosoma mansoni induces the synthesis of IL-6 in pulmonary microvascular endothelial cells: role of IL-6 in the control of lung eosinophilia during infection. Eur J Immunol 31: 2751-2761; Joensen L, Borda E, Kohout T, Perry S, Garcia G, et al. (2003) $Trypanosoma$ $cruzi$ antigen that interacts with the betal-adrenergic receptor and modifies myocardial contractile activity. Mol Biochem Parasitol 127: 169-177; Rodriguez A, Martinez I, Chung A, Berlot C H, Andrew N W (1999) cAMP Regulates Ca$^{2+}$-dependent Exocytosis of Lysosomes and Lysosome-mediated cell Invasion by *Trypanosomes*. J Biol Chem 274: 16754-16759; Rico G, Diaz-Guerra O, Kretschmer R R (1995) Cyclic nucleotide changes induced in human leukocytes by a product of axenically grown *Entamoeba histolytica* that inhibits human monocyte locomotion. Parasitol Res 81: 158-162). Primary targets are immune effector cells, whose deactivation naturally facilitates survival of the microorganisms in the host. In addition to suppressing ROS formation in vitro, *Plasmodium* sporozoites are also able to disrupt the normal Kupffer cell function in vivo: consistent with induction of a cAMP increase (Feng W G, Wang Y B, Zhang J S, Wang X Y, Li C L, et al. (2002) cAMP elevators inhibit LPS-induced IL-12 p40 expression by interfering with phosphorylation of p38 MAPK in murine peritoneal macrophages. Cell Res 12: 331-337), infectious *P. berghei* sporozoites inhibit the expression of MHC class I molecules and the production of IL-12p40 (Steers N, Schwenk R, Bacon D J, Berenzon D, Williams J, et al. (2005) The immune status of Kupffer cells profoundly influences their responsiveness to infectious *Plasmodium berghei* sporozoites. Eur J Immunol 35: 2335-46). Since any alteration in the concentration of the ubiquitous second messenger cAMP has a profound effect on many cellular processes, it must be expected that *Plasmodium* sporozoites are able to manipulate other macrophage functions as well.

Example 2

In vivo Assessment of CSP or a Biologically Active Fragment in Inflammatory Bowel Disease Materials and Methods
Ulcerative Colitis Model Ulcerative colitis is induced in Sprague Dawley rats (7-8 weeks old) by the administration of a solution in which 90 mg of trinitrobenzenesulfonic acid (TNB) is dissolved in 1.5 ml. of 20% ethanol. Certain groups of rats are treated with various doses of the CSP or active fragment and other groups are treated with a vehicle control. In these studies, the preferred route of administration of the CSP or active fragment is by catheter to deliver the compound directly to the colon. Most preferably, a rubber catheter such as a Nelaton catheter No. 8 is used (Rush Company, West Germany). The compound is preferably introduced about 6 cm from the rectum in the rat. One of skill in the art will be familiar with the use of such catheters to deliver compounds to the desired site in rats of varying ages and weights and in other experimental animals. During the experiments rats are clinically evaluated daily, and presence or absence of diarrhea is monitored.

At one to two weeks after induction of colitis, the rats are sacrificed by decapitation and evaluated for severity of colonic lesions and general colonic pathology to evaluate the development of ulcerative colitis. The colon is rapidly removed, opened, rinsed in saline, blotted gently, weighed and fixed in 10% formalin. Standardized sections of ileum, jejunum, duodenum, stomach, liver, pancreas, kidneys and lungs are also fixed, and processed for histologic examination. Additional sections from grossly involved and uninvolved areas of colon, ileum and jejunum are frozen and subsequently homogenized for the determination of colonic myeloperoxidase activity by the method of Bradley et al. (Bradley, P. P., et al., J. Invest. Dermatol. 78:206-209 (1982)) using 0.0005% hydrogen peroxide as a substrate. This enzyme, located mainly in the azurophilic granules of polymorphonuclear leukocytes is used as a quantitative index of inflammation (Morris, G. P., et al., Gastroenterology 96:795-803 (1989); Bradley, P. P., et al., J. Invest. Dermatol. 78:206-209 (1982); Krawisz, J. E., et al., Gastroenterology 47:1344-1350 (1985)).

For morphologic studies at the light microscopy level 2-4 mm long tissue sections of tissue are fixed in 10% buffered (pH7) formalin, dehydrated and embedded in paraffin or in the J8-4 plastic embedding medium. Sections (1-5 um) from all organs are stained with hematoxylin and eosin (H&E) and, in addition, sections from stomach and duodenum are also stained with the periodic acid-Schiff (PAS) technique.

Morphometric analysis of colonic lesions is performed by stereomicroscopic planimetry (Szabo, S., et al., J. Pharm. Methods 13:59-66 (1985); Szabo, S., et al., Gastroenterology 88:228-236 (1985); Szabo, S., et al., Scand. J. Gastroenterol. 21 Suppl.:92-96 (1986)). In addition, "damage scores" 0-5 are calculated using a combination of gross and histologic assessment of the extent of TNB-induced colonic lesions (Morris, G. P., et al., Gastroenterology 96:795-803 (1989)). Thus, there are four quantitative endpoints in evaluating the experimental colonic lesions: planimetry ($mm^2$) of involved colon, damaged score (grades 0-5) derived from gross and histologic evaluation, colon weight (Calkins, B. M., et al., Epidemiol. Rev. 8:60-85 (1986)) indicating edema, inflammatory infiltrate and tissue proliferation, as well as myeloperoxidase activity quantitatively reflecting the intensity of inflammation.

All the four endpoints have been reported to be sensitive and quantitive indicators of the severity and extent of induced experimental gastric and colonic lesions (Szabo, S., et al., Gastroenterology 86:1271 (1984); Szabo, S., et al., Dig. Dis. Sci. 34:1323 (1989); Szabo, S., et al., J. Pharm. Methods 13:59-66 (1985); Morrison, B. C., et al., eds., Gastrointestinal Pathology, 2d ed., London (1979); Szabo, S., et al., Scand. J. Gastroenterol. 21 Suppl.:92-96 (1986)).

For further characterization of chronic inflammation, standard immunoperoxidase and cytochemical methods are used to selectively obtain and count subpopulations of B and T-lymphocytes in the inflamed colon. The colons of rats which receive the vascular tracer monastral blue for the detection of early vascular injury, which is well established in the pathogenesis of chemically induced gastric lesions (Szabo, S., et al., Gastroenterology 88:228-236 (1985); Szabo, S., et al., Scand. J. Gastroenterol. 21 Suppl.:92-96 (1986)), are cleared in glycerol for 24 hr after planimetric assessment of mucosal ulcers. The area of blood vessels labeled with deposition of monastral blue between the damaged endothelium and vascular basement membrane, are measured by stereomicroscopic planimetry (Szabo, S., et al., Gastroenterology 88:228-236 (1985); Szabo, S., et al., Scand. J. Gastroenterol. 21 Suppl.:92-96 (1986)).

Tissue samples from colon and ileum from rats killed up to 2 days after IA or NEM are fixed in Karnovsky's fixative for electron microscopy, dehydrated in graded ethanol, embedded, cut and stained for examination by transmission electron microscopy as described (Trier, J. S., et al., Gastroenterology 92:13-22 (1987)).

In pharmacologic experiments, detailed dose- and time-response studies are performed with the CSP or active fragments, which will also be administered by various routes (e.g., i.c., per-os (p.o.)). The colonic lesions are quantitated by computerized planimetry coupled with stereomicroscopy (Szabo, S., et al., J. Pharm. Methods 13:59-66 (1985)), and by a combination of damage score derived from gross and histologic examination of intestines, colonic weight and myeloperoxidase activity, as described by Morris et al. with the TNB model of IBD (Morris, G. P., et al., Gastroenterology 96:795-803 (1989)).

For biochemical studies, the tissue (total thickness, mucosa and muscle separated in certain experiments) is either homogenized with a Tekmar homogenizer, or kept frozen for up to two weeks.

For statistical evaluation, the results are stored and analyzed by computer. The statistical significance of differences of the group values are calculated (for parametric data) by two-tailed Student's t-test or (with parametric statistics) by the Mann-Whitney test or the Fisher-Yates Exact Probability Test.

Example 3

In vivo Assessment of CSP or an Active Fragment of CSP in a Multiple Sclerosis Model Lysolecithin Induced Demyelination For these experiments, 12 week old SJL/J mice are anesthetized with sodium pentobarbitol and a dorsal laminectomy is performed in the upper thoracic region of the spinal cord. A 34 guage needle attached to a Hamilton syringe is used to inject 1 µl of a 1% solution of lysolecithin directly into the dorsolateral aspect of the cord. Animals are killed on day 21 post injection and the injected region of the spinal cord is removed and processed for morphological evaluation.

As a second model of demyelination, intraspinal injection of lysolecithin is used. Twelve-week-old SJL/J mice are anesthetized by intraperitoneal injection of sodium pentobarbitol (0.08 mg/g). Dorsal laminectomies are performed on the upper thoracic region of the spinal cord and lysolecithin (L-lysophosphatidylcholine) (Sigma, St. Louis, Mo.) is injected as described (Pavelko, K. D., van Engelen, B. G. & Rodriguez, M. (1998) J. Neurosci. 18, 2498_2505). Briefly, a 34 gauge needle attached to a Hamilton syringe mounted on a stereotactic micromanipulator is used to inject 1% solution of lysolecithin in sterile PBS (pH 7.4) with Evan's blue added as a marker. The needle is inserted into the dorsolateral part of the spinal cord, 1 µl of lysolecithin solution is injected, and then the needle is slowly withdrawn. The wound is sutured in two layers, and mice are allowed to recover. The day of lysolecithin injection is designated day 0.

Seven days after lysolecithin injection, mice are treated with the CSP or active fragment thereof as a bolus intraperitoneal injection or intravenously. Initially a dose response study will be done to establish the most effective dose for use in this animal model. Control mice are treated with bolus intraperitoneal or intravenous injection of vehicle control. Three weeks and five weeks after the lysolecithin injection, mice are sacrificed and one mm thick sections are prepared. The araldite block showing the largest lysolecithin induced demyelination lesion is used for quantitative analysis. The total area of the lesion is quantitated using a Zeiss interactive digital analysis system. The total number of remyelinated fibers are quantitated using a Nikon microscope/computer analysis system. The data is expressed as the number of remyelinated axons/mm$^2$ of lesion.

Lysolecithin treated mice are given various doses of the CSP or active fragment thereof on days 0, 3, 7, 10, 14, and 17 after lysolecithin injection. Animals are killed on day 21 after lysolecithin injection. PBS or vehicle controls serve as negative controls.

EAE Model

Experimental allergic encephalomyelitis (EAE) is a T cell mediated autoimmune disease of the central nervous system (CNS). Disease can be induced in susceptible strains of mice by immunization with CNS myelin antigens or alternatively, disease can be passively transferred to susceptible mice using antigen stimulated CD4+ T cells [Pettinelli, J. Immunol. 127, 1981, p. 1420]. EAE is widely recognized as an acceptable animal model for multiple sclerosis in primates [Alvord et al. (eds.) 1984. Experimental allergic encephalomyelitis—A useful model for multiple sclerosis. Alan R. Liss, New York]. The effects of administration of a CSP or active fragment thereof on induction of EAE following the adoptive transfer of lymphocytes from immunized mice restimulated in vitro with a synthetic peptide of myelin proteolipid protein (PLP) is studied.

Adoptive Transfer of PLP Sensitized LNC

Female SJL/J mice (7-10 wks) are purchased from The Jackson Laboratory, and are housed 5 to a cage and are fed standard rodent chow diet with water ad libitum. Mice are divided into groups and certain groups are treated with vehicle control (PBS), other groups are treated with various doses of the CSP or active fragments. Mice are then immunized in two sites on the flank with 150 µg of mouse PLP peptide comprising residues 139-151. PLP was administered in 200 µl of Complete Freunds adjuvant containing 2 mg/ml Mycobacteria Tuberculosis H37RA (Difco). On the day of immunization mice are injected intravenously with $0.75 \times 10^{10}$ Bordatella pertussis bacilli (Massachusetts Public Health Laboratories, Boston, Mass.). Ten days after immunization, spleens and lymph nodes (popliteal, axillary and brachial) are harvested and the cells are resuspended in RPMI-1640 containing 10% FBS (Hyclone), $5 \times 10^{-5}$ M 2-Mercaptoethanol, 100 µg/ml streptomycin and 100 U/ml penicillin. PLP is added to the cultures at 2 µg/ml. After 96 hours, the cells are harvested, washed twice and are injected i.p. into naive SJL/J mice.

Clinical Evaluation of Disease

Mice are observed for clinical signs of EAE and are scored on a scale of 0 to 3 as follows:
0.5—Distal limp tail
1.0—Complete limp tail
1.5—Limp tail and hind limb weakness (unsteady gait)
2.0—Partial hind limb paralysis
3.0—Complete bilateral hind limb paralysis Example 4

In vivo Assessment of CSP or Active Fragments Thereof in a Model of Arthritis

Arthritis

Inhibitory Effect of a CSP or Active Fragment on Edema of Arthritis

In order to observe the inhibitory effect on edema of a pharmaceutical composition of the present invention, preferably one comprising a CSP or active fragment thereof, 6 albino rats weighing 200 gm are used per test group and edema is induced by injecting a mixture of 0.5 ml of Zymosan-A (20 mg/ml/kg) and 0.5 ml of Freund's adjuvant into the left paw of the animals and the animals are observed for the progress of edema for 70 days by taking a photograph before and after induction of edema and by measuring the paw size with a caliper. Certain groups will be given various doses of the CSP, or an active fragment of a CSP before or after injection of the Zymosan-A and Freund's adjuvant. Administration may be via the intravenous route, the oral route, the intraperitoneal route or the subcutaneous route of injection. The water extract and organic solvent fractions of the pharmaceutical composition of the present invention (vehicle control) are respectively constituted in a concentration of 0.6 mg/ml and then administered for 14 days to albino rats in an amount of 1 ml per kg of body weight once a day to determine the inhibitory effect on edema. Edema is measured daily using a precision gauge, and photographs taken.

Similar studies may be done in the collagen model of arthritis (Myers, L. K. (1997), Life Sci. 61(19): 1861-1878).

Example 5

Effect of the Sporozoite or CSP or Fragment on Cytokine Profile

Kupffer cells are isolated as described above and are incubated with either sporozoites or with purified CSP or an analogue, variant, derivative or fragment of any of these, or a combination of any of these using the procedures and amounts described above. One may also use a culture of macrophages or blood monocytes or a macrophage cell line such as the RAW264.7 or others that are commercially available and known to those skilled in the art. The cells are incubated with various concentrations of sporozoites or CSP or fragments thereof for various periods of time and the supernatants are collected and assayed for IL-6, IL-10, IL-12, TGF-beta and TNF-alpha using a cytometric bead array, ELISA assay, or PCR, or microarray assay. The controls used are uninfected salivary glands, LPS and interferon gamma. The ratio of the expression levels of inflammatory (IL-6, IL-12, TNF-alpha) to anti-inflammatory (IL-10, TGF-beta) cytokines is determined. In addition, the cells are determined by live-dead cell staining and apoptosis assays to obtain insight as to their fate after parasite contact. The cytokines are measured with a mouse Inflammatory Cytometric Bead Array Kit from Becton Dickinson Biosciences Pharmingen: bio-compare.com/productdetails/161157/item/compare/122/mouseInflammatory-Cytokine-Cytometric-Bead-Array-Kit-BD-from-BD-Biosciences-Pharmingen However, any other method known to those skilled in the art may be used, including an ELISA assay or a PCR assay.

What is claimed is:

1. A method for reducing Kupffer cell-mediated inflammation in the liver of a subject suffering from an inflammatory liver disease or disorder associated with Kupffer cell activation by suppressing Kupffer cell activation comprising the steps of:

a) obtaining an isolated and substantially purified circumsporozoite protein (CSP) of a Plasmodium species selected from *P. falciparum, P. vivax, P. malariae, P. berghei* and *P. Yoelii*, and comprising any of SEQ ID NOS: 2, 4, 14, 16 or 18, or a fragment thereof comprising the Region I and Region II-plus motifs thereof as set out in SEQ ID NOS: 21-30 and 31-40;

b) administering the CSP, or the fragment thereof of (a) in an amount that suppresses Kupffer cell activation to a subject in need thereof; and c) monitoring the subject for reduced inflammation by measuring blood levels of liver enzymes; wherein the subject exhibits elevated liver enzymes and wherein reducing Kupffer-cell mediated inflammation in the subject with the CSP, or the fragment thereof results in normalizing liver enzyme levels.

2. The method of claim 1, wherein the liver disease is characterized by fibrosis or cirrhosis.

3. The method of claim 1, wherein the liver disease is induced by a viral, parasitic, or a bacterial infection which is blood-borne or attacks cells in the liver.

4. The method of claim 1, wherein the liver disease is characterized by destruction of hepatocytes or is a result of treatment with a hepatotoxic drug.

5. The method of claim 1, wherein the liver disease or condition is selected from the group consisting of parasitic infections of the liver, bacterial infections of the liver, fulminant hepatitis, chronic hepatitis, viral hepatitis, alcoholic hepatitis, hepatic fibrosis, liver cirrhosis, hepatic cancer, autoimmune hepatitis, drug allergic hepatopathy and primary biliary cirrhosis.

6. The method of any one of claim 1, 2, 3, 4 or 5, wherein the CSP comprises the amino acid sequence of any one of SEQ ID NOS: 2, 21, or 31.

7. A method for ameliorating Kupffer-cell mediated inflammation in an inflammation-associated disorder of the liver, comprising contacting Kupffer cells in the liver with an amount that suppresses Kupffer cell activation of an isolated and substantially purified, or a recombinant circumsporozoite protein (CSP) of a Plasmodium species selected from *P. falciparum, P. vivax, P. malariae, P. berghei* and *P. Yoelii*, and comprising any of SEQ ID NOS: 2, 4, 14, 16 or 18 or a fragment thereof comprising the Region I and Region II-plus motifs thereof as set out in SEQ ID NOS: 21-30 and 31-40, thereby ameliorating Kupffer-cell mediated inflammation in the inflammation-associated disorder.

8. The method of claim 7, wherein the inflammation-associated disorder is due to an inflammatory disease.

9. The method of claim 1 or 7 wherein the CSP is a *P. falciparum* CSP as set out in SEQ ID NO: 2.

10. The method of claim 1 or 7 wherein a fragment of the circumsporozoite protein comprises the amino acid sequence as set forth in SEQ ID NO: 21 and SEQ ID NO: 31.

11. The method of claim 7 wherein the CSP comprises the amino acid sequence of any one of SEQ ID NOS: 2, 21, or 31.

* * * * *

SEQUENCE LISTING

<160> NUMBER OF SEQ ID NOS: 48

<210> SEQ ID NO 1
<211> LENGTH: 1125
<212> TYPE: DNA
<213> ORGANISM: Plasmodium falciparum

<400> SEQUENCE: 1

```
gttgaggcct tattccagga ataccagtgc tatggaagtt cgtcaaatac aagggttcta      60
aatgaattaa attatgataa tgcaggcact aatttatata atgaattaga aatgaattat     120
tatgggaaac aggaaaattg gtatagtctt aaaaaaaata gtagatcact tggagaaaat     180
gatgatggaa ataacgaaga caacgagaaa ttaaggaaac caaaacataa aaaattaaag     240
caaccagggg atggtaatcc tgatccaaat gcaaacccaa atgtagatcc caatgccaac     300
ccaaatgtag atccaaatgc aaacccaaat gtagatccaa atgcaaaccc aaatgcaaac     360
ccaaatgcaa acccaaatgc aaacccaaat gcaaacccaa atgcaaaccc aaatgcaaac     420
ccaaatgcaa accccaatgc aaatcctaat gcaaatccta atgcaaaccc aaatgcaaat     480
cctaatgcaa acccaaatgc aaacccaaac gtagatccta atgcaaatcc aaatgcaaac     540
ccaaatgcaa acccaaacgc aaacccccaat gcaaatccta atgcaaaccc caatgcaaat     600
cctaatgcaa atcctaatgc caatccaaat gcaaatccaa atgcaaaccc aaacgcaaac     660
cccaatgcaa atcctaatgc caatccaaat gcaaatccaa atgcaaaccc aaatgcaaac     720
ccaaatgcaa accccaatgc aaatcctaat aaaaacaatc aaggtaatgg acaaggtcac     780
aatatgccaa atgacccaaa ccgaaatgta gatgaaaatg ctaatgccaa caatgctgta     840
aaaaataata ataacgaaga accaagtgat aagcacatag aacaatattt aaagagaata     900
caaaattctc tttcaactga atggtcccca tgtagtgtaa cttgtggaaa tggtattcaa     960
gttagaataa agcctggctc tgctaataaa cctaagacc aattagatta tgcaaatgat    1020
attgaaaaaa aaatttgtaa aatggaaaaa tgttccagtg tgtttaatgt cgtaaatagt    1080
tcaataggat taataatggt attatccttc ttgttcctta attag                   1125
```

<210> SEQ ID NO 2
<211> LENGTH: 374
<212> TYPE: PRT
<213> ORGANISM: Plasmodium falciparum

<400> SEQUENCE: 2

Val Glu Ala Leu Phe Gln Glu Tyr Gln Cys Tyr Gly Ser Ser Asn
1               5                   10                  15

Thr Arg Val Leu Asn Glu Leu Asn Tyr Asp Asn Ala Gly Thr Asn Leu
            20                  25                  30

Tyr Asn Glu Leu Glu Met Asn Tyr Tyr Gly Lys Gln Glu Asn Trp Tyr
        35                  40                  45

Ser Leu Lys Lys Asn Ser Arg Ser Leu Gly Glu Asn Asp Asp Gly Asn
    50                  55                  60

Asn Glu Asp Asn Glu Lys Leu Arg Lys Pro His Lys Lys Leu Lys
65                  70                  75                  80

Gln Pro Gly Asp Gly Asn Pro Asp Pro Asn Ala Asn Pro Asn Val Asp
                85                  90                  95

Pro Asn Ala Asn Pro Asn Val Asp Pro Asn Ala Asn Pro Asn Val Asp
            100                 105                 110

Pro Asn Ala Asn Pro Asn Ala Asn Pro Asn Ala Asn Pro Asn Ala Asn
            115                 120                 125

Pro Asn Ala Asn Pro Asn Ala Asn Pro Asn Ala Asn Pro Asn Ala Asn
            130                 135                 140

Pro Asn Ala Asn Pro Asn Ala Asn Pro Asn Ala Asn Pro Asn Ala Asn
145                 150                 155                 160

Pro Asn Ala Asn Pro Asn Ala Asn Pro Asn Val Asp Pro Asn Ala Asn
            165                 170                 175

Pro Asn Ala Asn Pro Asn Ala Asn Pro Asn Ala Asn Pro Asn Ala Asn
            180                 185                 190

Pro Asn Ala Asn Pro Asn Ala Asn Pro Asn Ala Asn Pro Asn Ala Asn
            195                 200                 205

Pro Asn Ala Asn Pro Asn Ala Asn Pro Asn Ala Asn Pro Asn Ala Asn
            210                 215                 220

Pro Asn Ala Asn Pro Asn Ala Asn Pro Asn Ala Asn Pro Asn Ala Asn
225                 230                 235                 240

Pro Asn Ala Asn Pro Asn Ala Asn Pro Asn Lys Asn Asn Gln Gly Asn
            245                 250                 255

Gly Gln Gly His Asn Met Pro Asn Asp Pro Asn Arg Asn Val Asp Glu
            260                 265                 270

Asn Ala Asn Ala Asn Ala Asn Val Lys Asn Asn Asn Glu Glu Pro
            275                 280                 285

Ser Asp Lys His Ile Glu Gln Tyr Leu Lys Arg Ile Gln Asn Ser Leu
    290                 295                 300

Ser Thr Glu Trp Ser Pro Cys Ser Val Thr Cys Gly Asn Gly Ile Gln
305                 310                 315                 320

Val Arg Ile Lys Pro Gly Ser Ala Asn Lys Pro Lys Asp Gln Leu Asp
            325                 330                 335

Tyr Ala Asn Asp Ile Glu Lys Lys Ile Cys Lys Met Glu Lys Cys Ser
            340                 345                 350

Ser Val Phe Asn Val Val Asn Ser Ser Ile Gly Leu Ile Met Val Leu
            355                 360                 365

Ser Phe Leu Phe Leu Asn
    370

<210> SEQ ID NO 3
<211> LENGTH: 681
<212> TYPE: DNA
<213> ORGANISM: Plasmodium vivax

<400> SEQUENCE: 3

-continued

```
cacaatgtag atctgtccaa ggccataaat ttaaatggag taaacttcaa taatgtagac    60
gccagttcac ttggcgcggc acacgtagga caaagtgcta gccgaggcag aggacttggt   120
gagaacccag atgacgagga aggagatgct aaaaaaaaaa aggatggaaa gaaagcagaa   180
ccaaaaaatc cacgtgaaaa taagctgaaa caaccaggag acagagcaga tggacagcca   240
gcaggagaca gagcagatgg acagccagca ggagatagag cagctggaca ggcagcagga   300
aatggtgcag gtggacaggc agcaggagga aatgcagcaa acaagaaggc agaagacgca   360
ggaggaaacg caggaggaaa cgcaggagga cagggacaaa ataatgaagg tgcgaatgcc   420
ccaaatgaaa agtctgtgaa agaataccta gataaagtta gagctaccgt tggcaccgaa   480
tggactccat gcagtgtaac ctgtggagtg ggtgtaagag tcagaagaag agttaatgca   540
gctaacaaaa aaccagagga tcttactttg aatgaccttg agactgatgt ttgtacaatg   600
gataagtgtg ctggcatatt taacgttgtg agtaattcat tacggctagg catattgtta   660
tgcctagcat tattcaatta a                                             681
```

<210> SEQ ID NO 4
<211> LENGTH: 226
<212> TYPE: PRT
<213> ORGANISM: Plasmodium vivax

<400> SEQUENCE: 4

```
His Asn Val Asp Leu Ser Lys Ala Ile Asn Leu Asn Gly Val Asn Phe
  1               5                  10                  15

Asn Asn Val Asp Ala Ser Ser Leu Gly Ala Ala His Val Gly Gln Ser
             20                  25                  30

Ala Ser Arg Gly Arg Gly Leu Gly Glu Asn Pro Asp Asp Glu Glu Gly
         35                  40                  45

Asp Ala Lys Lys Lys Asp Gly Lys Ala Glu Pro Lys Asn Pro
     50                  55                  60

Arg Glu Asn Lys Leu Lys Gln Pro Gly Asp Arg Ala Asp Gly Gln Pro
 65                  70                  75                  80

Ala Gly Asp Arg Ala Asp Gly Gln Pro Ala Gly Asp Arg Ala Ala Gly
                 85                  90                  95

Gln Ala Ala Gly Asn Gly Ala Gly Gln Ala Ala Gly Asn Ala
            100                 105                 110

Ala Asn Lys Lys Ala Glu Asp Ala Gly Gly Asn Ala Gly Asn Ala
            115                 120                 125

Gly Gly Gln Gly Gln Asn Asn Glu Gly Ala Asn Ala Pro Asn Glu Lys
        130                 135                 140

Ser Val Lys Glu Tyr Leu Asp Lys Val Arg Ala Thr Val Gly Thr Glu
145                 150                 155                 160

Trp Thr Pro Cys Ser Val Thr Cys Gly Val Gly Val Arg Val Arg Arg
                165                 170                 175

Arg Val Asn Ala Ala Asn Lys Lys Pro Glu Asp Leu Thr Leu Asn Asp
            180                 185                 190

Leu Glu Thr Asp Val Cys Thr Met Asp Lys Cys Ala Gly Ile Phe Asn
        195                 200                 205

Val Val Ser Asn Ser Leu Arg Leu Gly Ile Leu Leu Cys Leu Ala Leu
    210                 215                 220

Phe Asn
225
```

<210> SEQ ID NO 5
<211> LENGTH: 1161
<212> TYPE: DNA
<213> ORGANISM: Plasmodium simium

<400> SEQUENCE: 5

```
atgaagaact tcattctctt ggctgtttct tccatcctgt tggtggactt gttccccacg       60
cactgcgggc acaatgtaga tctgtccaag gccataaatt taaatggagt aaacttcaat      120
aatgtagacg ccagttcact tggcgcggca cacgtaggac aaagtgctag ccgaggcaga      180
ggacttggtg agaacccaga tgacgaggaa ggagatgcta aaaaaaaaaa ggatggaaag      240
aaagcagaac caaaaaatcc acgtgaaaat aagctgaaac aaccaggaga cagagcagat      300
ggacagccag caggagacag agcagatgga cagccagcag agacagagc agatggacag       360
ccagcaggtg atagagcaga tggacaacca gcaggtgata gagcagatgg acaaccagca      420
ggagatagag cagctggaca gccagcagga gatagagcag atggacagcc agcaggagac      480
agagcagatg gacagccagc aggtgataga gcagctggac agccagcagg tgatagagca      540
gctggacagc cagcaggcga tagagcagat ggacagccag caggcgatag agcagatgga      600
cagccagcag gagatagagc agatggacag ccagcaggat atagagcagc tggacagcca      660
gcaggagata gagcagctgg acaaccagca ggtgatagag cagctggaca accagcagga      720
gatagagcag ctggacagcc agcaggagat agagcagctg gacagccagc aggagataga      780
gcagctggac agccagcagg atatagagca gctggacagc cagcaggaaa tggtgcaggt      840
ggacaggcag caggaggaaa cgcaggagga cagggacaaa ataatgaagg tgcgaatgcc      900
ccaaatgaaa agtctgtgaa agaatatcta gataaagtta gagctaccgt tggcaccgaa      960
tggactccat gcagtgtaac ctgtggagtg ggtgtaagag tcagaagaag agttaatgca     1020
gctaacaaaa aaccagagga tcttactttg aatgaccttg agactgatgt ttgtacaatg     1080
gataagtgtg ctggcatatt taacgttgtg agtaattcat tagggctagt catattgtta     1140
gtcctagcat tattcaatta a                                               1161
```

<210> SEQ ID NO 6
<211> LENGTH: 386
<212> TYPE: PRT
<213> ORGANISM: Plasmodium simium

<400> SEQUENCE: 6

```
Met Lys Asn Phe Ile Leu Leu Ala Val Ser Ser Ile Leu Leu Val Asp
 1               5                  10                  15

Leu Phe Pro Thr His Cys Gly His Asn Val Asp Leu Ser Lys Ala Ile
            20                  25                  30

Asn Leu Asn Gly Val Asn Phe Asn Asn Val Asp Ala Ser Ser Leu Gly
        35                  40                  45

Ala Ala His Val Gly Gln Ser Ala Ser Arg Gly Arg Gly Leu Gly Glu
    50                  55                  60

Asn Pro Asp Asp Glu Glu Gly Asp Ala Lys Lys Lys Asp Gly Lys
65                  70                  75                  80

Lys Ala Glu Pro Lys Asn Pro Arg Glu Asn Lys Leu Lys Gln Pro Gly
                85                  90                  95

Asp Arg Ala Asp Gly Gln Pro Ala Gly Asp Arg Ala Asp Gly Gln Pro
            100                 105                 110

Ala Gly Asp Arg Ala Asp Gly Gln Pro Ala Gly Asp Arg Ala Asp Gly
        115                 120                 125
```

Gln Pro Ala Gly Asp Arg Ala Asp Gly Gln Pro Ala Gly Asp Arg Ala
            130                 135                 140
Ala Gly Gln Pro Ala Gly Asp Arg Ala Asp Gly Gln Pro Ala Gly Asp
145                 150                 155                 160
Arg Ala Asp Gly Gln Pro Ala Gly Asp Arg Ala Ala Gly Gln Pro Ala
                165                 170                 175
Gly Asp Arg Ala Ala Gly Gln Pro Ala Gly Asp Arg Ala Asp Gly Gln
            180                 185                 190
Pro Ala Gly Asp Arg Ala Asp Gly Gln Pro Ala Gly Asp Arg Ala Asp
                195                 200                 205
Gly Gln Pro Ala Gly Asp Arg Ala Ala Gly Gln Pro Ala Gly Asp Arg
            210                 215                 220
Ala Ala Gly Gln Pro Ala Gly Asp Arg Ala Ala Gly Gln Pro Ala Gly
225                 230                 235                 240
Asp Arg Ala Ala Gly Gln Pro Ala Gly Asp Arg Ala Ala Gly Gln Pro
                245                 250                 255
Ala Gly Asp Arg Ala Ala Gly Gln Pro Ala Gly Asp Arg Ala Ala Gly
            260                 265                 270
Gln Pro Ala Gly Asn Gly Ala Gly Gln Ala Gly Gly Asn Ala
            275                 280                 285
Gly Gly Gln Gly Gln Asn Asn Glu Gly Ala Asn Ala Pro Asn Glu Lys
            290                 295                 300
Ser Val Lys Glu Tyr Leu Asp Lys Val Arg Ala Thr Val Gly Thr Glu
305                 310                 315                 320
Trp Thr Pro Cys Ser Val Thr Cys Gly Val Gly Val Arg Val Arg Arg
                325                 330                 335
Arg Val Asn Ala Ala Asn Lys Lys Pro Glu Asp Leu Thr Leu Asn Asp
            340                 345                 350
Leu Glu Thr Asp Val Cys Thr Met Asp Lys Cys Ala Gly Ile Phe Asn
                355                 360                 365
Val Val Ser Asn Ser Leu Gly Leu Val Ile Leu Leu Val Leu Ala Leu
            370                 375                 380
Phe Asn
385

<210> SEQ ID NO 7
<211> LENGTH: 195
<212> TYPE: DNA
<213> ORGANISM: Plasmodium knowlesi

<400> SEQUENCE: 7
atgaggaact tcattctctt ggccgtctcc tccatcctgc tggtggactt gctccccaca      60
cacttcgaac ataatgtaga tctctccagg gccataaatg taaatggagt aagcttcaat     120
aatgtagaca ccagttcact tggcgcagca caggtaggac aaagtgctag ccgaggcaga     180
ggacttggtg aaaag                                                     195

<210> SEQ ID NO 8
<211> LENGTH: 65
<212> TYPE: PRT
<213> ORGANISM: Plasmodium knowlesi

<400> SEQUENCE: 8

Met Arg Asn Phe Ile Leu Leu Ala Val Ser Ser Ile Leu Leu Val Asp
1               5                   10                  15
Leu Leu Pro Thr His Phe Glu His Asn Val Asp Leu Ser Arg Ala Ile 20                  25                  30
Asn Val Asn Gly Val Ser Phe Asn Asn Val Asp Thr Ser Ser Leu Gly
            35                  40                  45

Ala Ala Gln Val Gly Gln Ser Ala Ser Arg Gly Arg Gly Leu Gly Glu
    50                  55                  60

Lys
65

<210> SEQ ID NO 9
<211> LENGTH: 1335
<212> TYPE: DNA
<213> ORGANISM: Plasmodium cynomolgi

<400> SEQUENCE: 9
agcggcttaa gcaaaacagc caaagaccta caagcgtaaa aaatcttcct gctcatactt        60
acatacaaga acaagatgaa gaacttcaat ctcttagccg tttcttccat cctgttggtg       120
gacttgttcc gcacacactg gggacataat gtagatttct ccaaggccat aaatttaaat       180
ggagtaagct tcagtaatgt agacgccagt tcacttggcg cagcacaggt aagacaaagt       240
gctagccgag gcagaggact tggtgagaac caaaagaag aggacggagc tgataaaaaa        300 aaaaaaagg acgaaaaaca agtagaacca aaaagccac gtgaaaataa gctgaaacaa         360
ccagtagaaa acgcagacgg aaacgcagga ggaaacgcag gaggaaacgc aggaggaaac       420
gcaggaggaa acgcaggagg aaacgcagac ggaaacgcag gaggaaacgc aggaggaaac       480
gcaggaggaa acgcaggagg aaacgcagga ggaaacgcag acggaaacgc aggaggaaac       540
gcagacggaa acgcaggagg aaatgcagac ggaaacgctg gaggaaacgc aggaggaaac       600
gcaggaggaa atgcagacgg aaacgctgga ggaaacgcag gaggaaacgc aggaggaaac       660
gcaggaggaa atgcaggagg aaacgctgga ggaaacgcag gaggaaatgc agacggaaac       720
gctggaggaa acgcaggagg aaatgcagga ggaaacgcag acggaaacgc tggaggaaac       780
gctggaggaa acgcaggagg aaacgcagga ggaaacgcag gaggaactgc aggaggaaac       840
gcagacggaa acgcaggagg aaacgcagga ggtaacgcgg gaggtaacgc aggaggtaac       900
gcaggaggta acgcaggagg taacgcagga ggtaacgcag gaggtaacgc aggaggtaac       960
gcaggaggaa acgcaggagg aaacgcagga ggaaacgcag gagccaatgc gggaaataaa      1020
aaagcaggag acgcaggagc aggacaggga caaaataatg aagctgcgaa tatgccaaat      1080
gtaaagcttg tgaaagaata cctagacaaa attagatcta ccattagcac cgagtggagt      1140
ccatgcagtg taacctgtgg aaagggtgta agaatgagaa aaaaagttag tgcagctaac      1200
aaaaaaccag aagagcttga tgtgaatgac cttgagacag aagtttgtac aatggataag      1260
tgcgctggca tatttaacgt tgtgagtaat tcattacggt tagtcatatt gttagtccta      1320
gcattattca attaa                                                       1335

<210> SEQ ID NO 10
<211> LENGTH: 418
<212> TYPE: PRT
<213> ORGANISM: Plasmodium cynomolgi

<400> SEQUENCE: 10

Met Lys Asn Phe Asn Leu Leu Ala Val Ser Ser Ile Leu Leu Val Asp
1               5                   10                  15

Leu Phe Arg Thr His Trp Gly His Asn Val Asp Phe Ser Lys Ala Ile
            20                  25                  30

```
Asn Leu Asn Gly Val Ser Phe Ser Asn Val Asp Ala Ser Leu Gly Ala
         35                  40                  45

Ala Gln Val Arg Gln Ser Ala Ser Arg Gly Arg Gly Leu Gly Glu Asn
 50                  55                  60

Pro Lys Glu Glu Asp Gly Ala Asp Lys Lys Lys Lys Asp Glu Lys
 65                  70                  75                  80

Gln Val Glu Pro Lys Lys Pro Arg Glu Asn Lys Leu Lys Gln Pro Val
                 85                  90                  95

Glu Asn Ala Asp Gly Asn Ala Gly Gly Asn Ala Gly Gly Asn Ala Gly
            100                 105                 110

Gly Asn Ala Gly Gly Asn Ala Gly Gly Asn Ala Asp Gly Asn Ala Gly
        115                 120                 125

Gly Asn Ala Gly Gly Asn Ala Gly Gly Asn Ala Gly Gly Asn Ala Gly
        130                 135                 140

Gly Asn Ala Asp Gly Asn Ala Gly Gly Asn Ala Asp Gly Asn Ala Gly
145                 150                 155                 160

Gly Asn Ala Asp Gly Asn Ala Gly Gly Asn Ala Gly Gly Asn Ala Gly
                165                 170                 175

Gly Asn Ala Asp Gly Asn Ala Gly Gly Asn Ala Gly Gly Asn Ala Gly
            180                 185                 190

Gly Asn Ala Gly Gly Asn Ala Gly Gly Asn Ala Gly Gly Asn Ala Gly
        195                 200                 205

Gly Asn Ala Asp Gly Asn Ala Gly Gly Asn Ala Gly Gly Asn Ala Gly
        210                 215                 220

Gly Asn Ala Asp Gly Asn Ala Gly Gly Asn Ala Gly Gly Asn Ala Gly
225                 230                 235                 240

Gly Asn Ala Gly Gly Asn Ala Gly Gly Thr Ala Gly Gly Asn Ala Asp
                245                 250                 255

Gly Asn Ala Gly Gly Asn Ala Gly Gly Asn Ala Gly Gly Asn Ala Gly
            260                 265                 270

Gly Asn Ala Gly Gly Asn Ala Gly Gly Asn Ala Gly Gly Asn Ala Gly
        275                 280                 285

Gly Asn Ala Gly Gly Asn Ala Gly Gly Asn Ala Gly Gly Asn Ala Gly
        290                 295                 300

Gly Asn Ala Gly Ala Asn Ala Gly Asn Lys Lys Ala Gly Asp Ala Gly
305                 310                 315                 320

Ala Gly Gln Gly Gln Asn Asn Glu Ala Ala Asn Met Pro Asn Val Lys
                325                 330                 335

Leu Val Lys Glu Tyr Leu Asp Lys Ile Arg Ser Thr Ile Ser Thr Glu
            340                 345                 350

Trp Ser Pro Cys Ser Val Thr Cys Gly Lys Gly Val Arg Met Arg Lys
        355                 360                 365

Lys Val Ser Ala Ala Asn Lys Lys Pro Glu Glu Leu Asp Val Asn Asp
370                 375                 380

Leu Glu Thr Glu Val Cys Thr Met Asp Lys Cys Ala Gly Ile Phe Asn
385                 390                 395                 400

Val Val Ser Asn Ser Leu Arg Leu Val Ile Leu Leu Val Leu Ala Leu
                405                 410                 415

Phe Asn

<210> SEQ ID NO 11
<211> LENGTH: 1345
<212> TYPE: DNA
<213> ORGANISM: Plasmodium brasilianum
```

<400> SEQUENCE: 11

```
agctgttgaa ataaaattga acaacccccc cggagatgat gatgacgcag gaaatgatga      60
aggaaatgat gcaggaaatg atgcaggaaa tgcagcagga aatgcagcag gaaatgcagc     120
aggaaatgca gcaggtaacg cagcaggtaa cgcagcagga aatgcagcag gaaatgcagc     180
aggtaacgca gcaggaaatg cagcaggaaa tgatgcagga aatgcagcag gtaacgcagc     240
aggaaatgca gcaggaaatg cagcaggtaa cgcagcaggt aacgcagcag gaaatgcagc     300
aggaaatgca gcaggtaacg cagcaggaaa tgcagcagga aatgatgcag gaaatgcagc     360
aggtaacgca gcaggaaatg cagcaggaaa tgcagcagga aatgcagcag gaaatgcagc     420
aggaaatgat gcaggaaatg cagcaggaaa tgcagcagga aatgcagcag gtaacgcagc     480
aggaaatgca gcaggaaatg cagcaggtaa cgcagcaggt aacgcagcag gaaatgcagc     540
aggaaatgca gcaggaaatg atgcaggaaa tgcagcaggt aacgcagcag gaaatgcagc     600
aggaaatgca gcaggaaatg cagcaggtaa cgcagcaggt aacgcagcag gaaatgcagc     660
aggaaatgca gcaggaaatg cagcaggaaa tgcagcaggt aacgcagcag gaaatgcagc     720
aggaaatgca gcaggtaacg cagcaggaaa tgcagcagga aatgcagcag gtaacgcagc     780
aggaaatgca gcaggaaatg cagcaggtaa cgcagcagga aatgcagcag gaaatgaaaa     840
agcgaaaaat aaggataata aagtggatgc aaatacgaat aaaaaggaca accaggaaga     900
aaataatgat tcgtctaatg gtccatctga agaacatata aagaattatt tagaaagtat     960
tcgtaatagt attacggagg aatggtcacc atgtagtgta acttgtggaa gtggtataag    1020
ggctagaaga aaggttgatg caaaaaataa gaaacctgca gaattagttt taagtgacct    1080
tgaaactgaa atttgttcac tagataaatg ctccagtata tttaatgtcg taagtaattc    1140
gttaggaata gtattagttt tagtcttaat actctttcac taaataaata gcatgtatct    1200
ttcgaaatat tatatacata tatatttata tatattttttt ctttcttttt tcttttttt    1260
gtgaatgatt actaatgttt gcacttaatt gtatatatat tatatatatt caatatataa    1320
ttctaaaaat taccagtatt ttaaa                                          1345
```

<210> SEQ ID NO 12
<211> LENGTH: 393
<212> TYPE: PRT
<213> ORGANISM: Plasmodium brasilianum

<400> SEQUENCE: 12

```
Ala Val Glu Asn Lys Leu Lys Gln Pro Pro Gly Asp Asp Asp Ala
  1               5                  10                  15

Gly Asn Asp Glu Gly Asn Asp Ala Gly Asn Asp Ala Gly Asn Ala Ala
                 20                  25                  30

Gly Asn Ala Ala Gly Asn Ala Ala Gly Asn Ala Ala Gly Asn Ala Ala
         35                  40                  45

Gly Asn Ala Ala Gly Asn Ala Ala Gly Asn Ala Ala Gly Asn Ala Ala
     50                  55                  60

Gly Asn Ala Ala Gly Asn Asp Ala Gly Asn Ala Ala Gly Asn Ala Ala
 65                  70                  75                  80

Gly Asn Ala Ala Gly Asn Ala Ala Gly Asn Ala Ala Gly Asn Ala Ala
                 85                  90                  95

Gly Asn Ala Ala Gly Asn Ala Ala Gly Asn Ala Ala Gly Asn Ala Ala
                100                 105                 110

Gly Asn Asp Ala Gly Asn Ala Ala Gly Asn Ala Ala Gly Asn Ala Ala
```

```
              115                 120                 125
Gly Asn Ala Ala Gly Asn Ala Ala Gly Asn Ala Gly Asn Asp Ala
    130                 135                 140
Gly Asn Ala Ala Gly Asn Ala Ala Gly Asn Ala Ala Gly Asn Ala Ala
145                 150                 155                 160
Gly Asn Ala Ala Gly Asn Ala Ala Gly Asn Ala Ala Gly Asn Ala Ala
                165                 170                 175
Gly Asn Ala Ala Gly Asn Ala Gly Asn Asp Ala Gly Asn Ala Ala
            180                 185                 190
Gly Asn Ala Ala Gly Asn Ala Ala Gly Asn Ala Ala Gly Asn Ala Ala
        195                 200                 205
Gly Asn Ala Ala Gly Asn Ala Ala Gly Asn Ala Ala Gly Asn Ala Ala
    210                 215                 220
Gly Asn Ala Ala Gly Asn Ala Ala Gly Asn Ala Ala Gly Asn Ala Ala
225                 230                 235                 240
Gly Asn Ala Ala Gly Asn Ala Ala Gly Asn Ala Ala Gly Asn Ala Ala
                245                 250                 255
Gly Asn Ala Ala Gly Asn Ala Ala Gly Asn Ala Ala Gly Asn Ala Ala
            260                 265                 270
Gly Asn Ala Ala Gly Asn Glu Lys Ala Lys Asn Lys Asp Asn Lys Val
        275                 280                 285
Asp Ala Asn Thr Asn Lys Lys Asp Asn Gln Glu Glu Asn Asn Asp Ser
    290                 295                 300
Ser Asn Gly Pro Ser Glu Glu His Ile Lys Asn Tyr Leu Glu Ser Ile
305                 310                 315                 320
Arg Asn Ser Ile Thr Glu Glu Trp Ser Pro Cys Ser Val Thr Cys Gly
                325                 330                 335
Ser Gly Ile Arg Ala Arg Arg Lys Val Asp Ala Lys Asn Lys Lys Pro
            340                 345                 350
Ala Glu Leu Val Leu Ser Asp Leu Gly Thr Glu Ile Cys Ser Leu Asp
        355                 360                 365
Lys Cys Ser Ser Ile Phe Asn Val Val Ser Asn Ser Leu Gly Ile Val
    370                 375                 380
Leu Val Leu Val Leu Ile Leu Phe His
385                 390

<210> SEQ ID NO 13
<211> LENGTH: 1326
<212> TYPE: DNA
<213> ORGANISM: Plasmodium malariae

<400> SEQUENCE: 13
atgaagaagt tatctgtctt agcaatatcc tcttttttaa ttgttgattt cctcttccct    60
ggatatcatc acaactcaaa ttccaccaag tcaagaaatt taagtgagtt gtgttacaat   120
aatgtggaca ctaaattatt taatgagtta gaagtcagat atagcacgaa tcaagatcat   180
ttctataact ataataagac aatcagatta cttaatgaaa ataacaatga aaaagatgga   240
aatgtgacca atgaaagaaa aaaaaaaccc acaaaagctg ttgaaaataa attgaaacaa   300
cccccccgga gatgatgatgg cgcaggaaat gatgaaggaa atgatgcagg aaatgatgca   360
ggaaatgcag caggaaatgc agcaggtaac gcagcaggaa atgcagcagg aaatgatgca   420
ggaaatgcag caggaaatga tgcaggaaat gcagcaggaa atgatgcagg aaatgcagca   480
ggtaacgcag caggaaatgc agcaggaaat gcagcaggga atgcagcagg taacgcagca   540
```

```
ggtaacgcag caggaaatgc agcaggaaat gcagcaggaa atgatgcagg aaatgcagca    600
ggtaacgcag caggaaatgc agcaggaaat gcagcaggaa atgcagcagg taacgcagca    660
ggtaacgcag caggaaatgc agcaggaaat gcagcaggta acgcagcagg aaatgcagca    720
ggaaatgatg caggaaatgc agcaggtaac gcagcaggaa atgcagcagg aaatgcagca    780
ggaaatgcag caggaaatgc agcaggaaat gcagcaggaa atgcagcagg taacgcagca    840
ggaaatgcag caggaaatgc agcaggtaac gcagcaggaa atgcagcagg aaatgcagca    900
ggtaacgcag caggaaatgc agcaggaaat gcagcaggta acgcagcagg aaatgcagca    960
ggaaatgcag caggaaatga aaagcgaaa ataaggata ataaagtgga tgcaaatacg     1020
aataaaaagg acaatcaggg agaaaataat gattcgtcta atggtccatc tgaagaacat    1080
ataaagaatt atttagaaag tattcgtaat agtattacgg aggaatggtc accatgtagt    1140
gtaacttgtg aagtggtat aagggctaga agaaaggttg atgcaaaaaa taagaaacct     1200
gcagaattag ttttaagtga ccttgaaact gaaatttgtt cactagataa atgctccagt    1260
atatttaatg tcgtaagtaa ttcgttagga atagtattag ttttagtctt aatactcttt    1320
cactaa                                                              1326
```

<210> SEQ ID NO 14
<211> LENGTH: 441
<212> TYPE: PRT
<213> ORGANISM: Plasmodium malariae

<400> SEQUENCE: 14

```
Met Lys Lys Leu Ser Val Leu Ala Ile Ser Ser Phe Leu Ile Val Asp
 1               5                  10                  15

Phe Leu Phe Pro Gly Tyr His His Asn Ser Asn Ser Thr Lys Ser Arg
            20                  25                  30

Asn Leu Ser Glu Leu Cys Tyr Asn Asn Val Asp Thr Lys Leu Phe Asn
        35                  40                  45

Glu Leu Glu Val Arg Tyr Ser Thr Asn Gln Asp His Phe Tyr Asn Tyr
    50                  55                  60

Asn Lys Thr Ile Arg Leu Leu Asn Glu Asn Asn Glu Lys Asp Gly
65                  70                  75                  80

Asn Val Thr Asn Glu Arg Lys Lys Pro Thr Lys Ala Val Glu Asn
                85                  90                  95

Lys Leu Lys Gln Pro Pro Gly Asp Asp Asp Gly Ala Gly Asn Asp Glu
            100                 105                 110

Gly Asn Asp Ala Gly Asn Asp Ala Gly Asn Ala Ala Gly Asn Ala Ala
        115                 120                 125

Gly Asn Ala Ala Gly Asn Ala Ala Gly Asn Asp Ala Gly Asn Ala Ala
    130                 135                 140

Gly Asn Asp Ala Gly Asn Ala Ala Gly Asn Asp Ala Gly Asn Ala Ala
145                 150                 155                 160

Gly Asn Ala Ala Gly Asn Ala Ala Gly Asn Ala Ala Gly Asn Ala Ala
                165                 170                 175

Gly Asn Ala Ala Gly Asn Ala Ala Gly Asn Ala Ala Gly Asn Ala Ala
            180                 185                 190

Gly Asn Asp Ala Gly Asn Ala Ala Gly Asn Ala Ala Gly Asn Ala Ala
        195                 200                 205

Gly Asn Ala Ala Gly Asn Ala Ala Gly Asn Ala Ala Gly Asn Ala Ala
    210                 215                 220

Gly Asn Ala Ala Gly Asn Ala Ala Gly Asn Ala Ala Gly Asn Ala Ala
```

```
                  225                 230                 235                 240
Gly Asn Asp Ala Gly Asn Ala Ala Gly Asn Ala Ala Gly Asn Ala Ala
                245                 250                 255

Gly Asn Ala Ala Gly Asn Ala Ala Gly Asn Ala Ala Gly Asn Ala Ala
                260                 265                 270

Gly Asn Ala Ala Gly Asn Ala Ala Gly Asn Ala Ala Gly Asn Ala Ala
                275                 280                 285

Gly Asn Ala Ala Gly Asn Ala Ala Gly Asn Ala Ala Gly Asn Ala Ala
                290                 295                 300

Gly Asn Ala Ala Gly Asn Ala Ala Gly Asn Ala Ala Gly Asn Ala Ala
305                 310                 315                 320

Gly Asn Ala Ala Gly Asn Glu Lys Ala Lys Asn Lys Asp Asn Lys Val
                325                 330                 335

Asp Ala Asn Thr Asn Lys Lys Asp Asn Gln Gly Glu Asn Asn Asp Ser
                340                 345                 350

Ser Asn Gly Pro Ser Glu Glu His Ile Lys Asn Tyr Leu Glu Ser Ile
                355                 360                 365

Arg Asn Ser Ile Thr Glu Glu Trp Ser Pro Cys Ser Val Thr Cys Gly
                370                 375                 380

Ser Gly Ile Arg Ala Arg Arg Lys Val Asp Ala Lys Asn Lys Lys Pro
385                 390                 395                 400

Ala Glu Leu Val Leu Ser Asp Leu Glu Thr Glu Ile Cys Ser Leu Asp
                405                 410                 415

Lys Cys Ser Ser Ile Phe Asn Val Val Ser Asn Ser Leu Gly Ile Val
                420                 425                 430

Leu Val Leu Val Leu Ile Leu Phe His
                435                 440

<210> SEQ ID NO 15
<211> LENGTH: 1044
<212> TYPE: DNA
<213> ORGANISM: Plasmodium berghei

<400> SEQUENCE: 15
atgaagaagt gtaccatttt agttgtagcg tcacttttat tagttaattc tctacttcca     60
ggatatggac aaaataaaag catccaagcc caaggaact  taaacgagct atgttacaat    120
gaaggaaatg ataataaatt gtatcacgtg cttaactcta agaatggaaa aatatacata    180
cgaaatacag tcaacagatt acttgccgat gctcccgaag gaaaaaaaaa tgagaaaaaa    240
aacaaaatag agcgtaataa taaattgaaa caaccaccac caccaccaaa cccaaatgac    300
ccaccaccac aaacccaaa  tgacccacca ccaccaaacc caaatgaccc accaccacca    360
aacccaaatg acccaccacc accaaaccca aatgacccac caccaccaaa cgcaaatgac    420
ccaccaccac aaacgcaaa  tgacccagca ccaccaaacg caaatgaccc agcaccacca    480
aacgcaaatg acccagcacc accaaacgca aatgacccac caccaccaaa cgcaaatgac    540
ccaccaccac aaacccaaa  tgacccagca ccaccaaacg caaatgaccc accaccacca    600
aacccaaatg acccagcacc accacaagga ataacaatc  cacaaccaca gccacggccg    660
cagccacaac acagccaca  gccacaacca gcacacagc  cacaaccaca gccacgacca    720
cagccacaac acagccagg  tggtaataac aataacaaaa ataataataa tgacgattct    780
tatatcccaa gcgcggaaaa aatactagaa tttgttaaac agatcaggga tagtatcaca    840
gaggaatggt ctcaatgtaa cgtaacatgt ggttctggta taagagttag aaaacgaaaa    900
```

```
ggttcaaata agaaagcaga agatttgacc ttagaagata ttgatactga aatttgtaaa       960
atggataaat gttcaagtat atttaatatt gtaagcaatt cattaggatt tgtaatatta      1020
ttagtattag tattctttaa ttaa                                             1044
```

<210> SEQ ID NO 16
<211> LENGTH: 347
<212> TYPE: PRT
<213> ORGANISM: Plasmodium berghei

<400> SEQUENCE: 16

```
Met Lys Lys Cys Thr Ile Leu Val Val Ala Ser Leu Leu Leu Val Asn
 1               5                  10                  15

Ser Leu Leu Pro Gly Tyr Gly Gln Asn Lys Ser Ile Gln Ala Gln Arg
            20                  25                  30

Asn Leu Asn Glu Leu Cys Tyr Asn Glu Gly Asn Asp Asn Lys Leu Tyr
        35                  40                  45

His Val Leu Asn Ser Lys Asn Gly Lys Ile Tyr Ile Arg Asn Thr Val
    50                  55                  60

Asn Arg Leu Leu Ala Asp Ala Pro Glu Gly Lys Lys Asn Glu Lys Lys
65                  70                  75                  80

Asn Lys Ile Glu Arg Asn Asn Lys Leu Lys Gln Pro Pro Pro Pro Pro
                85                  90                  95

Asn Pro Asn Asp Pro Pro Pro Asn Pro Asn Asp Pro Pro Pro Pro
            100                 105                 110

Asn Pro Asn Asp Pro Pro Pro Asn Pro Asn Asp Pro Pro Pro
        115                 120                 125

Asn Pro Asn Asp Pro Pro Pro Asn Ala Asn Asp Pro Pro Pro Pro
    130                 135                 140

Asn Ala Asn Asp Pro Ala Pro Pro Asn Ala Asn Asp Pro Ala Pro Pro
145                 150                 155                 160

Asn Ala Asn Asp Pro Ala Pro Pro Asn Ala Asn Asp Pro Pro Pro Pro
                165                 170                 175

Asn Ala Asn Asp Pro Pro Pro Asn Pro Asn Asp Pro Ala Pro Pro
            180                 185                 190

Asn Ala Asn Asp Pro Pro Pro Asn Pro Asn Asp Pro Ala Pro Pro
        195                 200                 205

Gln Gly Asn Asn Asn Pro Gln Pro Gln Pro Arg Pro Gln Pro Gln Pro
    210                 215                 220

Gln Pro Gln Pro Gln Pro Gln Pro Gln Pro Gln Pro Arg Pro
225                 230                 235                 240

Gln Pro Gln Pro Gln Pro Gly Gly Asn Asn Asn Lys Asn Asn Asn
                245                 250                 255

Asn Asp Asp Ser Tyr Ile Pro Ser Ala Glu Lys Ile Leu Glu Phe Val
            260                 265                 270

Lys Gln Ile Arg Asp Ser Ile Thr Glu Glu Trp Ser Gln Cys Asn Val
        275                 280                 285

Thr Cys Gly Ser Gly Ile Arg Val Arg Lys Arg Lys Gly Ser Asn Lys
    290                 295                 300

Lys Ala Glu Asp Leu Thr Leu Glu Asp Ile Asp Thr Glu Ile Cys Lys
305                 310                 315                 320

Met Asp Lys Cys Ser Ser Ile Phe Asn Ile Val Ser Asn Ser Leu Gly
                325                 330                 335

Phe Val Ile Leu Leu Val Leu Val Phe Phe Asn
            340                 345
```

<210> SEQ ID NO 17
<211> LENGTH: 1284
<212> TYPE: DNA
<213> ORGANISM: Plasmodium yoelii

<400> SEQUENCE: 17

```
atgaagaagt gtaccatttt agttgtagcg tcacttttat tagttgattc tctacttcca      60
ggatatggac aaaataaaag tgtccaagcc caaagaaact taaacgagct atgttacaat     120
gaagaaaatg ataataaatt gtatcacgtc cttaactcga gaatggaaa aatatacaat     180
cgaaatatag tcaacagatt acttggcgat gctctcaacg aaaaccaga agaaaaaaaa     240
gatgatcccc caaagatgg caacaaagat gatcttccaa agaaggaaa aaaagatgat     300
cttccaaaag aagaaaaaaa agatgatccc ccaaagatc ctaaaaaaga tgatccacca     360
aaagaggctc aaaataaatt gaatcaacca gtagtggcag atgaaaatgt agatcaaggg     420
ccaggagcac acaagggcc aggagcacca caagggccag gagcaccaca ggggccagga     480
gcaccacagg ggccaggagc accacaaggg ccaggagcac acaaggacc aggagcacca     540
caagggccag gagcaccaca agggccagga gcaccaaag gccaggagc accacagggg     600
ccaggagcac acaagggcc aggagcacca caaggaccag gagcaccaca gggtccagga     660
gcaccacaag gaccaggagc accacaagga ccaggagcac acaaggtcc aggagcacca     720
cagggtccag gagcaccaca gggtccagga gcaccacaag gaccaggagc accacagggg     780
ccaggagcac acaaggacc aggagcacca caaggaccag gagcaccaca ggggccagga     840
gcaccacaag gccaggagc accacaagaa ccaccccaac aaccacccca caaccacca     900
caacagccac cacaacagcc accacaacag ccaccacaac agccaccaca caaccacgc     960
ccacagccag atggtaataa caacataac aataataatg gtaataataa tgaagattct    1020
tatgtcccaa gcgcggaaca aatactagaa tttgttaaac agataagtag tcaactcaca    1080
gaggaatggt ctcaatgtag tgtaacctgt ggttctggtg taagagttag aaaacgaaaa    1140
aatgtaaaca agcaaccaga aaatttgacc ttagaggata ttgatactga aatttgtaaa    1200
atggataaat gttcaagtat atttaatatt gtaagcaatt cattaggatt tgtaatatta    1260
ttagtattag tattctttaa ttaa                                          1284
```

<210> SEQ ID NO 18
<211> LENGTH: 427
<212> TYPE: PRT
<213> ORGANISM: Plasmodium yoelii

<400> SEQUENCE: 18

```
Met Lys Lys Cys Thr Ile Leu Val Val Ala Ser Leu Leu Val Asp
 1               5                  10                  15

Ser Leu Leu Pro Gly Tyr Gly Gln Asn Lys Ser Val Gln Ala Gln Arg
                20                  25                  30

Asn Leu Asn Glu Leu Cys Tyr Asn Glu Glu Asn Asp Asn Lys Leu Tyr
            35                  40                  45

His Val Leu Asn Ser Lys Asn Gly Lys Ile Tyr Asn Arg Asn Ile Val
        50                  55                  60

Asn Arg Leu Leu Gly Asp Ala Leu Asn Gly Lys Pro Glu Glu Lys Lys
65                  70                  75                  80

Asp Asp Pro Pro Lys Asp Gly Asn Lys Asp Asp Leu Pro Lys Glu Gly
                85                  90                  95
```

```
Lys Lys Asp Asp Leu Pro Lys Glu Glu Lys Lys Asp Asp Pro Pro Lys
                100                 105                 110

Asp Pro Lys Lys Asp Asp Pro Pro Lys Glu Ala Gln Asn Lys Leu Asn
            115                 120                 125

Gln Pro Val Val Ala Asp Glu Asn Val Asp Gln Gly Pro Gly Ala Pro
        130                 135                 140

Gln Gly Pro Gly Ala Pro Gln Gly Pro Gly Ala Pro Gln Gly Pro Gly
145                 150                 155                 160

Ala Pro Gln Gly Pro Gly Ala Pro Gln Gly Pro Gly Ala Pro Gln Gly
                165                 170                 175

Pro Gly Ala Pro Gln Gly Pro Gly Ala Pro Gln Gly Pro Gly Ala Pro
            180                 185                 190

Gln Gly Pro Gly Ala Pro Gln Gly Pro Gly Ala Pro Gln Gly Pro Gly
        195                 200                 205

Ala Pro Gln Gly Pro Gly Ala Pro Gln Gly Pro Gly Ala Pro Gln Gly
    210                 215                 220

Pro Gly Ala Pro Gln Gly Pro Gly Ala Pro Gln Gly Pro Gly Ala Pro
225                 230                 235                 240

Gln Gly Pro Gly Ala Pro Gln Gly Pro Gly Ala Pro Gln Gly Pro Gly
                245                 250                 255

Ala Pro Gln Gly Pro Gly Ala Pro Gln Gly Pro Gly Ala Pro Gln Gly
            260                 265                 270

Pro Gly Ala Pro Gln Gly Pro Gly Ala Pro Gln Gly Pro Gly Ala Pro
        275                 280                 285

Gln Glu Pro Pro Gln Gln Pro Pro Gln Gln Pro Pro Gln Gln Pro Pro
290                 295                 300

Gln Gln Pro Pro Gln Gln Pro Pro Gln Gln Pro Pro Gln Gln Pro Arg
305                 310                 315                 320

Pro Gln Pro Asp Gly Asn Asn Asn Asn Asn Asn Asn Gly Asn Asn
                325                 330                 335

Asn Glu Asp Ser Tyr Val Pro Ser Ala Glu Gln Ile Leu Glu Phe Val
            340                 345                 350

Lys Gln Ile Ser Ser Gln Leu Thr Glu Glu Trp Ser Gln Cys Ser Val
        355                 360                 365

Thr Cys Gly Ser Gly Val Arg Val Arg Lys Lys Asn Val Asn Lys
370                 375                 380

Gln Pro Glu Asn Leu Thr Leu Glu Asp Ile Asp Thr Glu Ile Cys Lys
385                 390                 395                 400

Met Asp Lys Cys Ser Ser Ile Phe Asn Ile Val Ser Asn Ser Leu Gly
                405                 410                 415

Phe Val Ile Leu Leu Val Leu Val Phe Phe Asn
            420                 425

<210> SEQ ID NO 19
<211> LENGTH: 1260
<212> TYPE: DNA
<213> ORGANISM: Plasmodium gallinaceum

<400> SEQUENCE: 19
tgatttcact aaaaatttta atatatataa tataatagtt taaaatagtg aagaatatat      60
ataggtgtac ttcaaaatga agaaattagc cattttatcg gcatcttcgt ttttatttgc     120
tgactttcta tttcaagagt atcaacacaa tggaaactac aaaaatttta gacttttaaa     180
tgaggtgtgt tataataata tgaatattca attatataat gaattggaaa tggaaaatta     240
```

```
catgagtaac acatatttct ataataataa aaaaaccatt agattacttg gagaaaatga    300
taatgaagca atgttaata gagcaaataa taatgtagca atgataata gagcaaatgg    360 taatagagga aatgttaata gagcaaatga tagaaatata ccatatttta gagaaaatgt    420
tgtgaatctt aatcaaccag ttggaggaaa tggtggtgtt caacctgctg gaggaaatgg    480
tggtgttcaa cctgctggag gaaatggtgg tgttcaacct gctggaggta atggtggtgt    540
tcaacctgct ggaggaaatg gtggtgttca acctgctgga ggaaatggtg gtgttcaacc    600
tgctggaggt aatggtggtg ttcaacctgc tggaggcaat ggtggtgctc aaccagttgc    660
agcaggtggt ggtgctcaac cagttgtagc agatggtggt gttcagcctc ttagacaaga    720
aggtgatgct gaagaggatg gaggaaatgg tggtgcccaa ccagctggag gaaatggtgg    780
tgctcaacca gctggaggaa atggtggtgc tcaaccagct ggaggaaatg gtggtgccca    840
acctgctgga ggaaatggtg gtgctcaacc tgctggagga aatgatgctg ctaaacctga    900
tggaggaaat gatgatgaca aacctgaagg aggagatgaa aaatctgaag aagaaaagga    960
ggatgaacca ataccagatc caactcaaga agaaatagat aaatatttaa aaagcatact   1020
tggtaatgtt acatctgaat ggactaattg caatgtaaca tgtgggaaag gtatacaagc   1080
taaaataaaa tctacatctg ctaataagaa aagaagaaga attactccaa atgatgttga   1140
agtaaaaatt tgcgaactag aaagatgttc ttttagcata tttaatgtta taagcaattc   1200
gttaggttta gctataattt taacctttt atttttttat taaataaata ttataaaatt   1260
```

<210> SEQ ID NO 20
<211> LENGTH: 388
<212> TYPE: PRT
<213> ORGANISM: Plasmodium gallinaceum

<400> SEQUENCE: 20

```
Met Lys Lys Leu Ala Ile Leu Ser Ala Ser Ser Phe Leu Phe Ala Asp
 1               5                   10                  15

Phe Leu Phe Gln Glu Tyr Gln His Asn Gly Asn Tyr Lys Asn Phe Arg
            20                  25                  30

Leu Leu Asn Glu Val Cys Tyr Asn Asn Met Asn Ile Gln Leu Tyr Asn
        35                  40                  45

Glu Leu Glu Met Glu Asn Tyr Met Ser Asn Thr Tyr Phe Tyr Asn Asn
    50                  55                  60

Lys Lys Thr Ile Arg Leu Leu Gly Glu Asn Asp Asn Glu Ala Asn Val
 65                  70                  75                  80

Asn Arg Ala Asn Asn Asn Val Ala Asn Asp Arg Ala Asn Gly Asn
                85                  90                  95

Arg Gly Asn Val Asn Arg Ala Asn Asp Arg Asn Ile Pro Tyr Phe Arg
            100                 105                 110

Glu Asn Val Val Asn Leu Asn Gln Pro Val Gly Gly Asn Gly Gly Val
        115                 120                 125

Gln Pro Ala Gly Gly Asn Gly Gly Val Gln Pro Ala Gly Gly Asn Gly
    130                 135                 140

Gly Val Gln Pro Ala Gly Gly Asn Gly Gly Val Gln Pro Ala Gly Gly
145                 150                 155                 160

Asn Gly Gly Val Gln Pro Ala Gly Gly Asn Gly Gly Val Gln Pro Ala
                165                 170                 175

Gly Gly Asn Gly Gly Val Gln Pro Ala Gly Asn Gly Gly Ala Gln
            180                 185                 190

Pro Val Ala Ala Gly Gly Gly Ala Gln Pro Val Val Ala Asp Gly Gly
```

```
                195                 200                 205
Val Gln Pro Leu Arg Gln Glu Gly Asp Ala Glu Asp Gly Gly Asn
210                 215                 220

Gly Gly Ala Gln Pro Ala Gly Asn Gly Gly Ala Gln Pro Ala Gly
225                 230                 235                 240

Gly Asn Gly Gly Ala Gln Pro Ala Gly Asn Gly Gly Ala Gln Pro
                245                 250                 255

Ala Gly Gly Asn Gly Gly Ala Gln Pro Ala Gly Asn Asp Ala Ala
            260                 265                 270

Lys Pro Asp Gly Gly Asn Asp Asp Lys Pro Glu Gly Gly Asp Glu
            275                 280                 285

Lys Ser Glu Glu Glu Lys Glu Asp Glu Pro Ile Pro Asp Pro Thr Gln
            290                 295                 300

Glu Glu Ile Asp Lys Tyr Leu Lys Ser Ile Leu Gly Asn Val Thr Ser
305                 310                 315                 320

Glu Trp Thr Asn Cys Asn Val Thr Cys Gly Lys Gly Ile Gln Ala Lys
                325                 330                 335

Ile Lys Ser Thr Ser Ala Asn Lys Lys Arg Glu Glu Ile Thr Pro Asn
            340                 345                 350

Asp Val Glu Val Lys Ile Cys Glu Leu Glu Arg Cys Ser Phe Ser Ile
            355                 360                 365

Phe Asn Val Ile Ser Asn Ser Leu Gly Leu Ala Ile Ile Leu Thr Phe
            370                 375                 380

Leu Phe Phe Tyr
385

<210> SEQ ID NO 21
<211> LENGTH: 24
<212> TYPE: PRT
<213> ORGANISM: Plasmodium falciparum

<400> SEQUENCE: 21

Asp Lys Arg Asp Gly Asn Asn Glu Asp Asn Glu Lys Leu Arg Lys Pro
1               5                   10                  15

Lys His Lys Lys Leu Lys Gln Pro
            20

<210> SEQ ID NO 22
<211> LENGTH: 24
<212> TYPE: PRT
<213> ORGANISM: Plasmodium vivax

<400> SEQUENCE: 22

Asp Ala Lys Lys Lys Lys Asp Gly Lys Lys Ala Glu Pro Lys Asn Pro
1               5                   10                  15

Arg Glu Asn Lys Leu Lys Gln Pro
            20

<210> SEQ ID NO 23
<211> LENGTH: 24
<212> TYPE: PRT
<213> ORGANISM: Plasmodium simium

<400> SEQUENCE: 23

Asp Ala Lys Lys Lys Lys Asp Gly Lys Lys Ala Glu Pro Lys Asn Pro
1               5                   10                  15

Arg Glu Asn Lys Leu Lys Gln Pro
            20
```

<210> SEQ ID NO 24
<211> LENGTH: 24
<212> TYPE: PRT
<213> ORGANISM: Plasmodium knowlesi

<400> SEQUENCE: 24

Lys Lys Lys Glu Lys Gly Lys Glu Lys Glu Glu Pro Lys Lys Pro
1               5                   10                  15

Asn Glu Asn Lys Leu Lys Gln Pro
            20

<210> SEQ ID NO 25
<211> LENGTH: 24
<212> TYPE: PRT
<213> ORGANISM: Plasmodium cynomolgi

<400> SEQUENCE: 25

Asp Lys Pro Lys Lys Lys Asp Glu Lys Gln Val Glu Pro Lys Lys Pro
1               5                   10                  15

Arg Glu Asn Lys Leu Lys Gln Pro
            20

<210> SEQ ID NO 26
<211> LENGTH: 24
<212> TYPE: PRT
<213> ORGANISM: Plasmodium brasilianum

<400> SEQUENCE: 26

Lys Asp Gly Asn Val Thr Asn Glu Arg Lys Lys Lys Pro Thr Lys Ala
1               5                   10                  15

Val Glu Asn Lys Leu Lys Gln Pro
            20

<210> SEQ ID NO 27
<211> LENGTH: 24
<212> TYPE: PRT
<213> ORGANISM: Plasmodium malariae

<400> SEQUENCE: 27

Lys Asp Gly Asn Val Thr Asn Glu Arg Lys Lys Lys Pro Thr Lys Ala
1               5                   10                  15

Val Glu Asn Lys Leu Lys Gln Pro
            20

<210> SEQ ID NO 28
<211> LENGTH: 24
<212> TYPE: PRT
<213> ORGANISM: Plasmodium berghei

<400> SEQUENCE: 28

Asp Ala Pro Glu Gly Lys Lys Asn Glu Lys Lys Asn Glu Lys Ile Glu
1               5                   10                  15

Arg Asn Asn Lys Leu Lys Gln Pro
            20

<210> SEQ ID NO 29
<211> LENGTH: 24
<212> TYPE: PRT
<213> ORGANISM: Plasmodium yoelii

<400> SEQUENCE: 29

-continued

Asn Lys Asp Ala Pro Lys Glu Glu Lys Lys Ala Asp Pro Pro Lys Glu
1               5                   10                  15

Ala Gln Asn Lys Leu Lys Gln Pro
            20

<210> SEQ ID NO 30
<211> LENGTH: 24
<212> TYPE: PRT
<213> ORGANISM: Plasmodium gallinaceum

<400> SEQUENCE: 30

Gly Asn Val Asn Arg Ala Asn Asp Arg Asn Ile Pro Tyr Phe Arg Glu
1               5                   10                  15

Asn Val Val Asn Leu Asn Gln Pro
            20

<210> SEQ ID NO 31
<211> LENGTH: 19
<212> TYPE: PRT
<213> ORGANISM: Plasmodium falciparum

<400> SEQUENCE: 31

Glu Trp Ser Pro Cys Ser Val Thr Cys Gly Asn Gly Ile Gln Val Arg
1               5                   10                  15

Ile Lys Pro

<210> SEQ ID NO 32
<211> LENGTH: 19
<212> TYPE: PRT
<213> ORGANISM: Plasmodium vivax

<400> SEQUENCE: 32

Glu Trp Thr Pro Cys Ser Val Thr Cys Gly Val Gly Val Arg Val Arg
1               5                   10                  15

Ser Arg Val

<210> SEQ ID NO 33
<211> LENGTH: 19
<212> TYPE: PRT
<213> ORGANISM: Plasmodium simium

<400> SEQUENCE: 33

Glu Trp Thr Pro Cys Ser Val Thr Cys Gly Val Gly Val Arg Val Arg
1               5                   10                  15

Arg Arg Val

<210> SEQ ID NO 34
<211> LENGTH: 19
<212> TYPE: PRT
<213> ORGANISM: Plasmodium knowlesi

<400> SEQUENCE: 34

Gln Trp Thr Pro Cys Ser Val Thr Cys Gly Asn Gly Val Arg Ile Arg
1               5                   10                  15

Arg Lys Ala

<210> SEQ ID NO 35
<211> LENGTH: 19
<212> TYPE: PRT
<213> ORGANISM: Plasmodium cynomolgi

<400> SEQUENCE: 35

-continued

Glu Trp Ser Pro Cys Ser Val Thr Cys Gly Lys Gly Val Arg Met Arg
1               5                   10                  15

Arg Lys Val

<210> SEQ ID NO 36
<211> LENGTH: 19
<212> TYPE: PRT
<213> ORGANISM: Plasmodium brasilianum

<400> SEQUENCE: 36

Glu Trp Ser Pro Cys Ser Val Thr Cys Gly Ser Gly Ile Arg Ala Arg
1               5                   10                  15

Arg Lys Val

<210> SEQ ID NO 37
<211> LENGTH: 19
<212> TYPE: PRT
<213> ORGANISM: Plasmodium malariae

<400> SEQUENCE: 37

Glu Trp Ser Pro Cys Ser Val Thr Cys Gly Ser Gly Ile Arg Ala Arg
1               5                   10                  15

Arg Lys Val

<210> SEQ ID NO 38
<211> LENGTH: 19
<212> TYPE: PRT
<213> ORGANISM: Plasmodium berghei

<400> SEQUENCE: 38

Gln Trp Ser Gln Cys Asn Val Thr Cys Gly Ser Gly Ile Arg Val Arg
1               5                   10                  15

Lys Arg Lys

<210> SEQ ID NO 39
<211> LENGTH: 19
<212> TYPE: PRT
<213> ORGANISM: Plasmodium yoelii

<400> SEQUENCE: 39

Glu Trp Ser Gln Cys Ser Val Thr Cys Gly Ser Gly Val Arg Val Arg
1               5                   10                  15

Lys Arg Lys

<210> SEQ ID NO 40
<211> LENGTH: 19
<212> TYPE: PRT
<213> ORGANISM: Plasmodium gallinaceum

<400> SEQUENCE: 40

Glu Trp Thr Asn Cys Asn Val Thr Cys Gly Lys Gly Ile Gln Ala Lys
1               5                   10                  15

Ile Lys Ser

<210> SEQ ID NO 41
<211> LENGTH: 18
<212> TYPE: PRT
<213> ORGANISM: Homo sapiens

<400> SEQUENCE: 41

Glu Trp Ser Pro Cys Ser Val Thr Cys Gly Lys Gly Thr Arg Ser Arg
1               5                   10                  15

Lys Arg

<210> SEQ ID NO 42
<211> LENGTH: 18
<212> TYPE: PRT
<213> ORGANISM: Homo sapiens

<400> SEQUENCE: 42

Glu Trp Thr Ser Cys Ser Val Thr Cys Gly Asn Gly Ile Gln Gln Arg
1               5                   10                  15

Gly Arg

<210> SEQ ID NO 43
<211> LENGTH: 18
<212> TYPE: PRT
<213> ORGANISM: Homo sapiens

<400> SEQUENCE: 43

Pro Trp Ser Ser Cys Gly Val Thr Cys Gly Asp Gly Val Ile Thr Arg
1               5                   10                  15

Ile Arg

<210> SEQ ID NO 44
<211> LENGTH: 18
<212> TYPE: PRT
<213> ORGANISM: Homo sapiens

<400> SEQUENCE: 44

Pro Trp Asp Ile Cys Ser Val Thr Cys Gly Asp Gly Val Ile Thr Arg
1               5                   10                  15

Ile Arg

<210> SEQ ID NO 45
<211> LENGTH: 18
<212> TYPE: PRT
<213> ORGANISM: Homo sapiens

<400> SEQUENCE: 45

Pro Trp Ser Pro Cys Ser Val Thr Cys Ser Glu Gly Ser Gln Arg His
1               5                   10                  15

Arg Arg

<210> SEQ ID NO 46
<211> LENGTH: 18
<212> TYPE: PRT
<213> ORGANISM: Homo sapiens

<400> SEQUENCE: 46

Pro Trp Gly Pro Cys Ser Val Thr Cys Ser Lys Gly Thr Gln Ile Arg
1               5                   10                  15

Gln Arg

<210> SEQ ID NO 47
<211> LENGTH: 18
<212> TYPE: PRT
<213> ORGANISM: Homo sapiens

<400> SEQUENCE: 47

Pro Leu Ser Pro Cys Ser Val Thr Cys Gly Leu Gly Gln Thr Leu Glu

-continued

```
 1               5                   10                  15

Gln Arg

<210> SEQ ID NO 48
<211> LENGTH: 18
<212> TYPE: PRT
<213> ORGANISM: Homo sapiens

<400> SEQUENCE: 48

Ser Pro Trp Ser Cys Ser Val Thr Cys Gly Lys Gly Met Arg Thr Arg
 1               5                   10                  15

Gln Arg
```